(12) United States Patent
Winters et al.

(10) Patent No.: US 9,504,671 B2
(45) Date of Patent: *Nov. 29, 2016

(54) PHARMACEUTICAL COMPOSITIONS OF SPIRO-OXINDOLE COMPOUND FOR TOPICAL ADMINISTRATION AND THEIR USE AS THERAPEUTIC AGENTS

(75) Inventors: Conrad Stewart Winters, Vancouver (CA); Meidong Yang, Playa Del Rey, CA (US); Haigang Chen, Plymouth, MN (US)

(73) Assignee: Xenon Pharmaceuticals Inc., Burnaby, BC (CA)

( * ) Notice: Subject to any disclaimer, the term of this patent is extended or adjusted under 35 U.S.C. 154(b) by 272 days.

This patent is subject to a terminal disclaimer.

(21) Appl. No.: 13/580,129

(22) PCT Filed: Feb. 25, 2011

(86) PCT No.: PCT/US2011/026359
§ 371 (c)(1),
(2), (4) Date: Oct. 30, 2012

(87) PCT Pub. No.: WO2011/106729
PCT Pub. Date: Sep. 1, 2011

(65) Prior Publication Data
US 2013/0143941 A1 Jun. 6, 2013

Related U.S. Application Data

(60) Provisional application No. 61/308,759, filed on Feb. 26, 2010.

(51) Int. Cl.
| | | |
|---|---|---|
| *A61K 31/407* | (2006.01) | |
| *A61K 9/06* | (2006.01) | |
| *A61K 47/10* | (2006.01) | |
| *A61K 9/14* | (2006.01) | |
| *A61K 9/00* | (2006.01) | |

(52) U.S. Cl.
CPC .......... *A61K 31/407* (2013.01); *A61K 9/0014* (2013.01); *A61K 9/06* (2013.01); *A61K 47/10* (2013.01)

(58) Field of Classification Search
CPC ............ C07D 491/107; C07D 491/20; A61K 47/10; A61K 9/0014; A61K 9/14; A61K 9/06; A61K 31/407
See application file for complete search history.

(56) References Cited

U.S. PATENT DOCUMENTS

| | | |
|---|---|---|
| 3,189,617 A | 6/1965 | Archer et al. |
| 3,723,459 A | 3/1973 | Paragamian |
| 3,845,770 A | 11/1974 | Theeuwes et al. |
| 4,045,576 A | 8/1977 | Welstead, Jr. et al. |
| 4,326,525 A | 4/1982 | Swanson et al. |
| 4,438,130 A | 3/1984 | Kaplan |
| 4,440,785 A | 4/1984 | Walsh |
| 4,670,566 A | 6/1987 | Walsh |
| 4,886,788 A | 12/1989 | Skuballa et al. |
| 4,935,446 A | 6/1990 | Imaki et al. |
| 5,023,265 A | 6/1991 | Scherlock et al. |
| 5,116,854 A | 5/1992 | Marfat |
| 5,182,289 A | 1/1993 | Ting et al. |
| 5,278,162 A | 1/1994 | Wilkerson |
| 5,296,478 A | 3/1994 | Teleha |
| 5,304,121 A | 4/1994 | Sahatjian |
| 5,453,516 A | 9/1995 | Fischer et al. |
| 5,663,431 A | 9/1997 | Di Malta et al. |
| 5,686,624 A | 11/1997 | Di Malta et al. |
| 5,696,145 A | 12/1997 | Foulon et al. |
| 5,723,625 A | 3/1998 | Keplinger et al. |
| 5,726,322 A | 3/1998 | Di Malta et al. |
| 5,728,723 A | 3/1998 | Di Malta et al. |
| 5,763,471 A | 6/1998 | Fourtillan et al. |
| 5,767,128 A | 6/1998 | Guillaumet et al. |
| 5,776,936 A | 7/1998 | Lee et al. |
| 5,849,780 A | 12/1998 | Di Malta et al. |
| 5,886,026 A | 3/1999 | Hunter et al. |
| 5,994,350 A | 11/1999 | Foulon et al. |
| 6,046,341 A | 4/2000 | Foulon et al. |
| 6,090,818 A | 7/2000 | Foulon et al. |
| 6,099,562 A | 8/2000 | Ding et al. |
| 6,110,969 A | 8/2000 | Tani et al. |
| 6,225,347 B1 | 5/2001 | Buchmann et al. |

(Continued)

FOREIGN PATENT DOCUMENTS

| | | |
|---|---|---|
| CA | 2095718 A1 | 5/1992 |
| CA | 2107348 A1 | 7/1993 |

(Continued)

OTHER PUBLICATIONS

Remington's: the Science and Practice of Pharmacy, 21$^{st}$ edition, pp. 900, 1079, 1095, 1106.*

Corey and Noe, "Preparation of O-Allyl-N-(9-Anthracenylmethyl)Cinchonidinium Bromide as a Phase Transfer Catalyst for the Enantioselective Alkylation of Glycine Benzophenone Imine tert-Butyl Ester: (4S)-2-(Benzhydrylidenamino)Pentanedioic Acid, 1-tert-Butyl Ester-5-Methyl Ester [[Cinchonanium, 1-(9-anthracenylmethyl)-9-(2-propenyloxy)-, bromide, (8α,9R)-and L-Glutamic acid, N-(diphenylmethylene)-, 1-(1,1-dimethylethyl) 5-methyl ester]]," Organic Syntheses 80(11): 38-45, 2003; col. vol. 11: 404-409.

Dehmlow et al., "Monodeazacinchona Alkaloid Derivatives: Synthesis and Preliminary Applications as Phase-Transfer Catalysts," Eur. J. Org. Chem. 13: 2087-2093, 2002.

(Continued)

Primary Examiner — Sahar Javanmard
(74) Attorney, Agent, or Firm — Seed IP Law Group LLP

(57) ABSTRACT

This invention is directed to pharmaceutical compositions for topical administration to a mammal, wherein the pharmaceutical compositions comprise a spiro-oxindole compound, as an enantiomer, a racemate or a non-racemic mixture, or a pharmaceutically acceptable salt thereof. These pharmaceutical compositions are useful for the treatment and/or prevention of sodium channel-mediated diseases or conditions.

12 Claims, 5 Drawing Sheets

(56) References Cited

U.S. PATENT DOCUMENTS

| | | | |
|---|---|---|---|
| 6,235,780 B1 | 5/2001 | Ohuchida et al. |
| 6,262,293 B1 | 7/2001 | Tani et al. |
| 6,288,119 B1 | 9/2001 | Ohuchida et al. |
| 6,355,627 B1 | 3/2002 | Ishida et al. |
| 6,414,153 B1 | 7/2002 | Kelly et al. |
| 6,670,357 B2 | 12/2003 | Leftheris et al. |
| 6,964,973 B2 | 11/2005 | Zhi et al. |
| 7,368,470 B2 | 5/2008 | Sundermann et al. |
| 7,700,641 B2 | 4/2010 | Chafeev et al. |
| 7,799,798 B2 | 9/2010 | Chafeev et al. |
| 7,888,345 B2 | 2/2011 | Hoyt et al. |
| 7,935,721 B2 | 5/2011 | Sun et al. |
| 8,101,647 B2 | 1/2012 | Chafeev et al. |
| 8,106,087 B2 | 1/2012 | Chafeev et al. |
| 8,263,606 B2 | 9/2012 | Chafeev et al. |
| 8,415,370 B2 | 4/2013 | Chaeev et al. |
| 2002/0039790 A1 | 4/2002 | Keplinger et al. |
| 2004/0038970 A1 | 2/2004 | Thurieau et al. |
| 2004/0167224 A1 | 8/2004 | Ozaki et al. |
| 2005/0004137 A1 | 1/2005 | Romano |
| 2005/0004138 A1 | 1/2005 | Romano |
| 2005/0014764 A1 | 1/2005 | Romano et al. |
| 2005/0020617 A1 | 1/2005 | Bastian et al. |
| 2005/0038036 A1 | 2/2005 | Romano et al. |
| 2005/0075351 A1 | 4/2005 | Berg et al. |
| 2005/0153998 A1 | 7/2005 | Ito et al. |
| 2005/0159473 A1 | 7/2005 | Sall et al. |
| 2005/0171186 A1 | 8/2005 | Fensome et al. |
| 2005/0256110 A1 | 11/2005 | Collins et al. |
| 2005/0256144 A1 | 11/2005 | Kath et al. |
| 2006/0247441 A1 | 11/2006 | Wilk |
| 2007/0049609 A1 | 3/2007 | Broka et al. |
| 2007/0072831 A1 | 3/2007 | Cai et al. |
| 2007/0105820 A1 | 5/2007 | Chafeev et al. |
| 2007/0299102 A1 | 12/2007 | Felding et al. |
| 2008/0103151 A9 | 5/2008 | Chafeev et al. |
| 2010/0331386 A1 | 12/2010 | Chafeev et al. |
| 2011/0034500 A1 | 2/2011 | Chafeev et al. |
| 2011/0086899 A1 | 4/2011 | Winters et al. |
| 2011/0087027 A1 | 4/2011 | Cadieux et al. |
| 2011/0172282 A9 | 7/2011 | Chafeev et al. |
| 2011/0237567 A9 | 9/2011 | Chafeev et al. |
| 2011/0269788 A1 | 11/2011 | Cadieux et al. |
| 2011/0294842 A9 | 12/2011 | Cadieux et al. |
| 2012/0122909 A9 | 5/2012 | Chafeev et al. |
| 2013/0072537 A1 | 3/2013 | Chafeev et al. |
| 2013/0072686 A1 | 3/2013 | Cadieux et al. |
| 2013/0143941 A1 | 6/2013 | Winters et al. |
| 2013/0252962 A1 | 9/2013 | Chafeev et al. |
| 2013/0274483 A1 | 10/2013 | Sun et al. |
| 2014/0336390 A1 | 11/2014 | Cadieux et al. |
| 2015/0025121 A1 | 1/2015 | Chafeev et al. |

FOREIGN PATENT DOCUMENTS

| | | | |
|---|---|---|---|
| CA | 2129215 A1 | 1/1995 |
| CA | 2274898 A1 | 6/1998 |
| CA | 2450550 A1 | 1/2003 |
| CA | 2466915 A1 | 8/2003 |
| CA | 2487494 A1 | 12/2003 |
| CA | 2235686 C | 6/2007 |
| DE | 1956237 A | 5/1971 |
| DE | 2113343 A1 | 9/1972 |
| EP | 0147805 A2 | 7/1985 |
| EP | 0164860 A1 | 12/1985 |
| EP | 0175551 A1 | 3/1986 |
| EP | 0608058 A1 | 7/1994 |
| EP | 1422217 A2 | 5/2004 |
| EP | 1557166 A1 | 7/2005 |
| EP | 2 073 806 B1 | 2/2012 |
| FR | 2722195 A1 | 1/1996 |
| JP | H07508976 A | 10/1995 |
| JP | 1095766 A | 4/1998 |
| JP | 2003505388 | 2/2003 |
| JP | 2006-519224 A | 8/2006 |
| WO | WO 86/03749 A1 | 7/1986 |
| WO | WO 91/01306 A1 | 2/1991 |
| WO | WO 91/04974 A1 | 4/1991 |
| WO | WO 91/06545 A1 | 5/1991 |
| WO | WO 92/09577 A1 | 6/1992 |
| WO | WO 93/12786 A1 | 7/1993 |
| WO | WO 93/15051 A1 | 8/1993 |
| WO | WO 93/23083 A1 | 11/1993 |
| WO | WO 94/03427 A1 | 2/1994 |
| WO | WO 95/06688 A1 | 3/1995 |
| WO | WO 95/14667 A1 | 6/1995 |
| WO | WO 96/19477 A1 | 6/1996 |
| WO | WO 97/15556 A1 | 5/1997 |
| WO | WO 97/36895 A1 | 10/1997 |
| WO | WO 98/25901 A1 | 6/1998 |
| WO | WO 98/50016 A2 | 11/1998 |
| WO | WO 00/06556 A1 | 2/2000 |
| WO | WO 00/42044 A1 | 7/2000 |
| WO | WO 00/71129 A1 | 11/2000 |
| WO | WO 0105790 A1 | 1/2001 |
| WO | WO 01/38564 A2 | 5/2001 |
| WO | WO 01/38564 A3 | 5/2001 |
| WO | WO 01/74775 A1 | 10/2001 |
| WO | WO 02/30868 A1 | 4/2002 |
| WO | WO 02/38544 A2 | 5/2002 |
| WO | WO 03/000677 A1 | 1/2003 |
| WO | WO 03/037274 A2 | 5/2003 |
| WO | WO 03/037890 A2 | 5/2003 |
| WO | WO 03/064425 A1 | 8/2003 |
| WO | WO 03/078394 A1 | 9/2003 |
| WO | WO 03/106457 A1 | 12/2003 |
| WO | WO 2004/000225 A2 | 12/2003 |
| WO | WO 2004/000227 A2 | 12/2003 |
| WO | WO 2004/048320 A1 | 6/2004 |
| WO | WO 2004/074285 A1 | 9/2004 |
| WO | WO 2005/011657 A2 | 2/2005 |
| WO | WO 2005/016913 A1 | 2/2005 |
| WO | WO 2005/019208 A1 | 3/2005 |
| WO | WO 2005/035498 A1 | 4/2005 |
| WO | WO 2005/056554 A2 | 6/2005 |
| WO | WO 2005/070919 A1 | 8/2005 |
| WO | WO 2005/092304 A2 | 10/2005 |
| WO | WO 2005/092895 A2 | 10/2005 |
| WO | WO 2005/097107 A2 | 10/2005 |
| WO | WO 2005/097122 A2 | 10/2005 |
| WO | WO 2005/097136 A1 | 10/2005 |
| WO | WO 2005/099689 A1 | 10/2005 |
| WO | WO 2005/104711 A2 | 11/2005 |
| WO | WO 2005/105753 A2 | 11/2005 |
| WO | WO 2005/110992 A1 | 11/2005 |
| WO | WO 2005/111024 A1 | 11/2005 |
| WO | WO 2006/012173 A1 | 2/2006 |
| WO | WO 2006/017075 A1 | 2/2006 |
| WO | WO 2006/023107 A1 | 3/2006 |
| WO | WO 2006/023109 A1 | 3/2006 |
| WO | WO 2006/049290 A1 | 5/2006 |
| WO | WO 2006/055752 A2 | 5/2006 |
| WO | WO 2006/087019 A1 | 8/2006 |
| WO | WO 2006/091646 A2 | 8/2006 |
| WO | WO 2006/110654 A1 | 10/2006 |
| WO | WO 2006/110917 A2 | 10/2006 |
| WO | WO 2006/113864 A2 | 10/2006 |
| WO | WO 2006/113875 A2 | 10/2006 |
| WO | WO 2007/025925 A1 | 3/2007 |
| WO | WO 2008/046046 A1 | 4/2008 |
| WO | WO 2008/046049 A1 | 4/2008 |
| WO | WO 2008/046065 A1 | 4/2008 |
| WO | WO 2008/046082 A2 | 4/2008 |
| WO | WO 2008/046083 A2 | 4/2008 |
| WO | WO 2008/046084 A2 | 4/2008 |
| WO | WO 2008/046087 A2 | 4/2008 |
| WO | WO 2008/060789 A1 | 5/2008 |
| WO | WO 2008/110741 A2 | 9/2008 |
| WO | WO 2008/117050 A1 | 10/2008 |
| WO | WO 2008/153801 A1 | 12/2008 |
| WO | WO 2010/045197 A1 | 4/2010 |
| WO | WO 2010/045251 A2 | 4/2010 |
| WO | WO 2010/053998 A1 | 5/2010 |
| WO | WO 2010/078307 A1 | 7/2010 |

(56) References Cited

FOREIGN PATENT DOCUMENTS

| WO | WO 2010/132352 A2 | 11/2010 |
|---|---|---|
| WO | WO 2011/002708 A1 | 1/2011 |
| WO | WO 2011/047173 A9 | 4/2011 |
| WO | WO 2011/047174 A1 | 4/2011 |
| WO | WO 2011/106729 A2 | 9/2011 |
| WO | WO 2011/106729 A3 | 9/2011 |
| WO | WO 2013/154712 A1 | 10/2013 |

OTHER PUBLICATIONS

Li et al., "Emerging drug targets for pain treatment," *European Journal of Pharmacology* 681: 1-5, 2012.

Morie et al., "Asymmetric Synthesis of the Enantiomers of 2-Aminomethyl-4-(4-Fluorobenzyl)morpholine, an Intermediate of Mosapride, a Gastroprokinetic Agent," *Heterocycles* 38(5): 1033-1040, 1994.

Ooi and Maruoka, "Recent Advances in Asymmetric Phase-Transfer Catalysis," *Angew. Chem. Int. Ed.* 46: 4222-4266, 2007.

Swamy et al., "Mitsunobu and Related Reactions: Advances and Applications," *Chem. Rev.* 109: 2551-2651, 2009.

Response to Official Action from Canadian Intellectual Property Office, mailed Feb. 14, 2013, for Patent Application No. 2,604,115, 3 pages.

Official Action from Canadian Intellectual Property Office, dated May 6, 2013, for Patent Application No. 2,604,115, 2 pages.

Official Action from State Intellectual Property Office of China, dated May 24, 2013, for Patent Application No. 201110027693.X, 12 pages.

Response to Official Action from European Patent Office re extended European search report, dated Dec. 13, 2012, for Patent Application No. 11009687.2, 9 pages.

Official Action from European Patent Office, dated Jan. 28, 2013, for Patent Application No. 11009687.2, 3 pages.

Response to Official Action from European Patent Office, dated Jul. 18, 2013, for Patent Application No. 11009687.2, 59 pages.

Translation of Official Action from Israel Patent Office, dated Dec. 19, 2012, for Patent Application No. 186616, 3 pages.

Translation of Official Action from Korean Intellectual Property Office, mailed Feb. 27, 2013, for Patent Application No. 10-2007-7026134, 4 pages.

Translation of Official Action from Korean Intellectual Property Office, mailed Nov. 4, 2013, for Patent Application No. 10-2007-7026134, 4 pages.

Translation of Official Action from Korean Intellectual Property Office, mailed Oct. 11, 2013, for Patent Application No. 10-2013-7016857, 1 page.

Official Action from New Zealand Intellectual Property Office, dated Dec. 6, 2012, for Patent Application No. 599334, 2 pages.

Cadieux et al., entitled Synthetic Methods for Spiro-Oxindole Compounds, Notice of Allowance mailed Jan. 24, 2013, for U.S. Appl. No. 12/904,880, 11 pages.

Cadieux et al., entitled Synthetic Methods for Spiro-Oxindole Compounds, Office Action mailed Feb. 1, 2013, for U.S. Appl. No. 13/620,391, 42 pages.

Cadieux et al., entitled Synthetic Methods for Spiro-Oxindole Compounds, Amendment filed May 1, 2013, for U.S. Appl. No. 13/620,391, 7 pages.

Cadieux et al., entitled Synthetic Methods for Spiro-Oxindole Compounds, Office Action mailed Jul. 31, 2013, for U.S. Appl. No. 13/620,391, 6 pages.

Cadieux et al., entitled Synthetic Methods for Spiro-Oxindole Compounds, Amendment filed Oct. 31, 2013, for U.S. Appl. No. 13/620,391, 8 pages.

Cadieux et al., entitled Synthetic Methods for Spiro-Oxindole Compounds, Notice of Allowance mailed Jan. 22, 2014, for U.S. Appl. No. 13/620,391, 12 pages.

Translation of Official Action from State Intellectual Property Office of China, dated Jan. 28, 2013, for Patent Application No. 200780038111.X, 8 pages.

Translation of Official Action from Patent Office of Japan, dated May 29, 2013, for Patent Application No. 2009-532606, 5 pages.

Chafeev et al., entitled Use of Spiro-Oxindole Compounds as Therapeutic Agents, Notice of Allowance, mailed Feb. 28, 2013, for U.S. Appl. No. 12/445,264, 56 pages.

Translation of Official Action from State Intellectual Property Office of China, dated Jul. 17, 2013, for Patent Application No. 201080029572.2, 5 pages.

Official Action from Intellectual Property Office of New Zealand, dated Oct. 12, 2012, for Patent Application No. 596903, 1 page.

Chafeev et al., entitled Enantiomers of Spiro-Oxindole Compounds and Their Uses as Therapeutic Agents, Notice of Allowance, mailed Jan. 31, 2013, for U.S. Appl. No. 12/825,168, 9 pages.

Chafeev et al., entitled Enantiomers of Spiro-Oxindole Compounds and Their Uses as Therapeutic Agents, Preliminary Amendment filed Dec. 3, 2012, for U.S. Appl. No. 13/619,915, 7 pages.

Chafeev et al., entitled Enantiomers of Spiro-Oxindole Compounds and Their Uses as Therapeutic Agents, Restriction Requirement mailed Feb. 27, 2013, for U.S. Appl. No. 13/619,915, 8 pages.

Chafeev et al., entitled Enantiomers of Spiro-Oxindole Compounds and Their Uses as Therapeutic Agents, Response to Restriction Requirement dated Jun. 27, 2013, for U.S. Appl. No. 13/619,915, 3 pages.

Chafeev et al., entitled Enantiomers of Spiro-Oxindole Compounds and Their Uses as Therapeutic Agents, Office Action mailed Sep. 30, 2013, for U.S. Appl. No. 13/619,915, 51 pages.

Official Action from Intellectual Property Australia, dated Sep. 17, 2013, for Patent Application No. 2009303468, 4 pages.

Translation of Official Action from State Intellectual Property Office of China, dated Mar. 29, 2013, for Patent Application No. 200980150848.X, 6 pages.

Translation of Official Action from State Intellectual Property Office of China, dated Dec. 9, 2013, for Patent Application No. 200980150848.X, 6 pages.

Translation of Official Action from Korean Intellectual Property Office, dated Nov. 9, 2012, for Patent Application No. 10-2011-7011106, 9 pages.

Chafeev et al., entitled Spiro-Oxindole Compounds and Their Use as Therapeutic Agents, Notice of Allowance mailed Nov. 27, 2012, for U.S. Appl. No. 13/557,833, 46 pages.

Chafeev et al., entitled Spiro-Oxindole Compounds and Their Use as Therapeutic Agents, Preliminary Amendment dated Jun. 12, 2013, for U.S. Appl. No. 13/787,558, 11 pages.

Chafeev et al., entitled Spiro-Oxindole Compounds and Their Use as Therapeutic Agents, Office Action mailed Aug. 21, 2013, for U.S. Appl. No. 13/787,558, 56 pages.

Chafeev et al., entitled Spiro-Oxindole Compounds and Their Use as Therapeutic Agents, Amendment dated Jan. 21, 2014, for U.S. Appl. No. 13/787,558, 13 pages.

Official Action from European Patent Office, dated Feb. 19, 2013, for Patent Application No. 09 741 118.5, 5 pages.

Response to Official Action from European Patent Office, dated May 23, 2013, for Patent Application No. 09 741 118.5, 65 pages.

Official Action from European Patent Office, dated Nov. 4, 2013, for Patent Application No. 09 741 118.5, 5 pages.

Cadieux et al., entitled Spiro-Oxindole-Derivatives as Sodium Channel Blockers, Restriction Requirement mailed Jul. 5, 2013, for U.S. Appl. No. 13/142,375, 9 pages.

Cadieux et al., entitled Spiro-Oxindole-Derivatives as Sodium Channel Blockers, Response to Restriction Requirement filed Jul. 31, 2013, for U.S. Appl. No. 13/142,375, 2 pages.

Cadieux et al., entitled Spiro-Oxindole-Derivatives as Sodium Channel Blockers, Office Action mailed Aug. 9, 2013, for U.S. Appl. No. 13/142,375, 51 pages.

Official Action from State Intellectual Property Office of China, dated Sep. 18, 2013, for Patent Application No. 201180010245.7, 7 pages.

Official Action from European Patent Office, dated Jul. 19, 2013, for Patent Application No. 11 707 750.3, 7 pages.

Official Action from Intellectual Property Office of New Zealand, mailed May 7, 2013, for New Zealand Patent Application No. 601667, 2 pages.

(56) References Cited

OTHER PUBLICATIONS

Invitation to Pay Additional Fees, mailed May 3, 2013, for PCTAN PCT/US2013/030219, 5 pages.
International Search Report and Written Opinion, mailed Jun. 28, 2013, for PCTAN PCT/US2013/030219, 17 pages.
Adams et al., "Bicyclic N-Hydroxyurea Inhibitors of 5-Lipoxygenase: Pharmacodynamic, Pharmacokinetic, and in Vitro Metabolic Studies Characterizing N-Hydroxy-N-(2,3-dihydro-6-(phenylmethoxy)-3-benzofuranyl)urea," *J. Med. Chem.* 39(26): 5035-5046, 1996.
Akai, "Development of Novel Asymmetric Reactions Oriented to Next-Generation Enzymatic Organic Syntheses," *Yakugaku Zasshi* 123(11): 919-931, 2003.
Al-Thebeiti and El-Zohry, "A Facile Route for the Synthesis of Some New Spiro[indoline-3,3'-indan]-2,1'-dione Derivatives," *Heterocycles* 41(11): 2475-2480, 1995.
Alabaster et al., "The Synthesis of 5-Substituted 2,3-Dihydrobenzofurans," *Synthesis* 12: 950-952, Dec. 1988.
Alcaide et al., "Efficient Entry to Diversely Functionalized Spirocyclic Oxindoles from Isatins through Carbonyl-Addition/Cyclization Reaction Sequences," *J. Org. Chem.* 71(6): 2346-2351, 2006.
Alper et al., "Eine neuartige Methode zur Synthese von Spiro[pyrrolidin-3,3'-oxindolen]: katalysierte Ringerweiterung von Cyclopropanen mit Aldiminen," *Angew. Chem.* 111(21): 3379-3381, 1999.
Alper et al., "Facile, Novel Methodology for the Synthesis of Spiro[pyrrolidin-3,3'-oxindoles]: Catalyzed Ring Expansion Reactions of Cyclopropanes by Aldimines," *Angew. Chem. Int. Ed.* 38(21): 3186-3189, 1999.
Anger et al., "Medicinal Chemistry of Neuronal Voltage-Gated Sodium Channel Blockers," *Journal of Medicinal Chemistry* 44(2): 115-137, Jan. 18, 2001.
Arcangeli et al., "Targeting Ion Channels in Cancer: A Novel Frontier in Antineoplastic Therapy," *Current Medicinal Chemistry* 16: 66-93, 2009.
Autrey and Tahk, "The Synthesis and Stereochemistry of Some Isatylideneacetic Acid Derivatives," *Tetrahedron* 23: 901-917, 1967.
Bacher et al., "Oxindole alkaloids from *Uncaria tomentosa* induce apoptosis in proliferating, G0/G1-arrested and bcl-2-expressing acute lymphoblastic leukaemia cells," *British Journal of Haematology* 132: 615-622, 2005.
Banfi et al., "High Diastereoface Selection in an Ester Enolate Addition to α-Alkoxy Aldehydes: Stereoselective Synthesis of α-Methylene-β-hydroxy-γ-alkoxy Esters," *J. Org. Chem.* 49: 3784-3790, 1984.
Basavaiah et al., "$TiCl_4$ catalyzed tandem construction of C—C and C—O bonds: a simple and one-pot atom-economical stereoselective synthesis of spiro-oxindoles," *Chem. Commun.* 2621-2623, 2005.
Bean et al., "Lidocaine Block of Cardiac Sodium Channels," *J. Gen. Physiol.* 81: 613-642, May 1983.
Bennett and Xie, "A peripheral mononeuropathy in rat that produces disorders of pain sensation like those seen in man," *Pain* 33: 87-107, 1988.
Beyersbergen Van Henegouwen et al., "First Total Synthesis of *ent*-Gelsedine via a Novel Iodide-Promoted Allene N-Acyliminium Ion Cyclization," *J. Org. Chem.* 65(24): 8317-8325, 2000.
Beyersbergen Van Henegouwen et al., "Total Synthesis of (+)-Gelsedine," *Angw. Chem. Int. Ed.* 38(15): 2214-2217, 1999.
Billert and Beckert, "Beiträge zur Chemie der Pyrido[1,2-α]pyrazine—Reaktivität gegenüber Heterocumulenen der Kohlensäurereihe and Ketenen," *J. Prakt. Chem.* 341(4): 332-341, 1999.
Binder et al., "Disease mechanisms in neuropathic itch," *Nature Clinical Practice/ Neurology* 4(6): 329-337, Jun. 2008.
Blair and Bean, "Roles of Tetrodotoxin (TTX)-Sensitive $Na^+$ Current, TTX-Resistant $Na^+$ Current, and $Ca^{2+}$ Current in the Action Potentials of Nociceptive Sensory Neurons," *Journal of Neuroscience* 22(23): 10277-10290, Dec. 1, 2002.

Bond et al., "Cyclopiamines A and B, Novel Oxindole Metabolites of *Penicillium cyclopium* Westling," *Journal of the Chemical Society, Perkin Transaction 1: Organic and Bio-Organic Chemistry* 7: 1751-1761, 1979.
Brackenbury and Djamgoz, "Activity-dependent regulation of voltage-gated $Na^+$ channel expression in Mat-LyLu rat prostate cancer cell line," *J. Physiol.* 573.2: 343-356, 2006.
Bramson et al., "Oxindole-Based Inhibitors of Cyclin-Dependent Kinase 2 (CDK2): Design, Synthesis, Enzymatic Activities, and X-ray Crystallographic Analysis," *J. Med. Chem.* 44: 4339-4358, 2001.
Braude and Lindwall, "Condensations of Isatin with Acetone by the Knoevenagel Method," *Journal of the American Chemical Society* 55: 325-327, Jan. 1933.
Byrn et al., "Chapter 11, Hydrates and Solvates," in *Solid-State Chemistry of Drugs*, Second Edition, 1999, pp. 233-247.
Caldwell et al., "Sodium channel $Na_v1.6$ is localized at nodes of Ranvier, dendrites, and synapses," *PNAS* 97(10): 5616-5620, May 9, 2000.
Cañas-Rodriguez and Leeming, "N-Phenyl-2-indolinones and N-Phenylindolines. A New Class of Antidepressant Agents," *Journal of Medicinal Chemistry* 15(7): 762-770, 1972.
Capilla et al., "Synthesis of isoquinolines and tetrahydroisoquinolines as potential antitumour agents," *Tetrahedron* 57: 8297-8303, 2001.
Carlson et al., "Potential hypolipidemic agents: VI. Syntheses of some new halo-substituted pyridine compounds. Effects on noradrenaline-stimulated free fatty acid mobilization," *Acta Pharm. Suecica* 9: 411-418, 1972.
Cassebaum and Liedel, "Beziehungen zwischen Konstitution and α-Aminosäure-dehydrogenasewirkung von Isatinen," *Journal für praktische Chemie* 4(12):91-95, 1960.
Catterall, "Molecular mechanisms of gating and drug block of sodium channels," *2002 Sodium channels and neuronal hyperexcitability*, Wiley, Chichester (Novartis Foundation Symposium 241), p. 206-225.
Cestèle and Catterall, "Molecular mechanisms of neurotoxin action on voltage-gated sodium channels," *Biochimie* 82: 883-892, 2000.
Chande et al., "Facile synthesis of active antitubercular, cytotoxic and antibacterial agents: a Michael addition approach," *European Journal of Medicinal Chemistry* 40: 1143-1148, 2005.
Chaplan et al., "Quantitative assessment of tactile allodynia in the rat paw," *Journal of Neuroscience Methods* 53: 55-63, 1994.
Chioni et al., "A novel adhesion molecule in human breast cancer cells: Voltage-gated $Na^+$ channel β1 subunit," *The International Journal of Biochemistry & Cell Biology* 41: 1216-1227, 2009.
Chung and Chung, "Sodium channels and neuropathic pain," *Novartis Found Symposium* 261: 19-31, 2004.
Clare et al., "Voltage-gated sodium channels as therapeutic targets," *Drug Discovery Today* 5(11): 506-520, Nov. 2000.
Claudi et al., "Synthesis and Dopamine Receptor Affinities of 2-(4-Fluoro-3-hydroxyphenyl)ethylamine and N-Substituted Derivatives," *J. Med. Chem.* 33: 2408-2412, 1990.
Coppola, "N-Arylation of Isatins. A Direct Route to N-Arylisatoic Anhydrides," *J. Heterocyclic Chem.* 24: 1249-1251, Sep./Oct. 1987.
Cossy et al., "A Convenient Route to Spiropyrrolidinyl-Oxindole Alkaloids via C-3 Substituted Ene-Pyrrolidine Carbamate Radical Cyclization," *Tetrahedron Letters* 39: 2331-2332, 1998.
Cox et al., "An *SCN9A* channelopathy causes congenital inability to experience pain," *Nature* 444: 894-898, Dec. 14, 2006.
Craner et al., "Molecular changes in neurons in multiple sclerosis: Altered axonal expression of $Na_v1.2$ and $Na_v1.6$ sodium channels and $Na^+/Ca^{2+}$ exchanger," *PNAS* 101(21): 8168-8173, May 25, 2004.
Cravotto et al., "Azomethine Ylide Cycloaddition/Reductive Heterocyclization Approach to Oxindole Alkaloids: Asymmetric Synthesis of (—)-Horsfiline," *J. Org. Chem.* 66(25): 8447-8453, 2001.
Creveling and Daly, "Batrachotoxinin A [$^3$H]Benzoate Binding to Sodium Channels," *Methods in Neurosciences* 8: 25-37, 1992.
Cube et al., "3-(2-Ethoxy-4-{4-[3-hydroxy-2-methyl-4-(3-methylbutanoyl)-phenoxy]butoxy}phenyl)propanoic acid: a brain

(56) References Cited

OTHER PUBLICATIONS penetrant allosteric potentiator at the metabotropic glutamate receptor 2 (mGluR2)," *Bioorganic & Medicinal Chemistry Letters* 15: 2389-2393, 2005.

Dallacker and Sanders, "Darstellung und Reaktionen von 5-(3'-Hydroxy-oxindol-3'-y1)-1,3-benzdioxole," *Chemiker-Zeitung* 110(11): 405-411, 1986.

Devers and Galer, "Topical Lidocaine Patch Relieves a Variety of Neuropathic Pain Conditions: An Open-Label Study," *Clinical Journal* 16(3): 205-208, Sep. 2000, obtained from URL=http://ovidsp.tx.ovid.com/spb/ovidweb.cgi, download date Apr. 18, 2008, 5 pages.

Dib-Hajj et al., "Genetics and Molecular Pathophysiology of $Na_v1.7$-Related Pain Syndromes," *Advances in Genetics* 63: 85-110, 2008.

Dib-Hajj et al., "NaN, a novel voltage-gated Na channel, is expressed preferentially in peripheral sensory neurons and down-regulated after axotomy," *Proc. Natl. Acad. Sci. USA* 95: 8963-8968, Jul. 1998.

Dierks et al., "A Method for the Simultaneous Evaluation of the Activities of Seven Major Human Drug-Metabolizing Cytochrome P450S Using An In Vitro Cocktail of Probe Substrates and Fast Gradient Liquid Chromatography Tandem Mass Spectrometry," *Drug Metabolism and Disposition* 29(1): 23-29, 2001.

Ding et al., "Structure-Based Design of Spiro-oxindoles as Potent, Specific Small-Molecule Inhibitors of the MDM2-p53 Interaction," *J. Med. Chem* 49(12): 3432-3435, 2006.

Diss et al., "A potential novel marker for human prostate cancer: voltage-gated sodium channel expression in vivo," *Prostate Cancer and Prostatic Diseases* 8: 266-273, 2005.

Diss et al., "Expression Profiles of Voltage-Gated $Na^+$ Channel α-Subunit Genes in Rat and Human Prostate Cancer Cell Lines," *The Prostate* 48:165-178, 2001.

Diss et al., "Identification and characterization of the promoter region of the Nav1.7 voltage-gated sodium channel gene (*SCN9A*)," *Mol. Cell. Neurosci.* 37: 537-547, 2008.

Do and Bean, "Subthreshold Sodium Currents and Pacemaking of Subthalamic Neurons: Modulation by Slow Inactivation," *Neuron* 39: 109-120, Jul. 3, 2003.

Domingo et al., "Studies on the Biosynthesis of Paraherquamide A and VM99955. A Theoretical Study of Intramolecular Diels—Alder Cycloaddition," *J. Org. Chem.* 68(7): 2895-2902, 2003.

Doyle et al., "Rhodium (II) Acetate and Nafion-H Catalyzed Decomposition of *N*-Aryldiazoamides. An Efficient Synthesis of 2(3*H*)-Indolinones," *J. Org. Chem* 53(5): 1017-1022, 1988.

Dubuisson and Dennis, "The Formalin Test: A Quantitative Study of the Analgesic Effects of Morphine, Meperidine, and Brain Stem Stimulation in Rats and Cats," *Pain* 4: 161-174, 1977.

Dutton et al., "A Total Synthesis of Gelsemine. Oxindole Spiroannelation," *J. Chem. Soc., Chem. Commun.* 765-766, 1994.

Dutton et al., "Synthesis of Hindered Spiro-Oxindoles by Photolysis of 1-(1-Alkenyl)benzotriazoles," *Tetrahedron* 55: 11927-11942, 1999.

El-Ahl, "Three-Component 1,3-Dipolar Cycloaddition Reactions in Synthesis of Spiro[pyrrolidine-2,3'-oxindoline] Derivatives," *Heteroatom Chemistry* 13(4): 324-329, 2002.

El-Gendy and Ahmedy, "Synthesis and Antimicrobial Activity of some New 2-Indolinone Derived Oximes and Spiro-Isoxazolines," *Arch. Pharm. Res.* 23(4): 310-314, 2000.

Ettinger and Argoff, "Use of Antiepileptic Drugs for Nonepileptic Conditions: Psychiatric Disorders and Chronic Pain," *Neurotherapeutics: The Journal of the American Society for Experimental Neuro Therapeutics* 4:75-83, Jan. 2007.

Feldman and Karatjas, "Extending Pummerer Reaction Chemistry. Asymmetric Synthesis of Spirocyclic Oxindoles via Chiral Indole-2-sulfoxides," *Org. Lett.* 8(18): 4137-4140, 2006.

Feldman and Vidulova, "Extending Pummerer Reaction Chemistry. Application to the Oxidative Cyclization of Indole Derivatives," *Organic Letters* 6(11): 1869-1871, 2004.

Fishman et al., "Intravenous Lidocaine for Treatment-resistant Pruritus," *American Journal of Medicine* 102: 584-585, Jun. 1997.

Flanagan et al., "Radical cyclisation reactions with indoles," *Tetrahedron Letters* 44: 1795-1798, 2003.

Fokas et al., "Solution Phase Synthesis of a Spiro[pyrrolidine-2,3'-oxindole] Library via a Three Component 1,3-Dipolar Cycloaddition Reaction," *Tetrahedron Letters* 39: 2235-2238, 1998.

Foster et al., "457. Furano-compounds. Part VII. A Synthesis of 2 : 3-Dihydropsoralene," *J. Chem. Soc.* 2254-2260, 1948.

Fraser et al., "Voltage-Gated Sodium Channel Expression and Potentiation of Human Breast Cancer Metastasis," *Clin. Cancer Res.* 11(15): 5381-5389, Aug. 1, 2005.

Fuchs and Funk, "Indol-2-one Intermediates: Mechanistic Evidence and Synthetic Utility. Total Syntheses of (±)-Flustramines A and C," *Org. Lett.* 7(4): 677-680, 2005.

Fuchs and See, "Basolateral amygdala inactivation abolishes conditioned stimulus- and heroin-induced reinstatement of extinguished heroin-seeking behavior in rats," *Psychopharmacology* 160: 425-433, 2002.

Fuji et al., "Direct Asymmetric Synthesis of Quaternary Carbon Centers via Addition-Elimination Process: Nitroolefination of α-Substituted δ-Lactones," *J. Am. Chem. Soc.* 111: 7921-7925, 1989.

Fujita et al., "The Beckmann Rearrangement by Means of Phosphoryl Chloride/*N,N*-Dimethylacetamide; A Novel and Convenient Method for Preparing Benzoxazoles," *Synthesis* 68-69, Jan. 1982.

Gálvez and García, "Synthesis of Isomeric β-Haloethylthienopyrroles," *J. Heterocyclic Chem.* 21: 393-395, Mar.-Apr. 1984.

Ganguly et al., "Solution- and solid-phase synthesis of enantiomerically pure spiro oxindoles," *Tetrahedron Letters* 43: 8981-8983, 2002.

Ganguly et al., "Synthesis of heterocyclic compounds using radical reactions and evidence for the formation of spiro radical intermediates," *Tetrahedron Letters* 45: 883-886, 2004. See also Ganguly et al., "Corrigendum to 'Synthesis of heterocyclic compounds using radical reactions and evidence for the formation of spiro radical intermediates,'" [*Tetrahedron Letters* 45: 883-886, 2004], *Tetrahedron Letters* 45: 3835, 2004.

Garden et al., "A versatile synthetic methodology for the synthesis of tryptophols," *Tetrahedron* 58: 8399-8412, 2002.

Garden et al., "Investigation of the selective reduction of isatin derivatives. Synthesis of α-hydroxyacetophenone derivatives and ethyl *spiro*-3,3-(ethylenedioxy)-2-hydroxyindohne carboxylates," *Tetrahedron Letters* 44: 7617-7621, 2003.

Goldberg et al., "Loss-of-function mutations in the $Na_v1.7$ gene underlie congenital indifference to pain in multiple human populations," *Clin. Genet.* 71: 311-319, 2007.

Goldberg, "The Significance of Molecular Type, Shape and Complementarity in Clathrate Inclusion," *Topics in Current Chemistry* 149: 1-44, 1988.

González-López de Turiso and Curran, "Radical Cyclization Approach to Spirocyclohexadienones," *Organic Letters* 7(1): 151-154, 2005.

Grigg et al., "Palladium Catalysed Ter- and Tetra-molecular Queuing Processes. One-pot Routes to 3-Spiro-2-Oxindoles and 3-Spiro-2(3H)-Benzofuranones," *Tetrahedron Letters* 37(5): 695-698, 1996.

Grigg et al., "Spiro-oxindoles via bimetallic [Pd(0)/Ag(I)] catalytic intramolecular Heck-1,3-dipolar cycloaddition cascade reactions," *Tetrahedron Letters* 43: 2605-2608, 2002.

Grigoryan et al., "Synthesis and antispasmodic activity of spiron[β-carbolineindolones] and spiro[indoleindolo[2,3-c]azepinones]," *Hayastani Kimiakan Handes* 58(3): 100-104, 2005, CAPLUS Database Accession No. 2005:876436, 4 pages, Abstract only.

Guillaumet et al., "Synthese d'un analogue dioxinique du psoralene," *Tetrahedron Letters* 29(22): 2665-2666, 1988.

Hains et al., "Upregulation of Sodium Channel $Na_v1.3$ and Functional Involvement in Neuronal Hyperexcitability Associated with Central Neuropathic Pain after Spinal Cord Injury," *Journal of Neuroscience* 23(26): 8881-8892, Oct. 1, 2003.

Hamann et al., "Motor disturbances in mice with deficiency of the sodium channel gene *Scn8a* show features of human dystonia," *Experimental Neurology* 184: 830-838, 2003.

(56) References Cited

OTHER PUBLICATIONS

Haufe et al., "The promiscuous nature of the cardiac sodium current," *Journal of Molecular and Cellular Cardiology* 42: 469-477, 2007.
Hiemstra et al., "Models of Folate Coenzymes—VIII: An Approach to Yohimbane Alkaloids Via Carbon-Fragment Transfer From $N^5$, $N^{10}$-Methylenetetrahydrofolate Models," *Tetrahedron* 39(23): 1981-1986, 1983.
Hille, "Local Anesthetics: Hydrophilic and Hydrophobic Pathways for the Drug-Receptor Reaction," *The Journal of General Physiology* 69: 497-515, 1977.
Hille, "The pH-Dependent Rate of Action of Local Anesthetics on the Node of Ranvier," *The Journal of General Physiology* 69: 475-496, 1977.
Hoffman, *Organic Chemistry: An Intermediate Text—Second Edition*, John Wiley & Sons, Inc., Hoboken, New Jersey, 2004, 124, 138-144.
Ikoma et al., "The neurobiology of itch," *Nature Reviews Neuroscience* 7: 535-547, Jul. 2006.
Ikoma et al., "Neuronal Sensitization for Histamine-Induced Itch in Lesional Skin of Patients With Atopic Dermatitis," *Arch Dermatol.* 139: 1455-1458, Nov. 2003.
Inan et al , "Inhibitory effect of lidocaine on pain and itch using formalin-induced nociception and 5'-guanidinonaltrindole-induced scratching models in mice: Behavioral and neuroanatomical evidence," *European Journal of Pharmacology* 616: 141-146, 2009.
Iranpoor et al., "A novel method for the highly efficient synthesis of 1,2-benzisoxazoles under neutral conditions using the $Ph_3P/DDQ$ system," *Tetrahedron Letters* 47: 8247-8250, 2006.
Ishiyama et al., "Synthesis of Arylboronates via the Palladium(0)-Catalyzed Cross-Coupling Reaction of Tetra(alkoxo)diborons with Aryl Triflates," *Tetrahedron Letters* 38(19): 3447-3450, 1997.
Islip and White, "236. Some Reactions of 2-(3-Oxindolyl)ethylamines," *Journal of the Chemical Society* 1201-1204, 1964.
Itoh et al., "Introduction of a Hydroxy Group at the Para Position and N-Iodophenylation of N-Arylamides Using Phenyliodine(III) Bis(Trifluoracetate)," *J. Org. Chem.* 67: 7424-7428, 2002.
Jarvis et al., "A-803467, a potent and selective $Na_v1.8$ sodium channel blocker, attenuates neuropathic and inflammatory pain in the rat," *PNAS* 104(20): 8520-8525, May 15, 2007.
Jorgensen and Berteau, "Thyroxine Analogs. 21. *o*- and *m*-L-Thyroxine and Related Compounds," *Journal of Medicinal Chemistry* 14(12): 1199-1202, 1971.
Julian et al., "Studies in the Indole Series. VI. On the Synthesis of Oxytryptophan and Further Studies of 3-Alkylation of Oxindoles," *Journal of the American Chemical Society* 57: 2026-2029, Nov. 1935.
Julian et al., "Studies in the Indole Series. VIII. Yohimbine (Part 1). The Mechanism of Dehydrogenation of Yohimbine and Related Compounds," *Journal of the American Chemical Society* 70: 174-179, Jan. 1948.
Kaila et al., "Synthesis and Biological Evaluation of Quinoline Salicylic Acids as P-Selectin Antagonists," *J. Med. Chem.* 50: 21-39, 2007.
Kamara et al., "The First Direct Transformation of 2,2'-Dihydroxychalcones into Coumestans," *Tetrahedron* 55: 861-868, 1999.
Kamiya et al., "A Nonsense Mutation of the Sodium Channel Gene SCN2A in a Patient with Intractable Epilepsy and Mental Decline," *Journal of Neuroscience* 24(11): 2690-2698, Mar. 17, 2004.
Kang et al., "Pteropodine and isopteropodine positively modulate the function of rat muscarinic $M_1$ and $5-HT_2$ receptors expressed in Xenopus oocyte," *European Journal of Pharmacology* 444: 39-45, 2002.
Karp et al., "Preparation of 4-Hydroxy-2-trifluoromethylthiophene: A Novel Bioisostere of $\alpha,\alpha,\alpha$-Trifluoro-*m*-cresol," *Synthesis* 8: 1078-1080, 2000.
Kende et al., "Intramolecular Radical Cyclization of Phenolic Enolates," *J. Am. Chem. Soc.* 110: 2210-2218, 1988.

Kim et al., "BACE1 regulates voltage-gated sodium channels and neuronal activity," *Nature Cell Biology* 9(7): 755-764, Jul. 2007.
Kim et al., "Design, synthesis, and evaluation of dioxane-based antiviral agents targeted against the Sindbis virus capsid protein," *Bioorganic & Medicinal Chemistry Letters* 15: 3207-3211, 2005.
King et al., "Hydroxy-quinoxalines and -phenazines, and Experiments on the Preparation of Hydroxyquinoxaline Di-*N*-oxides," *J. Chem. Soc.* 3012-3016, 1949.
Kirmse et al., "Intramolecular Reactivity of Arylcarbenes: Derivatives of *o*-Tolylcarbene," *J. Org. Chem.* 59: 3821-3829, 1994.
Kis-Toth et al., "Voltage-Gated Sodium Channel Nav1.7 Maintains the Membrane Potential and Regulates the Activation and Chemokine-Induced Migration of a Monocyte-Derived Dendritic Cell Subset," *The Journal of Immunology* 187: 1273-1280, 2011.
Klugbauer et al., "Structure and functional expression of a new member of the tetrodotoxin-sensitive voltage-activated sodium channel family from human neuroendocrine cells," *EMBO J.* 14(6): 1084-1090, 1995.
Kobayashi and Furukawa, "Studies on Indole Derivatives. I. Synthesis of 3-Phenyl-9*H*-pyridazino-[3,4-*b*]indole Derivatives," *Chemical & Pharmaceutical Bulletin* 12(10): 1129-1135, Oct. 1964.
Kollmar et al., "2-Amino-3-Fluorobenzoic Acid [Benzoic acid, 2-amino-3-fluoro-]," *Organic Syntheses, Coll.* 79: 196, 2002, 5 pages.
Kornet and Thio, "Oxindole-3-spiropyrrolidines and -piperidines. Synthesis and Local Anesthetic Activity," *Journal of Medicinal Chemistry* 19(7): 892-898, 1976.
Kotha et al., "Recent applications of the Suzuki-Miyaura cross-coupling reaction in organic synthesis," *Tetrahedron* 58: 9633-9695, 2002.
Kubo et al., "Michael Additions of Indoles to 2-oxoindolin-3-ylidene Ketones," *Heterocycles* 4(10), 1675-1680, 1976.
Kumar et al., "A New Route to Spiropyrrolidinyl-oxindole Alkaloids via Iodide Ion Induced Rearrangement of [(*N*-Aziridinomethylthio)methylene]-2-oxindoles," *Organic Letters* 3(26): 4193-4196, 2001.
Kuzma et al., "Progress in the Development of Ultra-Long-Acting Local Anesthetics," *Regional Anesthesia* 22(6): 543-551, Nov.-Dec. 1997.
Lackey and Sternbach, "Synthesis of Substituted Quinoline-4-carboxylic Acids," *Synthesis*: 993-997, Oct. 1993.
Lai et al., "The role of voltage-gated sodium channels in neuropathic pain," *Current Opinion in Neurobiology* 13:291-297, 2003.
Lange et al., "Regioselective Aminomethylations of Bicyclic Phenols," *Heterocycles* 53(1): 197-204, 2000.
Laniado et al., "Short Communication: Expression and Functional Analysis of Voltage-Activated $NA^+$ Channels in Human Prostate Cancer Cell Lines and their Contribution to Invasion in Vitro," *American Journal of Pathology* 150(4): 1213-1221, Apr. 1997.
Laus et al., "Analysis of the kinetics of isomerization of spiro oxindole alkaloids," *J. Chem. Soc., Perkin Trans.* 2: 1931-1936, 1996.
Laus, "Kinetics of isomerization of tetracyclic spiro oxindole alkaloids," *J. Chem. Soc., Perkin Trans.* 2: 315-317, 1998.
Le Bourdonnec et al., "Medicinal Chemistry Strategies to Reduce CYP2D6 Inhibitory Activity of Lead Candidates," *Current Medicinal Chemistry* 16: 3093-3121, 2009.
Lee-Son et al., "Stereoselective Inhibition of Neuronal Sodium Channels by Local Anesthetics," *Anesthesiology* 77: 324-335, 1992.
Lerchner and Carreira, "Synthesis of (±)-Strychnofoline via a Highly Convergent Selective Annulation Reaction," *Chem. Eur. J.* 12: 8208-8219, 2006.
Leuwer et al., "An improved model for the binding of lidocaine and structurally related local anaesthetics to fast-inactivated voltage-operated sodium channels, showing evidence of cooperativity," *British Journal of Pharmacology* 141(1): 47-54, 2004.
Li et al., "A case of primary erythermalgia with prurigo," *Clinical and Experimental Dermatology* 34: e313-e314, 2009.
Lindemann et al., "Zur Kenntnis der Indoxazene," *Justus Liebigs Annalen der Chemie* 456: 284-311, 1927.

(56) References Cited

OTHER PUBLICATIONS

Lindwall and Maclennan, "A Condensation of Acetophenone with Isatin by the Knoevenagel Method," *Journal of the American Chemical Society* 54: 4739-4744, Dec. 1932.
Liu et al., "Mutations in Cardiac Sodium Channels: Clinical Implications," *Am. J. Pharmacogenomics* 3(3): 173-179, 2003.
Lorenz et al., "Binary and ternary phase diagrams of two enantiomers in solvent systems," *Thermochimica Acta* 382: 129-142, 2002.
Lossin et al., "Molecular Basis of an Inherited Epilepsy," *Neuron* 34: 877-884, Jun. 13, 2002.
Loudon and Ogg, "2:3-Dihydro-3-oxobenz-1:4-oxazines," *J. Chem. Soc.*: 739-744, 1955.
Lutz and Clark, "Acid-Catalyzed Rearrangements of the γ-(Methylanilino)lactone of cis-β-p-Bromobenzoyl)-β-methylacrylic Acid, and of trans-β-(p-Bromobenzoyl)acrylic Methylanilide, to Oxindoles," *J. Org. Chem.* 25: 193-196, Feb. 1960.
Lyalin et al., [title unavailable], *Zhurnal Organicheskoi Khimii* 20(4): 846-849, 1984.
Ma and Cai, "N,N-Dimethyl Glycine-Promoted Ullmann Coupling Reaction of Phenols and Aryl Halides," *Organic Letters* 5(21): 3799-3802, 2003.
MacNicol, "Clathrates and Molecular Inclusion Phenomena," *Chemical Society Reviews* 7(1): 65-87, 1978.
Maercker and Theysohn, "Versuche zur Umlagerung von 2-Cyclopropyl-äthyl-Anionen," *Liebigs Ann. Chem.* 759: 132-157, 1972.
Maginnity and Gaulin, "Derivatives of o-, m- and p-Aminobenzotrifluoride," *J. Am. Chem. Soc.* 73: 3579-3580, Aug. 1951.
Majumdar et al., "1-Alkylisatins via Aldol-Retro-aldol Condensation," *J. Chem. Research (S)*, 460-461, 1996.
Mann et al., "The Synthesis of Lignans and Related Structures using Quinodimethanes and Isobenzofurans: Approaches to the Podophyllins," *J. Chem. Soc. Perkin Trans. I*: 2081-2088, 1984.
Mannaioni et al., "Tryptophan Metabolism and Hepatic Encephalopathy. Studies on the Sedative Properties of Oxindole," *Advances in experimental medicine and biology* 467: 155-167, 1999.
Mao and Baldwin, "New Spirocyclic Oxindole Synthesis Based on a Hetero Claisen Rearrangement," *Organic Letters* 6(14): 2425-2428, 2004.
Mao and Chen, "Systemic lidocaine for neuropathic pain relief," *Pain* 87: 7-17, 2000.
Marcantonio et al., "An Investigation into Causes and Effects of High Cyanide Levels in the Palladium-Catalyzed Cyanation Reaction," *Organic Letters* 6(21): 3723-3725, 2004.
Marti and Carreira, "Construction of Spiro[pyrrolidine-3,3'-oxindoles]—Recent Applications to the Synthesis of Oxindole Alkaloids," *Eur. J. Org. Chem.* 2209-2219, 2003.
Marti and Carreira, "Total Synthesis of (—)-Spirotryprostatin B: Synthesis and Related Studies," *J. Am. Chem. Soc.* 127(32): 11505-11515, 2005.
McMurtrey and Daves, Jr., "König's Adducts of N-Alkyl(aryl)aminoethanols and Quinones. 3,4-Dihydro-4-alkyl(aryl)-8a-hydroxy-2H-1,4,benzoxazin-6(8aH)-ones," *J. Org. Chem.* 35(12): 4252-4253, 1970.
McNeal et al., "[$^3$H]Batrachotoxinin A 20α-Benzoate Binding to Voltage-Sensitive Sodium Channels: A Rapid and Quantitative Assay for Local Anesthetic Activity in a Variety of Drugs," *J. Med. Chem.* 28(3): 381-388, 1985.
Meisler et al., "Sodium channel gene family: epilepsy mutations, gene interactions and modifier effects," *J. Physiol.* 588.11: 1841-1848, 2010.
Miyake et al., "Preparation and Synthetic Applications of 2-Halotryptamines: Synthesis of Elacomin and Isoelacomine," *Organic Letters* 6(5): 711-713, 2004.
Miyamoto et al., "Highly Diastereoselective One-Pot Synthesis of Spirocyclic Oxindoles through Intramolecular Ullmann Coupling and Claisen Rearrangement," *Angew. Chem. Int. Ed.* 45: 2274-2277, 2006.

Miyaura and Suzuki, "Palladium-Catalyzed Cross-Coupling Reactions of Organoboron Compounds," *Chem. Rev.* 95: 2457-2483, 1995.
Morie et al., "Asymmetric Synthesis of the Enantiomers of 2-Aminomethyl-4-(4-Fluorobenzyl)morpholine, an Intermediate of Mosapride, a Gastroprokinetic Agent," *Heterocycles* 38(5): 1033-1040, 1994.
Morinville et al., "Distribution of the Voltage-Gated Sodium Channel Na$_v$1.7 in the Rat: Expression in the Autonomic and Endocrine Systems," *Journal of Comparative Neurology* 504: 680-689, 2007.
Morton et al., "Novel solid-phase synthesis of 1,5-benzothiazepine-4-one derivatives," *Tetrahedron Letters* 41: 3029-3033, 2000.
Muci and Buchwald, "Practical Palladium Catalysts for C—N. And C—O Bond Formation," *Topics in Current Chemistry* 219: 131-209, 2002.
Muhammad et al., "Two stereoisomeric pentacyclic oxindole alkaloids from *Uncaria tomentosa*; uncarine C and uncarine E," *Acta Cyst.* C57: 480-482, 2001.
Nagakura et al., "Allodynia and Hyperalgesia in Adjuvant-Induced Arthritic Rats: Time Course of Progression and Efficacy of Analgesics," *The Journal of Pharmacology and Experimental Therapeutics* 306(2): 490-497, 2003, obtained from URL=http://jpet.aspetjournals.org, download date Aug. 14, 2009.
Nagamura and Saito, "Antitumor Antibiotics: Duocarmycins," *Chemistry of Heterocyclic Compounds* 34(12): 1386-1405, 1998.
Nagamura et al., "Wagner-Meerwein Rearrangement of Duocarmycins," *Chem. Pharm. Bull.* 44(5): 933-939, May 1996.
Nair et al., "Formal dipolar cycloaddition of allylsilanes to o-quinonoid compounds: a convenient route to benzofused and spirofused heterocycles," *Tetrahedron Letters* 43: 5349-5351, 2002.
Nair et al., "N-Heterocyclic Carbene Catalyzed Reaction of Enals and 1,2-Dicarbonyl Compounds: Stereoselective Synthesis of Spiro γ-Butyrolactones," *Org. Lett.* 8(3): 507-509, 2006.
Nakamura et al., "Cancer preventive agents, Part 2: Synthesis and evaluation of 2-phenyl-4-quinolone and 9-oxo-9,10-dihydroacridine derivatives as novel antitumor promoters," *Bioorganic & Medicinal Chemistry* 13: 4396-4401, 2005.
Namer et al., "Separate Peripheral Pathways for Pruritus in Man," *J. Neurophysiol.* 100: 2062-2069, 2008.
Newkome et al., "β-Methyl Functionalization of Electron-Poor Heterocycles: Free Radical Chlorination," *Synthesis* 676-679, Aug. 1984.
Nicolaus, *Decision Making in Drug Research*, Raven Press, New York, 1983, Franz Gross (ed.), "Symbiotic Approach to Drug Design," pp. 173-186.
Niemann et al., "The Synthesis of 3'-Fluoro-*dl*-thyronine and Some of its Iodinated Derivatives," *J. Am. Chem. Soc.* 63: 609-611, Feb. 1941.
Oaklander et al., "Intractable postherpetic itch and cutaneous deafferentation after facial shingles," *Pain* 96: 9-12, 2002.
Oguri et al., "Amino Acids and Peptides. XXVIII. A New Synthesis of β-Amino Acid Derivatives by Alkylation of Schiff Bases derived from Glycine and Alanine," *Chem. Pharm. Bull.* 25(9): 2287-2291, 1977.
Okita and Isobe, "Synthesis of the Pentacyclic Intermediate for Dynemicin A and Unusual Formation of Spiro-oxindole Ring," *Tetrahedron* 50(38): 11143-11152, 1994.
Onishi et al., "Concise, Asymmetric Total Synthesis of Spirotryprostatin A," *Organic Letters* 5(17): 3135-3137, 2003.
Onishi et al., "Concise, asymmetric total synthesis of spirotryprostatin A," *Tetrahedron* 60: 9503-9515, 2004.
Orlova et al., "Synthesis of 2,3,4,5-Tetrahydro-1,5-Benzox(and Thi)azepines and Their Utilization For the Preparation of Condensed Indoles," Translated from *Khimiya Geterotsiklicheskikh Soedinenii* 9: 1262-1266, Sep. 1975, 5 pages.
Overman and Watson, "Diastereoselection in the Formation of Spirocyclic Oxindoles by the Intramolecular Heck Reaction," *J. Org. Chem* 71: 2587-2599, 2006.
Papale et al., "Heterozygous mutations of the voltage-gated sodium channel *SCN8A* are associated with spike-wave discharges and absence epilepsy in mice," *Human Molecular Genetics* 18(9): 1633-1641, 2009.

(56) References Cited

OTHER PUBLICATIONS

Patani and LaVoie, "Bioisosterism: A Rational Approach in Drug Design," *Chem. Rev.* 96(8): 3147-3176, 1996.

Pearn, "Neurology of ciguatera,"*J.Neurol. Neurosurg. Psychiatry* 70: 4-8, 2001.

Pereira et al., "Severe epilepsy, retardation, and dysmorphic features with a 2q deletion including SCN1A and SCN2A," *Neurology* 63: 191-192, 2004.

Pietra and Tacconi, "α-Alkyl- and α-aryl-N-methyltryptamines," *Farmaco, Edizione Scientifica* 14: 854-866, 1959, CAPLUS Database Accession No. 1960:50362, 1 page, Abstract only.

Popp and Pajouhesh, "Potential Anticonvulsants IV: Condensation of Isatin with Benzoylacetone and Isopropyl Methyl Ketone," *Journal of Pharmaceutical Sciences* 71(9): 1052-1054, Sep. 1982.

Popp et al., "Synthesis of Potential Anticonvulsants: Consensation of Isatins with Acetone and Related Ketones," *Journal of Pharmaceutical Sciences* 69(10): 1235-1237, Oct. 1980.

Popp, "Potential Anticonvulsants. V. The Condensation of Isatins with C-Acetyl Heterocyclic Compounds," *J. Heterocyclic Chem.* 19: 589-592, May-Jun. 1982.

Pouton, "Lipid formulations for oral administration of drugs: non-emulsifying, self-emulsifying and 'self-microemulsifying' drug delivery systems," *European Journal of Pharmaceutical Sciences* 11(Suppl 2): S93-S98, 2000.

Priest, "Future potential and status of selective sodium channel blockers for the treatment of pain," *Current Opinion in Drug Discovery & Development* 12(5): 682-692, 2009.

Puopolo et al., "Roles of Subthreshold Calcium Current and Sodium Current in Spontaneous Firing of Mouse Midbrain Dopamine Neurons," *Journal of Neuroscience* 27(3): 645-656, Jan. 17, 2007.

Raj and Raghunathan, "A Novel Entry into a New Class of Spiro Heterocyclic Framework: A Facile Synthesis of Dispiro[oxindole-1,2,3,4-tetrahydro-naphthalen-1-one]pyrrolidines and Spiro[1,2,3,4-tetrahydro-naphthalen-1-one]pyrrolidines," *Synthetic Communications* 33(7):1131-1139, 2003.

Raj and Raghunathan, "A novel entry into a new class of spiroheterocyclic framework: regioselective synthesis of dispiro[oxindole-cyclohexanone]-pyrrolidines and dispiro[oxindole-hexahydroindazole]pyrrolidines," *Tetrahedron* 57: 10293-10298, 2001.

Raj et al., "Synthesis, Antimicrobial and Antifungal Activity of a New Class of Spiro Pyrrolidines," *Bioorganic & Medicinal Chemistry* 11: 407-419, 2003.

Raymond et al., "Expression of Alternatively Spliced Sodium Channel α-Subunit Genes," *Journal of Biological Chemistry* 279(44): 46234-46241, Oct. 29, 2004.

Reddy et al., "Synthesis and Pharmacological Evaluation of N,N-Diarylguanidines as Potent Sodium Channel Blockers and Anticonvulsant Agents," *J. Med. Chem.* 41(17): 3298-3302, 1998.

Rehn et al., "The Three-Component Reaction between Isatin, α-Amino Acids, and Dipolarophiles," *Eur. J. Org. Chem.* 413-418, 2004.

Reimann et al., "Pain perception is altered by a nucleotide polymorphism in SCN9A," *PNAS* 107(11): 5148-5153, Mar. 16, 2010.

Ren and Dubner, "Enhanced Descending Modulation of Nociception in Rats With Persistent Hindpaw Inflamation," *Journal of Neurophysiology* 76(5): 3025-3037, Nov. 1996.

Rhodes et al., "Noninactivating voltage-gated sodium channels in severe myoclonic epilepsy of infancy," *PNAS* 101(30): 11147-11152, Jul. 27, 2004.

Rivalle and Bisagni, "Ethyl (4-N-Acylaminopyridin-3-yl)glyoxylate and 5-Azaisatin as New Synthons for a Route to Various New Polyheterocycles," *J. Heterocyclic Chem.* 34: 441-444, Mar.-Apr. 1997.

Rosevear and Wilshire, "Cyclization Reactions in Azole Chemistry: The Reaction of Some Azoles with o-Fluoro-acetophenone, o-Fluorobenzaldehyde and o-Fluorobenzophenone," *Aust. J. Chem.* 44: 1097-1114, 1991.

Ross et al., "Loss of Inhibitory Interneurons in the Dorsal Spinal Cord and Elevated Itch in Bhlhb5 Mutant Mice," *Neuron* 65: 886-898, Mar. 25, 2010.

Rossiter, "A convenient synthesis of 3-methyleneoxindoles: cytotoxic metabolites of indole-3-acetic acids," *Tetrahedron Letters* 43: 4671-4673, 2002.

Ruan et al., "Sodium channel mutations and arrhythmias," *Nature Reviews Cardiology* 6: 337-348, May 2009.

Sadler, "Separation of Isomeric Isatins," *J. Org. Chem.* 21(2): 169-170, 1956.

Saenger, "Cyclodextrin Inclusion Compounds in Research and Industry," *Angew. Chem. Int. Ed. Engl* 19: 344-362, 1980.

Sakaki et al., "Discovery of IRL 3461: A Novel and Potent Endothelin Antagonist With Balanced $ET_A/ET_B$ Affinity," *Biooganic & Medicinal Chemistry Letters* 8: 2241-2246, 1998.

Sauviat et al., "Blockade of sodium channels by Bistramide A in voltage-clamped frog skeletal muscle fibres," *Biochimica et Biophysica Acta* 1103: 109-114, 1992.

Sawyer, "Recent Advances in Diaryl Ether Synthesis," *Tetrahedron* 56: 5045-5065, 2000.

Schmelz et al., "Specific C-Receptors for Itch in Human Skin," *The Journal of Neuroscience* 17(20): 8003-8008, Oct. 15, 1997.

Schnyder et al., "Synthesis of Primary Aromatic Amides by Aminocarbonylation of Aryl Halides Using Formamide as an Ammonia Synthon," *J. Org. Chem.* 66: 4311-4315, 2001.

Schulenburg and Archer, "An Unusual Base-catalyzed Cyclization," *Journal of the American Chemical Society* 83(14): 3091-3096, Jul. 20, 1961.

Sebahar et al., "Asymmetric, stereocontrolled total synthesis of (+) and (—)-spirotryprostatin B via a diastereoselective azomethine glide [1,3]-dipolar cycloaddition reaction," *Tetrahedron* 58: 6311-6322, 2002.

Shin et al., "Potent inhibition of CYP2D6 by haloperidol metabolites: stereoselective inhibition by reduced haloperidol," *J. Clin. Pharmacol.* 51: 45-52, 2001.

Shoop et al., "Anthelmintic Activity of Paraherquamide in Sheep," *J. Parasitol.* 76(3): 349-351, Jun. 1990.

Simas et al., "Regioselective Lithiation of Resorcinol Derivatives: Synthesis of Mono O-MOM- and O-Benzylresorcinols Prenylated at C-2 or C-4 Positions," *Synthesis* 6: 1017-1021, 1999.

Singh et al., "Novel cAMP PDE III Inhibitors: Imidazo[4,5-b]pyridine-2(3H)-ones and Thiazolo[4,5-b]pyridin-2(3H)-ones and Their Analogs," *J. Med. Chem.* 37: 248-254, 1994.

Sircar et al., "Synthesis and SAR of N-Benzoyl-1-Biphenylalanine Dervatives: Discovery of TR-14035, A Dual $\alpha_4\beta_7/\alpha_4\beta_1$ Integrin Antagonist," *Bioorganic & Medicinal Chemistry Letters* 10: 2051-2066, 2002.

Smith et al., "Sodium channel protein expression enhances the invasiveness of rat and human prostate cancer cells," *FEBS Letters* 423: 19-24, 1998.

Sridhar and Raghunathan, "Rapid Access for the Synthesis of 1-N-Methyl-spiro[2.3']oxindole-spiro[3.7"] (3"-Aryl)-5"-methyl-3",3a",4",5",6",7"-hexahydro-2H-pyrazolo[4,3-c]pyridine-4-aryl-pyrrolidines Through Sequential 1,3-Dipolar Cycloaddition and Annulation," *Synthetic Communications* 36: 21-29, 2006.

Steinhoff et al., "Proteinase-Activated Receptor-2 Mediates Itch: A Novel Pathway for Pruritus in Human Skin," *Journal of Neuroscience* 23(15): 6176-6180, Jul. 16, 2003.

Stella and NTI-Addae, "Prodrug strategies to overcome poor water solubility," *Advanced Drug Delivery Reviews* 59: 677-694, 2007.

Subramaniyan et al., "A facile entry into a new class of spiroheterocycles: synthesis of dispiro[oxindolechromanone/flavanone/tetralone]pyrroloisoquinoline ring systems," *Tetrahedron* 58: 9075-9079, 2002.

Suchý et al., "Synthesis, Absolute Configuration, and Enantiomeric Enrichment of a Cruciferous Oxindole Phytoalexin, (S)-(—)-Spirobrassinin, and Its Oxazoline Analog," *J. Org. Chem.* 66: 3940-3947, 2001.

Tacconi et al., "Heterodiene Syntheses—V 1,2-versus 1,4-cycloaddition reactions of enamines to n-substituted 3-oxindolideneacetopheones," *Tetrahedron* 27: 561-579, 1971.

Takahashi et al., "Palladium(0)-Catalyzed Carbonylation on the Multipin™ System," *Tetrahedron Letters* 40: 7843-7846, 1999.

(56) References Cited

OTHER PUBLICATIONS

Tamaoka, "Paramyotonia Congenita and Skeletal Sodium Channelopathy," *Internal Medicine* 42(9): 769-770, Sep. 2003.
Tanelian and Brose, "Neuropathic Pain Can Be Relieved by Drugs That Are Use-dependent Sodium Channel Blockers: Lidocaine, Carbamazepine, and Mexiletine," *Anesthesiology* 74(5): 949-951, May 1991.
Ting et al., "Substituted 1,3-Dihydro-2*H*-pyrrolo[2,3-*b*]pyridin-2-ones as Potential Antiinflammatory Agents," *J. Med. Chem.* 33(10): 2697-2706, 1990.
Tokunaga et al., "Oxindole Derivatives as Orally Active Potent Growth Hormone Secretagogues," *J. Med. Chem.* 44(26): 4641-4649, 2001.
Trost and Brennan, "Palladium Asymmetric Allylic Alkylation of Prochiral Nucleophiles: Horsfiline," *Org. Lett.* 8(10): 2027-2030, 2006.
Trost and Frederiksen, "Palladium-Catalyzed Asymmetric Allylation of Prochiral Nucleophiles: Synthesis of 3-Allyl-3-Aryl Oxindoles," *Angew. Chem. Int. Ed.* 44: 308-310, 2005.
Twycross et al., "Itch: scratching more than the surface," *Q. J. Med.* 96: 7-26, 2003.
Usman et al., "1-Acetyl-3-(2-chloro-2,3-dihydrobenzofuran-3-y1)-1,2-dihydro-3-hydroxy-2-oxo-3*H*-indole," *Acta Cryst.* E58: o37-o39, 2002.
Venkatesan et al., "Total Synthesis of SR 121463 A, a Highly Potent and Selective Vasopressin $V_2$ Receptor Antagonist," *Journal of Organic Chemistry* 66(11): 3653-3661, Jun. 1, 2001.
Viaud et al., "Pyrrolo[2,3-*b*]pyridin-2(2*H*)-one Derivatives as Potential Non-opioid Analgesic Agents," *Pharmaceutical Sciences* 3: 283-287, 1997.
Viaud et al., "Acylation of Oxazolo[4,5-*b*]pyridin-2(3*H*)-ones, 2-Phenyloxazolo[4,5-*b*]pyridines and Pyrrolo[2,3-*b*]pyridin-2(2*H*)-ones," *Tetrahedron* 53(14): 5159-5168, 1997.
Villamil et al., "Efficacy of lidocaine in the treatment of pruritus in patients with chronic cholestatic liver diseases," *The American Journal of Medicine* 118: 1160-1163, 2005.
Vippagunta et al., "Crystalline solids," *Advanced Drug Delivery Reviews* 48: 3-26, 2001.
Walker et al., "Limitations in Ring Rearrangement of Fused γ-Lactams Imposed by a Quaternary Carbon Atom. Cyclization of Acid Lactams to Spiro Keto Lactams," *J. Org. Chem.* 30(9): 2973-2983, Sep. 1965.
Wang and Ganesan, "A Biomimetic Total Synthesis of (—)-Spirotryprostatin B and Related Studies," *J. Org. Chem.* 65(15): 4685-4693, 2000.
Wang and Yosipovitch, "New insights into the pathophysiology and treatment of chronic itch in patients with End-stage renal disease, Chronic liver disease and Lymphoma," *Int. J. Dermatol.* 49(1): 1-11, Jan. 2010.
Watanabe et al., "$Na_v2$/NaG Channel Is Involved in Control of Salt-Intake Behavior in the CNS," *Journal of Neuroscience* 20(20): 7743-7751, Oct. 15, 2000.
Weaver et al., "Cytochrome P450 Inhibition Using Recombinant Proteins and Mass Spectrometry/Multiple Reaction Monitoring Technology in a Cassette Incubation," *Drug Metabolism and Disposition* 31(7): 955-966, 2003.
Weber and Czugler, "Functional Group Assisted Clathrate Formation—Scissor-Like and Roof-Shaped Host Molecules," *Topics in Current Chemistry* 149: 45-135, 1988.
Weidmann et al., "2-[(2-Pyridylmethyl)sulfinyl]-1*H*-thieno[3,4-*d*]imidazoles. A Novel Class of Gastric $H^+/K^+$-ATPase Inhibitors," *J. Med. Chem.* 35: 438-450, 1992.
Wolff (ed.), *Burger's Medicinal Chemistry and Drug Discovery, Fifth Edition, Volume I. Principles and Practice*, John Wiley & Sons, Inc., New York, New York, 1994, pp. 975-977.
Wood et al., "Voltage-Gated Sodium Channels and Pain Pathways," *J. Neurobiol.* 61: 55-71, 2004.
Wrona et al., "Hydroxyl Radical-Mediated Oxidation of Serotonin: Potential Insights into the Neurotoxicity of Methamphetamine," *J. Neurochem.* 64(3): 1390-1400, 1995.
Wu et al., "The Effect of Hypercholesterolemia on the Sodium Inward Currents in Cardiac Myocyte," *J. Mol. Cell. Cardiol.* 27: 1263-1269, 1995.
Xiao and Bennett, "C-fiber spontaneous discharge evoked by chronic inflammation is suppressed by a long-term infusion of lidocaine yielding nanogram per milliliter plasma levels," *Pain* 137: 218-228, 2008.
Yang and Williams, "Palladium-Catalyzed Cyanation of Aryl Bromides Promoted by Low-Level Organotin Compounds," *Organic Letters* 6(17): 2837-2840, 2004.
Yang et al., "Nucleophilic-Type Radical Cyclizations of Indoles: Conversion of 2-Cyano 3-Substituted Indoles to Spiro-Annelated Indolines and Tetrahydrocarbazolones," *J. Org. Chem.* 58: 3100-3105, 1993.
Zhang et al., "Crystal structure of syn-1-acetyl-9'aH-8'-methoxyspiro[indole-3,2'- oxeto[3',2':4,5]furo[3,2-g][1]benzopyran]2,6'-dione," *Journal of Chemical Crystallography* 33(3): 165-168, Mar. 2003.
Zhang et al., "Photoinduced [2+2] cycloadditions (the Paterno-Büchi reaction) of 1-acetylisatin with enol ethers—regioselectivity, diastereo-selectivity and acid catalysed transformations of the spirooxetane products," *J. Chem. Soc., Perkin Trans.* 1: 345-353, 2002.
Zhao et al., "Voltage-gated sodium channel expression in rat and human epidermal keratinocytes: Evidence for a role in pain," *Pain* 139: 90-105, 2008.
Zinser et al., "Anthelmintic paraherquamides are cholinergic antagonists in gastrointestinal nematodes and mammals," *J. vet. Pharmacol. Therap.* 25: 241-250, 2002.
Invitation to Pay Additional Fees, mailed Aug. 23, 2006, for PCTAN PCT/US2006/014845, 11 pages.
International Search Report and Written Opinion, mailed Oct. 31, 2006, for PCTAN PCT/US2006/014865, 26 pages.
International Preliminary Report on Patentability, mailed Nov. 1, 2007, for PCTAN PCT/US2006/014865, 13 pages.
Official Action from Intellectual Property India, mailed Mar. 28, 2011, for India Patent Application No. 4596/CHENP/2007, 4 pages.
Chafeev et al., entitled Oxindole Compounds and Their Uses As Therapeutic Agents, Preliminary Amendment dated Jul. 14, 2006, for U.S. Appl. No. 11/408,269, 6 pages.
Chafeev et al., entitled Oxindole Compounds and Their Uses As Therapeutic Agents, Restriction Requirement mailed Sep. 9, 2008, for U.S. Appl. No. 11/408,269, 10 pages.
Chafeev et al., entitled Oxindole Compounds and Their Uses as Therapeutic Agents, Response to Restriction Requirement dated Oct. 9, 2008, for U.S. Appl. No. 11/408,269, 3 pages.
Chafeev et al., entitled Oxindole Compounds and Their Uses as Therapeutic Agents, Office Action mailed Dec. 15, 2008, for U.S. Appl. No. 11/408,269, 29 pages.
International Search Report and Written Opinion, mailed Oct. 6, 2006, for PCTAN PCT/US2006/014352, 11 pages.
International Preliminary Report on Patentability, mailed Oct. 16, 2007, for PCTAN PCT/US2006/014352, 6 pages.
Official Action from Intellectual Property Australia, dated Jan. 12, 2011, for Patent Application No. 2006235593, 5 pages.
Response to Official Action from Intellectual Property Australia, mailed May 28, 2012, for Patent Application No. 2006235593, 60 pages.
Official Action from Canadian Intellectual Property Office, dated Aug. 14, 2012, for Patent Application No. 2,604,115, 3 pages.
Official Action from State Intellectual Property Office of China, dated Dec. 25, 2009, for Patent Application No. 200680011733.9, 4 pages.
Official Action from State Intellectual Property Office of China, dated Oct. 9, 2010, for Patent Application No. 200680011733.9, 4 pages.
Official Action from State Intellectual Property Office of China, dated Oct. 10, 2011, for Patent Application No. 201110027693.X, 5 pages.
Official Action from State Intellectual Property Office of China, dated May 9, 2012, for Patent Application No. 201110027693.X, 6 pages.

(56) References Cited

OTHER PUBLICATIONS

Official Action from European Patent Office, dated Apr. 9, 2010, for Patent Application No. 06 750 402.7, 4 pages.
Response to Official Action from European Patent Office, dated Aug. 19, 2010, for Patent Application No. 06 750 402.7, 105 pages.
Official Action from European Patent Office, dated Sep. 14, 2010, for Patent Application No. 06 750 402.7, 3 pages.
Response to Official Action from European Patent Office, dated Jul. 6, 2011, for Patent Application No. 06 750 402.7, 175 pages.
Official Action from European Patent Office re extended European search report, dated Feb. 2, 2012, for Patent Application No. 11009687.2, 7 pages.
Official Action from Israel Patent Office, dated Jan. 17, 2011, for Patent Application No. 186616, 3 pages.
Response to Official Action from Israel Patent Office, mailed Jul. 14, 2011, for Patent Application No. 186616, 5 pages.
Official Action from Intellectual Property India, mailed Apr. 29, 2011, for India Patent Application No. 4597/CHENP/2007, 2 pages.
Response to Official Action from Intellectual Property India, mailed Apr. 18, 2012, for India Patent Application No. 4597/CHENP/2007, 86 pages.
Translation of Official Action from Patent Office of Japan, dated Nov. 22, 2011, for Patent Application No. 2008-506802, 11 pages.
Translation of Official Action from Patent Office of Japan, dated May 16, 2012, for Patent Application No. 2008-506802, 8 pages.
Official Action from Intellectual Property Office of New Zealand, dated Sep. 1, 2009, for Patent Application No. 561210, 2 pages.
Response to Official Action from Intellectual Property Office of New Zealand, dated Nov. 22, 2010, for Patent Application No. 561210, 2 pages.
Official Action from Intellectual Property Office of New Zealand, dated Nov. 30, 2010, for Patent Application No. 561210, 1 page.
Response to Official Action from Intellectual Property Office of New Zealand, dated Feb. 21, 2011, for Patent Application No. 561210, 2 pages.
Official Action from Intellectual Property Office of New Zealand, dated Feb. 25, 2011, for Patent Application No. 591268, 2 pages.
Official Action from Intellectual Property Office of Republic of the Philippines, dated Sep. 22, 2010, for Patent Application No. 1-2007-502050, 2 pages.
Response to Official Action from Intellectual Property Office of the Philippines, dated Jan. 20, 2011, for Patent Application No. 1-2007-502050, 85 pages.
Translation of Official Action from Intellectual Property Office of Russia, dated Mar. 16, 2010, for Patent Application No. 2007141632/04(045572), 7 pages.
Translation of Official Action from Intellectual Property Office of Russia, dated Sep. 22, 2010, for Patent Application No. 2007141632/04(045572), 7 pages.
Chafeev et al., entitled Spiro-Oxindole Compounds and Their Uses as Therapeutic Agents, Preliminary Amendment dated Jul. 5, 2006, for U.S. Appl. No. 11/402,310, 6 pages.
Chafeev et al., entitled Spiro-Oxindole Compounds and Their Uses as Therapeutic Agents, Restriction Requirement mailed Feb. 10, 2009, for U.S. Appl. No. 11/402,310, 7 pages.
Chafeev et al., entitled Spiro-Oxindole Compounds and Their Uses as Therapeutic Agents, Response to Restriction Requirement dated Feb. 25, 2009, for U.S. Appl. No. 11/402,310, 109 pages.
Chafeev et al., entitled Spiro-Oxindole Compounds and Their Uses as Therapeutic Agents, Office Action mailed May 15, 2009, for U.S. Appl. No. 11/402,310, 43 pages.
Chafeev et al., entitled Spiro-Oxindole Compounds and Their Uses as Therapeutic Agents, Amendment dated Aug. 17, 2009, for U.S. Appl. No. 11/402,310, 150 pages.
Chafeev et al., entitled Spiro-Oxindole Compounds and Their Uses as Therapeutic Agents, Notice of Allowance mailed Sep. 30, 2009, for U.S. Appl. No. 11/402,310, 9 pages.
Chafeev et al., entitled Spiro-Oxindole Compounds and Their Uses as Therapeutic Agents, Statement of the Substance of the Interview, mailed Oct. 30, 2009 for U.S. Appl. No. 11/402,310, 2 pages.

Chafeev et al., entitled Spiro-Oxindole Compounds and Their Uses as Therapeutic Agents, Communication dated Nov. 17, 2009, for U.S. Appl. No. 11/402,310, 4 pages.
Chafeev et al., entitled Spiro-Oxindole Compounds and Their Uses as Therapeutic Agents, Office Action dated Feb. 4, 2011, for U.S. Appl. No. 12/650,196, 31 pages.
Chafeev et al., entitled Spiro-Oxindole Compounds and Their Uses as Therapeutic Agents, Amendment and Winther Declaration dated May 4, 2011, for U.S. Appl. No. 12/650,196, 197 pages.
Chafeev et al., entitled Spiro-Oxindole Compounds and Their Uses as Therapeutic Agents, Office Action mailed Jun. 14, 2011, for U.S. Appl. No. 12/650,196, 17 pages.
Chafeev et al., entitled Spiro-Oxindole Compounds and Their Uses as Therapeutic Agents, Amendment dated Sep. 2, 2011, for U.S. Appl. No. 12/650,196, 15 pages.
Chafeev et al., entitled Spiro-Oxindole Compounds and Their Uses as Therapeutic Agents, Notice of Allowance dated Sep. 20, 2011, for U.S. Appl. No. 12/650,196, 11 pages.
Sun et al., entitled Spiro-Oxindole Compounds and Their Uses as Therapeutic Agents, Office Action dated Jul. 12, 2010, for U.S. Appl. No. 12/650,218, 26 pages.
Sun et al., entitled Spiro-Oxindole Compounds and Their Uses as Therapeutic Agents, Amendment dated Nov. 10, 2010, for U.S. Appl. No. 12/650,218, 28 pages.
Sun et al., entitled Spiro-Oxindole Compounds and Their Uses as Therapeutic Agents, Notice of Allowance mailed Dec. 13, 2010, for U.S. Appl. No. 12/650,218, 19 pages.
Sun et al., entitled Spiro-Oxindole Compounds and Their Uses as Therapeutic Agents, Supplemental Amendment dated Feb. 2, 2011, for U.S. Appl. No. 12/650,218, 3 pages.
Sun et al., entitled Spiro-Oxindole Compounds and Their Uses as Therapeutic Agents, Preliminary Amendment dated Jun. 24, 2011, for U.S. Appl. No. 13/078,678, 32 pages.
Sun et al., entitled Spiro-Oxindole Compounds and Their Uses as Therapeutic Agents, Restriction Requirement dated Nov. 28, 2011, for U.S. Appl. No. 13/078,678, 7 pages.
Invitation to Pay Additional Fees, mailed Jan. 2, 2007, for PCTAN PCT/US2006/014887, 9 pages.
International Search Report and Written Opinion, mailed Mar. 15, 2007, for PCTAN PCT/US2006/014887, 22 pages.
International Preliminary Report on Patentability, mailed Nov. 1, 2007, for PCTAN PCT/US2006/014887, 12 pages.
Official Action from European Patent Office, dated Aug. 5, 2008, for Patent Application No. 06 758 436.7, 5 pages.
Chafeev et al., entitled Heterocyclic Compounds and Their Uses as Therapeutic Agents, Preliminary Amendment dated Sep. 14, 2006, for U.S. Appl. No. 11/407,859, 6 pages.
Chafeev et al., entitled Heterocyclic Compounds and Their Uses as Therapeutic Agents, Restriction Requirement mailed Mar. 31, 2008, for U.S. Appl. No. 11/407,859, 9 pages.
Chafeev et al., entitled Heterocyclic Compounds and Their Uses as Therapeutic Agents, Response to Restriction Requirement dated Apr. 30, 2008, for U.S. Appl. No. 11/407,859, 39 pages.
Chafeev et al., entitled Heterocyclic Compounds and Their Uses as Therapeutic Agents, Office Action mailed Jun. 20, 2008, for U.S. Appl. No. 11/407,859, 46 pages.
Chafeev et al., entitled Heterocyclic Compounds and Their Uses as Therapeutic Agents, Amendment dated Oct. 17, 2008, for U.S. Appl. No. 11/407,859, 41 pages.
Chafeev et al., entitled Heterocyclic Compounds and Their Uses as Therapeutic Agents, Office Action mailed Jan. 15, 2009, for U.S. Appl. No. 11/407,859, 8 pages.
International Search Report and Written Opinion, mailed Aug. 11, 2006, for PCTAN PCT/US2006/013318, 15 pages.
International Preliminary Report on Patentability, mailed Oct. 16, 2007, for PCTAN PCT/US2006/013318, 9 pages.
Official Action from European Patent Office, dated Nov. 27, 2008, for Patent Application No. 06 740 804.7, 3 pages.
Response to Official Action from European Patent Office, dated Feb. 11, 2009, for Patent Application No. 06 740 804.7, 3 pages.
Official Action from Israel Patent Office, dated Jan. 16, 2011, for Patent Application No. 186615, 3 pages.

(56) References Cited

OTHER PUBLICATIONS

Response to Official Action from Israel Patent Office, dated Jul. 13, 2011, for Patent Application No. 186615, 3 pages.
Official Action from Intellectual Property of India, dated May 18, 2009, for Patent Application No. 4598/CHENP/2007, 2 pages.
Response to Official Action from Intellectual Property of India, dated Mar. 15, 2010, for Patent Application No. 4598/CHENP/2007, 27 pages.
Translation of Official Action from Patent Office of Japan, dated Nov. 4, 2011, for Patent Application No. 2008-506574, 10 pages.
Official Action from Intellectual Property Corporation of Malaysia, dated May 31, 2011, for Patent Application No. PI 20061651, 3 pages.
Response to Official Action from Intellectual Property Corporation of Malaysia, filed Aug. 11, 2011, for Patent Application No. PI 20061651, 30 pages.
Official Action from Intellectual Property Office of New Zealand, dated Aug. 27, 2009, for Patent Application No. 561204, 2 pages.
Response to Official Action from Intellectual Property Office of New Zealand, dated Nov. 22, 2010, for Patent Application No. 561204, 2 pages.
Official Action from Intellectual Property Office of New Zealand, dated Dec. 6, 2010, for Patent Application No. 561204, 1 page.
Response to Official Action from Intellectual Property Office of New Zealand, dated Feb. 16, 2011, for Patent Application No. 561204, 2 pages.
Translation of Official Action from Intellectual Property Office of Russia, dated Feb. 27, 2010, for Patent Application No. 2007141633/04(045573), 4 pages.
Chafeev et al., entitled Spiroheterocyclic Compounds and Their Uses as Therapeutic Agents, Preliminary Amendment dated Jul. 7, 2006, for U.S. Appl. No. 11/402,200, 6 pages.
Chafeev et al., entitled Spiroheterocyclic Compounds and Their Uses as Therapeutic Agents, Restriction Requirement mailed Feb. 10, 2009, for U.S. Appl. No. 11/402,200, 6 pages.
Chafeev et al., entitled Spiroheterocyclic Compounds and Their Uses as Therapeutic Agents, Response to Restriction Requirement dated Feb. 27, 2009, for U.S. Appl. No. 11/402,200, 31 pages.
Chafeev et al., entitled Spiroheterocyclic Compounds and Their Uses as Therapeutic Agents, Office Action mailed Apr. 24, 2009, for U.S. Appl. No. 11/402,200, 30 pages.
Chafeev et al., entitled Spiroheterocyclic Compounds and Their Uses as Therapeutic Agents, Amendment dated Aug. 24, 2009, for U.S. Appl. No. 11/402,200, 36 pages.
Chafeev et al., entitled Spiroheterocyclic Compounds and Their Uses as Therapeutic Agents, Office Action mailed Nov. 17, 2009, for U.S. Appl. No. 11/402,200, 7 pages.
Chafeev et al., entitled Spiroheterocyclic Compounds and Their Uses as Therapeutic Agents, Amendment dated Mar. 17, 2010, for U.S. Appl. No. 11/402,200, 17 pages.
Chafeev et al., entitled Spiroheterocyclic Compounds and Their Uses as Therapeutic Agents, Notice of Allowance dated May 13, 2010, for U.S. Appl. No. 11/402,200, 16 pages.
Chafeev et al., entitled Spiroheterocyclic Compounds and Their Uses as Therapeutic Agents, Preliminary Amendment dated Oct. 25, 2010, for U.S. Appl. No. 12/855,514, 32 pages.
Chafeev et al., entitled Spiroheterocyclic Compounds and Their Uses as Therapeutic Agents, Office Action mailed Aug. 25, 2011, for U.S. Appl. No. 12/855,514, 43 pages.
International Search Report and Written Opinion, mailed Mar. 3, 2008, for PCTAN PCT/US2007/081240, 16 pages.
International Preliminary Report on Patentability mailed Apr. 23, 2009, for PCTAN PCT/US2007/081240, 9 pages.
Chafeev et al., entitled Tricyclic Spiro-Oxindole Derivatives and Their Uses as Therapeutic Agents, Restriction Requirement mailed Jan. 26, 2012, for U.S. Appl. No. 12/445,271, 7 pages.
International Search Report and Written Opinion, mailed Oct. 13, 2008, for PCTAN PCT/US2007/081323, 21 pages.
International Preliminary Report on Patentability, mailed Apr. 15, 2009, for PCTAN PCT/US2007/081323, 12 pages.
International Search Report and Written Opinion, mailed Mar. 3, 2008, for PCTAN PCT/US2007/081244, 21 pages.
International Preliminary Report on Patentability, mailed Apr. 23, 2009, for PCTAN PCT/US2007/081244, 12 pages.
Official Action from State Intellectual Property Office of China, dated May 5, 2011, for Patent Application No. 200780038272.9, 9 pages.
Official Action from State Intellectual Property Office of China, dated Feb. 20, 2012, for Patent Application No. 200780038272.9, 5 pages.
Cadieux et al., entitled Spiro (Furo [3, 2-C] Pyridine-3-3'-Indol) -2' (1'H)-One Derivatives and Related Compounds for the Treatment of Sodium-Channel Mediated Diseases, Such as Pain, Restriction Requirement mailed Apr. 19, 2012, for U.S. Appl. No. 12/445,270, 6 pages.
International Search Report and Written Opinion, mailed Apr. 1, 2011, for PCTAN PCT/US2010/052704, 12 pages.
International Preliminary Report on Patentability, mailed Apr. 17, 2012, for PCTAN PCT/US2010/052704, 6 pages.
Cadieux et al., entitled Synthetic Methods for Spiro-Oxindole Compounds, Restriction Requirement mailed May 7, 2012, for U.S. Appl. No. 12/904,880, 7 pages.
Cadieux et al., entitled Synthetic Methods for Spiro-Oxindole Compounds, Response to Restriction Requirement mailed Jun. 7, 2012, for U.S. Appl. No. 12/904,880, 1 page.
Cadieux et al., entitled Synthetic Methods for Spiro-Oxindole Compounds, Office Action mailed Aug. 16, 2012, for U.S. Appl. No. 12/904,880, 40 pages.
Cadieux et al., entitled Synthetic Methods for Spiro-Oxindole Compounds, Amendment mailed Nov. 16, 2012, for U.S. Appl. No. 12/904,880, 15 pages.
Invitation to Pay Additional Fees, mailed Jul. 16, 2008, for PCTAN PCT/US2007/081319, 10 pages.
International Search Report and Written Opinion, mailed Dec. 29, 2008, for PCTAN PCT/US2007/081319, 18 pages.
International Preliminary Report on Patentability, mailed Apr. 15, 2009, for PCTAN PCT/US2007/081319, 8 pages.
International Search Report and Written Opinion, mailed May 19, 2008, for PCTAN PCT/US2007/081247, 18 pages.
International Preliminary Report on Patentability, mailed Apr. 15, 2009, for PCTAN PCT/US2007/081247, 10 pages.
Official Action from Intellectual Property Australia, dated Mar. 22, 2012, for Patent Application No. 2007319580, 2 pages.
Official Action from State Intellectual Property Office of China, dated Oct. 28, 2010, for Patent Application No. 200780038111.X, 5 pages.
Official Action from State Intellectual Property Office of China, dated Jul. 14, 2011, for Patent Application No. 200780038111.X, 5 pages.
Official Action from State Intellectual Property Office of China, dated Jun. 8, 2012, for Patent Application No. 200780038111.X, 7 pages.
Official Action from European Patent Office, dated Jul. 7, 2009, for Patent Application No. 07 868 434.7, 3 pages.
Official Action from European Patent Office, dated Jul. 23, 2010, for Patent Application No. 07 868 434.7, 6 pages.
Response to Official Action from European Patent Office, dated May 23, 2011, for Patent Application No. 07 868 434.7, 3 pages.
Translation of Official Action from Patent Office of Japan, dated Sep. 26, 2012, for Patent Application No. 2009-532606, 5 pages.
Translation of Official Action from Intellectual Property Office of Russia, dated Aug. 31, 2011, for Patent Application No. 2009117642, 4 pages.
Translation of Official Action from Intellectual Property Office of Russia, dated Feb. 2, 2012, for Patent Application No. 2009117642, 8 pages.
Chafeev et al., entitled Use of Spiro-Oxindole Compounds as Therapeutic Agents, Preliminary Amendment dated Mar. 4, 2010, for U.S. Appl. No. 12/445,264, 18 pages.
Chafeev et al., entitled Use of Spiro-Oxindole Compounds as Therapeutic Agents, Restriction Requirement mailed Aug. 24, 2012, for U.S. Appl. No. 12/445,264, 8 pages.

(56) References Cited

OTHER PUBLICATIONS

Chafeev et al., entitled Use of Spiro-Oxindole Compounds as Therapeutic Agents, Response to Restriction Requirement filed Sep. 24, 2012, for U.S. Appl. No. 12/445,264, 19 pages.
International Search Report and Written Opinion, mailed May 13, 2008, for PCTAN PCT/US2007/081318, 12 pages.
International Preliminary Report on Patentability, mailed Apr. 15, 2009, for PCTAN PCT/US2007/081318, 5 pages.
International Search Report and Written Opinion, mailed Mar. 6, 2008, for PCTAN PCT/US2007/081297, 18 pages.
International Preliminary Report on Patentability, mailed Apr. 15, 2009, for PCTAN PCT/US2007/081297, 10 pages.
Invitation to Pay Additional Fees, mailed Jan. 27, 2009, for PCTAN PCT/US2007/081320, 7 pages.
Written Opinion of the International Searching Authority, mailed Jan. 5, 2009, for PCTAN PCT/US2007/081320, 11 pages.
International Preliminary Report on Patentability, mailed May 5, 2009, for PCTAN PCT/US2007/081320, 12 pages.
International Search Report and Written Opinion, mailed Dec. 1, 2011, for PCTAN PCT/US2010/052703, 13 pages.
International Preliminary Report on Patentability, mailed Apr. 17, 2012, for PCTAN PCT/US2010/052703, 9 pages.
Winters et al., entitled Pharmaceutical Compositions for Oral Administration, Preliminary Amendment dated Dec. 27, 2010, for U.S. Appl. No. 12/905,048, 9 pages.
Winters et al., entitled Pharmaceutical Compositions for Oral Administration, Restriction Requirement, mailed May 7, 2012, for U.S. Appl. No. 12/905,048, 9 pages.
International Search Report and Written Opinion, mailed Feb. 9, 2010, for PCTAN PCT/US2009/063290, 13 pages.
International Preliminary Report on Patentability, mailed May 10, 2011, for PCTAN PCT/US2009/063290, 7 pages.
International Search Report and Written Opinion, mailed Oct. 1, 2010, for PCTAN PCT/US2010/040187, 13 pages.
International Preliminary Report on Patentability, mailed Jan. 4, 2012, for PCTAN PCT/US2010/040187, 7 pages.
Response to Official Action from European Patent Office, dated Aug. 7, 2012, for Patent Application No. 10 731 662.2, 21 pages.
Response to Official Action from Philippines Intellectual Property Office, dated Jun. 15, 2012, for Patent Application No. 1-2011-502619, 3 pages.
Chafeev et al., entitled Enantiomers of Spiro-Oxindole Compounds and Their Uses as Therapeutic Agents, Restriction Requirement mailed Jun. 20, 2011, for U.S. Appl. No. 12/825,168, 8 pages.
Chafeev et al., entitled Enantiomers of Spiro-Oxindole Compounds and Their Uses as Therapeutic Agents, Response to Restriction Requirement and Preliminary Amendment, filed Jul. 20, 2011, for U.S. Appl. No. 12/825,168, 5 pages.
Chafeev et al., entitled Enantiomers of Spiro-Oxindole Compounds and Their Uses as Therapeutic Agents, Office Action, mailed Aug. 29, 2011, for U.S. Appl. No. 12/825,168, 43 pages.
Chafeev et al., entitled Enantiomers of Spiro-Oxindole Compounds and Their Uses as Therapeutic Agents, Amendment filed Jan. 30, 2012, for U.S. Appl. No. 12/825,168, 8 pages.
Chafeev et al., entitled Enantiomers of Spiro-Oxindole Compounds and Their Uses as Therapeutic Agents, Office Action, mailed Feb. 28, 2012, for U.S. Appl. No. 12/825,168, 13 pages.
Chafeev et al., entitled Enantiomers of Spiro-Oxindole Compounds and Their Uses as Therapeutic Agents, Amendment and Cadieux Declaration filed May 29, 2012, for U.S. Appl. No. 12/825,168, 17 pages.
Invitation to Pay Additional Fees, mailed Feb. 9, 2010, for PCTAN PCT/US2009/060537, 8 pages.
International Search Report and Written Opinion, mailed Oct. 6, 2010, for PCTAN PCT/US2009/060537, 18 pages.
International Preliminary Report on Patentability, mailed Apr. 19, 2011, for PCTAN PCT/US2009/060537, 11 pages.
Response to Official Action from European Patent Office, dated Jan. 10, 2012, for Patent Application No. 09 740 589.8, 4 pages.
Official Action from European Patent Office, dated Sep. 11, 2012, for Patent Application No. 09 740 589.8, 5 pages.
Official Action from Intellectual Property Office of New Zealand, mailed Sep. 9, 2011, for New Zealand Patent Application No. 592275, 2 pages.
Chafeev et al., entitled Spiro-Oxindole Compounds and Their Use as Therapeutic Agents, Preliminary Amendment dated Jan. 12, 2010, for U.S. Appl. No. 12/578,148, 57 pages.
Chafeev et al., entitled Spiro-Oxindole Compounds and Their Use as Therapeutic Agents, Restriction Requirement mailed Aug. 15, 2011, for U.S. Appl. No. 12/578,148, 10 pages.
Chafeev et al., entitled Spiro-Oxindole Compounds and Their Use as Therapeutic Agents, Response to Restriction Requirement dated Sep. 14, 2011, for U.S. Appl. No. 12/578,148, 57 pages.
Chafeev et al., entitled Spiro-Oxindole Compounds and Their Use as Therapeutic Agents, Office Action mailed Oct. 21, 2011, for U.S. Appl. No. 12/578,148, 51 pages.
Chafeev et al., entitled Spiro-Oxindole Compounds and Their Use as Therapeutic Agents, Response to Office Action dated Feb. 21, 2012, for U.S. Appl. No. 12/578,148, 46 pages.
Chafeev et al., entitled Spiro-Oxindole Compounds and Their Use as Therapeutic Agents, Notice of Allowance dated Apr. 27, 2012 for U.S. Appl. No. 12/578,148, 12 pages.
Chafeev et al., entitled Spiro-Oxindole Compounds and Their Use as Therapeutic Agents, Restriction Requirement mailed Oct. 10, 2012, for U.S. Appl. No. 13/557,833, 9 pages.
Chafeev et al., entitled Spiro-Oxindole Compounds and Their Use as Therapeutic Agents, Response to Restriction Requirement filed Nov. 9, 2012, for U.S. Appl. No. 13/557,833, 14 pages.
International Search Report and Written Opinion, mailed Jan. 22, 2010, for PCTAN PCT/US2009/060455, 14 pages.
International Preliminary Report on Patentability, mailed Apr. 19, 2011, for PCTAN PCT/US2009/060455, 7 pages.
Response to Official Action from European Patent Office, dated Feb. 1, 2012, for Patent Application No. 09 741 118.5, 12 pages.
Chafeev et al., entitled Spiro-Oxindole Compounds and Their Use as Therapeutic Agents, Office Action dated Apr. 1, 2011, for U.S. Appl. No. 12/577,799, 49 pages.
Chafeev et al., entitled Spiro-Oxindole Compounds and Their Use as Therapeutic Agents, Amendment dated Jul. 1, 2011, for U.S. Appl. No. 12/577,799, 21 pages.
Chafeev et al., entitled Spiro-Oxindole Compounds and Their Use as Therapeutic Agents, Notice of Allowance mailed Oct. 7, 2011, for U.S. Appl. No. 12/577,799, 14 pages.
International Search Report and Written Opinion, mailed Apr. 8, 2010, for PCTAN PCT/US2009/069663, 13 pages.
International Preliminary Report on Patentability, mailed Jun. 29, 2011, for PCTAN PCT/US2009/069663, 6 pages.
Invitation to Pay Additional Fees, mailed Aug. 18, 2010, for PCTAN PCT/US2010/034223, 7 pages.
International Search Report and Written Opinion, mailed Jul. 11, 2011, for PCTAN PCT/US2010/034223, 18 pages.
International Preliminary Report on Patentability, mailed Nov. 15, 2011, for PCTAN PCT/US2010/034223, 11 pages.
International Search Report and Written Opinion, mailed Jun. 9, 2011, for PCTAN PCT/US2011/026359, 14 pages.
International Preliminary Report on Patentability, mailed Oct. 23, 2012, for PCTAN PCT/US2011/026359, 10 pages.
U.S. Appl. No. 13/909,964, filed Jun. 4, 2013, Chafeev et al.
U.S. Appl. No. 14/272,297, filed May 7, 2014, Cadieux et al.
Cummins et al., "The roles of sodium channels in nociception: Implications for mechanisms of pain," *Pain* 131: 243-257, 2007.
Feldman et al., "Extending Pummerer Reaction Chemistry. Development of a Strategy for the Regio- and Stereoselective Oxidative Cyclization of 3-(ω-Nucleophile)-Tethered Indoles," *J. Org. Chem.* 70(16): 6429-6440, 2005.
Fertleman et al., "*SCN9A* Mutations in Paroxysmal Extreme Pain Disorder: Allelic Variants Underlie Distinct Channel Defects and Phenotypes," *Neuron* 52: 767-774, Dec. 7, 2006.
Hoyt et al., "Benzazepionone $Na_v1.7$ blockers: Potential treatments for neuropathic pain," *Bioorganic & Medicinal Chemistry Letters* 17: 6172-6177, 2007.

(56) References Cited

OTHER PUBLICATIONS

McGowan et al., "A Peripherally Acting $Na_v1.7$ Sodium Channel Blocker Reverses Hyperalgesia and Allodynia on Rat Models of Inflammatory and Neuropathic Pain," *Anesthesia & Analgesia* 109(3): 951-958, Sep. 2009.
Official Action from European Patent Office re extended European search report, dated Jun. 6, 2014, for Patent Application No. 14001216.2, 7 pages.
Official Action from Intellectual Property Corporation of Malaysia, mailed Jul. 31, 2014, for Patent Application No. PI 2010003197, 3 pages.
Response to Official Action from European Patent Office, dated Dec. 14, 2012, for Patent Application No. 10 771 606.0, 25 pages.
Official Action from New Zealand Intellectual Property Office, dated Mar. 13, 2014, for Patent Application No. 622072, 2 pages.
Cadieux et al., entitled Synthetic Methods for Spiro-Oxindole Compounds, Preliminary Amendment dated Jul. 22, 2014, for U.S. Appl. No. 14/272,297, 5 pages.
Translation of Official Action from State Intellectual Property Office of China, dated Apr. 29, 2014, for Patent Application No. 201080029572.2, 5 pages.
Translation of Official Action from Russian Patent Office, dated Jun. 4, 2014, for Patent Application No. 2012102896, 2 pages.
Translation of Official Action from Taiwanese Patent Office, dated May 6, 2014, for Patent Application No. 099121292, 3 pages.
Chafeev et al., entitled Enantiomers of Spiro-Oxindole Compounds and Their Uses as Therapeutic Agents, Amendment filed Feb. 28, 2014, for U.S. Appl. No. 13/619,915, 8 pages.
Chafeev et al., entitled Enantiomers of Spiro-Oxindole Compounds and Their Uses as Therapeutic Agents, Office Action mailed Mar. 18, 2014, for U.S. Appl. No. 13/619,915, 16 pages.
Chafeev et al., entitled Enantiomers of Spiro-Oxindole Compounds and Their Uses as Therapeutic Agents, Amendment filed Jun. 18, 2014, for U.S. Appl. No. 13/619,915, 7 pages.
Chafeev et al., entitled Enantiomers of Spiro-Oxindole Compounds and Their Uses as Therapeutic Agents, Notice of Allowance mailed Jul. 11, 2014, for U.S. Appl. No. 13/619,915, 8 pages.
Response to Official Action from Intellectual Property Australia, mailed Jul. 8, 2014, for Patent Application No. 2009303468, 60 pages.
Response to Official Action from European Patent Office, dated Jan. 9, 2013, for Patent Application No. 09 740 589.8, 32 pages.
Official Action from European Patent Office, dated Mar. 18, 2014, for Patent Application No. 09 740 589.8, 4 pages.
Response to Official Action from European Patent Office, dated Jul. 2, 2014, for Patent Application No. 09 740 589.8, 135 pages.
Chafeev et al., entitled Spiro-Oxindole Compounds and Their Use as Therapeutic Agents, Office Action mailed Apr. 28, 2014, for U.S. Appl. No. 13/787,558, 13 pages.
Chafeev et al., entitled Spiro-Oxindole Compounds and Their Use as Therapeutic Agents, Amendment dated Jul. 28, 2014, for U.S. Appl. No. 13/787,558, 10 pages.
Translation of Official Action from Taiwanese Intellectual Property Office, dated Jan. 17, 2014, for Patent Application No. 098135185, 4 pages.
Response to Official Action from Intellectual Property Office of New Zealand, mailed Jul. 30, 2014, for New Zealand Patent Application No. 601667, 55 pages.
Official Action from State Intellectual Property Office of China, dated Jul. 17, 2014, for Patent Application No. 201180010245.7, 6 pages.
Official Action from Intellectual Property Office of Singapore, mailed Jul. 11, 2014, for Singapore Patent Application No. 2012056909, 13 pages.
U.S. Appl. No. 14/542,367, filed Nov. 14, 2014, Chafeev et al.
Saishin Souyaku-Kagaku, $1^{st}$ volume, Chapter 21, Yakubutsu no Sayou no Rittai-Kagaku II: Enantiomer, Ken-ichiro Otsuka, Technomics Corporation, 1998, $1^{st}$ edition, pp. 475-501, 28 pages.
Shin-Jikkenn Kagaku Koza I, Kihon-sosa, 1975, pp. 325-337, 4 pages.
Translation of Official Action from State Intellectual Property Office of China, dated Oct. 11, 2014, for Patent Application No. 201110027693.X, 4 pages.
Translation of Official Action from Korean Intellectual Property Office, mailed Aug. 7, 2014, for Patent Application No. 10-2014-7009732, 2 pages.
Translation of Official Action from Ministry of Scientific Research Academy of scientific Research & Technology Patent Office, dated Aug. 15, 2014, for Patent Application No. PCT/2012.67, 6 pages.
Official Action from European Patent Office re extended European search report, dated Apr. 9, 2014, for Patent Application No. 14000519.0, 9 pages.
Translation of Official Action from Japanese Patent Office, dated Oct. 31, 2014, for Patent Application No. 2012-534362, 6 pages.
Official Action from Intellectual Property Office of Singapore, dated Aug. 14, 2014, for Patent Application No. 2012025391, 14 pages.
Translation of Official Action from State Intellectual Property Office of China, dated Jul. 2, 2014, for Patent Application No. 200780038111.X, 11 pages.
Official Action from Australian Government IP Australia, dated Aug. 4, 2014, for Patent Application No. 2010266549, 3 pages.
Translation of Official Action from State Intellectual Property Office of China, dated Oct. 10, 2014, for Patent Application No. 201080029572.2, 5 pages.
Official Action from European Patent Office re extended European search report, dated Sep. 15, 2014, for Patent Application No. 14000690.9, 7 pages.
Official Action from European Patent Office, dated Oct. 20, 2014, for Patent Application No. 14000690.9, 2 pages.
Response to Official Action mailed Nov. 18, 2014, for Patent Application No. 14000690.9, 10 pages.
Official Action from Patent Office of the Cooperation Council for the Arab States of the Gulf, dated Jul. 9, 2014, for Patent Application No. 2010-16197, 6 pages.
Translation of Official Action from Japanese Patent Office dated Jul. 24, 2014, for Patent Application No. 2012-517823, 5 pages.
Translation of Notice of Allowance from Russian Patent Office, dated Aug. 21, 2014, for Patent Application No. 2012102896, 6 pages.
Chafeev et al., entitled Spiro-Oxindole Compounds and Their Use as Therapeutic Agents, Notice of Allowance dated Aug. 4, 2014, for U.S. Appl. No. 13/787,558, 12 pages.
Official Action from Intellectual Property Office of New Zealand, mailed Aug. 12, 2014, for New Zealand Patent Application No. 601667, 2 pages.
International Preliminary Report on Patentability, mailed Oct. 14, 2014, for PCTAN PCT/US2013/030219, 10 pages.
Lima, "Disclosure: Drugs and chirality: a brief approach," *Química Nova* 20(6): 657-663, 1997 (with translation), 19 pages.
Official Action from Canadian Intellectual Property Office, dated Jun. 3, 2015, for Patent Application No. 2,853,635, 5 pages.
Official Action from European Patent Office, dated May 28, 2015, for Patent Application No. 14001216.2, 2 pages.
Translation of Official Action from Patent Office of Japan, mailed Jul. 23, 2015, for Patent Application No. 2014-078569, 4 pages.
Translation of Official Action from Korean Intellectual Property Office, mailed Mar. 31, 2015, for Patent Application No. 10-2014-7009732, 2 pages.
Official Action from Intellectual Property Australia, dated Aug. 14, 2015, for Patent Application No. 2010306768, 3 pages.
Translation of Official Action from Ministry of Scientific Research Academy of scientific Research & Technology Patent Office, dated Apr. 22, 2015, for Patent Application No. PCT/2012.671, 7 pages.
Response to Official Action from European Patent Office, dated Apr. 24, 2015, for Patent Application No. 14000519.0, 10 pages.
Response to Official Action from New Zealand Intellectual Property Office, mailed Jun. 9, 2015, for Patent Application No. 622072, 22 pages.
Official Action from New Zealand Intellectual Property Office, dated Jun. 22, 2015, for Patent Application No. 622072, 2 pages.
Response to Official Action from Australian Government IP Australia, mailed May 6, 2015, for Patent Application No. 2010266549, 6 pages.

(56) References Cited

OTHER PUBLICATIONS

Translation of Official Action from Japanese Patent Office dated Feb. 6, 2015, for Patent Application No. 2012-517823, 4 pages.
Official Action from Intellectual Property Corporation of Malaysia, dated Apr. 30, 2015, for Patent Application No. PI 2011006363, 3 pages.
Official Action from Philippines Intellectual Property Office, dated May 20, 2015, for Patent Application No. 1-2011-502619, 2 pages.
Chafeev et al., entitled Enantiomers of Spiro-Oxindole Compounds and Their Uses as Therapeutic Agents, Restriction Requirement mailed Jul. 30, 2015, for U.S. Appl. No. 14/510,634, 8 pages.
Translation of Official Action from State Intellectual Property Office of China, dated Feb. 27, 2015, for Patent Application No. 201310525520.X, 9 pages.
Translation of Official Action from Patent Office of Japan, dated Dec. 15, 2014, for Patent Application No. 2014-084287, 2 pages.
Translation of Official Action from Patent Office of Japan, dated Apr. 23, 2015, for Patent Application No. 2014-084287, 7 pages.
Official Action from Intellectual Property Office of the Philippines, mailed Apr. 10, 2015, for Philippines Patent Application No. 1/2011/500758, 2 pages.
Translation of Official Action from State Intellectual Property Office of China, dated Mar. 18, 2015, for Patent Application No. 201180010245.7, 7 pages.
Translation of Official Action from Patent Office of Israel, dated Jul. 23, 2015, for Patent Application No. 221646, 3 pages.
Translation of Official Action from Patent Office of Japan, dated Jan. 27, 2015, for Patent Application No. 2012-555199, 4 pages.
Translation of Official Action from Patent Office of Russia, dated Feb. 19, 2015, for Patent Application No. 2012140955, 4 pages.
Official Action from European Patent Office, dated Jan. 27, 2015, for Patent Application No. 13710961.7, 2 pages.
Response to Official Action from European Patent Office, mailed Aug. 5, 2015, for Patent Application No. 13710961.7, 8 pages.
Official Action from Intellectual Property Office of New Zealand, mailed Jul. 9, 2015, for Patent Application No. 630189, 2 pages.
Dib-Hajj et al., "Gain-of-function mutation in $Na_v1.7$ in familial erythromelalgia induces bursting of sensory neurons," *Brain* 128: 1847-1854, 2005.
Response to Official Action from European Patent Office, mailed Oct. 13, 2015, for Patent Application No. 14001216.2, 48 pages.
Official Action from Canadian Intellectual Property Office, dated May 27, 2016, for Patent Application No. 2,777,543, 4 pages.
Translation of Official Action from Japanese Patent Office, dated Oct. 15, 2015, for Patent Application No. 2015-039888, 5 pages.
Official Action from New Zealand Intellectual Property Office, dated Oct. 5, 2015, for Patent Application No. 712378, 2 pages.
Translation of Official Action from Intellectual Property Office of Russia, dated Jul. 14, 2014, for Patent Application No. 2012119550, 2 pages.
Cadieux et al., entitled Synthetic Methods for Spiro-Oxindole Compounds, Office Action mailed Mar. 11, 2015, for U.S. Appl. No. 14/272,297, 48 pages.
Cadieux et al., entitled Synthetic Methods for Spiro-Oxindole Compounds, Amendment filed Jun. 29, 2015, for U.S. Appl. No. 14/272,297, 11 pages.
Translation of Official Action from Korean Intellectual Property Office, dated Apr. 17, 2016, for United Arab Emirates Patent Application No. P/1336/2011, 8 pages.
Response to Official Action from Korean Intellectual Property Office, mailed Jun. 13, 2016, for United Arab Emirates Patent Application No. P/1336/2011, 4 pages.
Official Action from Australian Government IP Australia, dated Mar. 22, 2016, for Patent Application No. 2015224493, 3 pages.
Translation of Official Action from Japanese Patent Office dated Nov. 24, 2015, for Patent Application No. 2014-235262, 2 pages.
Response to Official Action from Japanese Patent Office mailed Jun. 7, 2016, for Patent Application No. 2014-235262, 3 pages.
Chafeev et al., entitled Enantiomers of Spiro-Oxindole Compounds and Their Uses as Therapeutic Agents, Response to Restriction Requirement mailed Nov. 30, 2015, for U.S. Appl. No. 14/510,634, 2 pages.
Chafeev et al., entitled Enantiomers of Spiro-Oxindole Compounds and Their Uses as Therapeutic Agents, Office Action dated Dec. 8, 2015, for U.S. Appl. No. 14/510,634, 52 pages.
Chafeev et al., entitled Enantiomers of Spiro-Oxindole Compounds and Their Uses as Therapeutic Agents, Amendment filed Jun. 8, 2016, for U.S. Appl. No. 14/510,634, 5 pages.
Official Action from Intellectual Property Australia, dated Jan. 13, 2016, for Patent Application No. 2014265116, 2 pages.
Response to Official Action from Canadian Intellectual Property Office, mailed Jan. 18, 2016, for Patent Application No. 2,741,029, 43 pages.
Official Action from Canadian Intellectual Property Office, dated Mar. 31, 2016, for Patent Application No. 2,741,029, 4 pages.
Official Action from Canadian Intellectual Property Office, dated Jul. 16, 2015, for Patent Application No. 2,741,029, 5 pages.
Chafeev et al., entitled Spiro-Oxindole Compounds and Their Use as Therapeutic Agents, Restriction Requirement mailed Nov. 13, 2015, for U.S. Appl. No. 14/542,367, 8 pages.
Chafeev et al., entitled Spiro-Oxindole Compounds and Their Use as Therapeutic Agents, Response to Restriction Requirement filed May 10, 2016, for U.S. Appl. No. 14/542,367, 12 pages.
Translation of Official Action from Korean Intellectual Property Office, dated Apr. 17, 2016, for United Arab Emirates Patent Application No. P/0905/2012, 12 pages.
Official Action from Intellectual Property Australia, dated Sep. 30, 2015, for Patent Application No. 2011220396, 3 pages.
Translation of Official Action from Patent Office of Japan, dated Dec. 22, 2015, for Patent Application No. 2012-555199, 6 pages.
Translation of Official Action from Eurasian Patent Office, dated Sep. 29, 2015, for Patent Application No. 201491854/28, 5 pages.
Translation of Official Action from State Intellectual Property Office of China, dated Sep. 21, 2015, for Patent Application No. 201380030552.0, 13 pages.
Official Action from the Intellectual Property Corporation of Malaysia, mailed Jul. 29, 2016, for Patent Application No. PI 2012003812, 4 pages.

* cited by examiner

PHARMACEUTICAL COMPOSITIONS OF SPIRO-OXINDOLE COMPOUND FOR TOPICAL ADMINISTRATION AND THEIR USE AS THERAPEUTIC AGENTS

CROSS REFERENCE TO RELATED APPLICATIONS

This application is a national stage application filed under 35 U.S.C. 371 of International Application No. PCT/US2011/026359, accorded an International Filing Date of Feb. 25, 2011, which claims priority to U.S. Provisional Patent Application No. 61/308,759 filed on Feb. 26, 2010. These applications are incorporated herein by reference in their entireties.

FIELD OF THE INVENTION

The present invention relates to a pharmaceutical composition for topical administration to a mammal, preferably a human, comprising one or more pharmaceutically acceptable excipients and a therapeutically effective amount of a spiro-oxindole compound that is a sodium channel blocker, preferably a neuronal voltage-gated sodium channel antagonist. In particular, the present invention relates to pharmaceutical compositions for treating diseases or conditions, such as pain, preferably post-herpetic neuralgia (PHN), osteoarthritis, and persistent post-operative pain, which is alleviated by the inhibition of a sodium channel, preferably a neuronal voltage-gated sodium channel. However, other neurological disorders unrelated to pain could similarly be treated as part of this invention, for example, alleviation of symptoms of myotonia and multiple sclerosis.

BACKGROUND OF THE INVENTION

Diseases and conditions which are alleviated by the inhibition (or "blocking") of sodium channels, particularly neuronal voltage-gated sodium channels, include acute and chronic pain, particularly neuropathic and inflammatory pain. Persistent (chronic) neuropathic pain occurs in a wide range of clinical conditions, including post-herpetic neuralgia (PHN), trigeminal neuralgia, painful diabetic neuropathy (PDN), lower back pain, post-operative pain, chemotherapy-related and HIV infection. Estimates of the prevalence of chronic neuropathic pain vary greatly by geographical region, ranging from approximately 11% of the population of the U.S. to estimates that 20% of all European adults suffer with moderate to severe chronic pain (see, for example, Hall, G. C. et al., "Primary Care Incidence and Treatment of Four Neuropathic Pain Conditions: A Descriptive Study, 2002-2005," *BMC Fam. Pract.* (2008); Vol. 9, No. 26; and Hardt, J. et al., "Prevalence of Chronic Pain in a Representative Sample in the United States," *Pain Medicine* (2008), Vol. 9, No. 7, pp. 803-812). In the U.S., the most common chronic neuropathic pain conditions, PHN and PDN, are thought to affect 1 million and 3 million people, respectively (see, for example, Dworkin, R. H. et al., "Advances in Neuropathic Pain Diagnosis, Mechanism, and Treatment Recommendations," *Arch. Neurol.* (2003), Vol. 60, pp. 1524-1534).

Numerous pharmacological agents are available for the treatment of neuropathic pain, including tricyclic antidepressants, serotonin noradrenaline reuptake inhibitors, anticonvulsants (e.g., gabapentin and pregabalin), local anaesthetics and opioids (e.g., morphine). However, these treatments offer sub-optimal efficacy and/or have unacceptable side effects in a chronic setting, with adequate relief of neuropathic pain reported in only approximately 50% of patients (see, for example, Moulin, D. E., "The Clinical Management of Neuropathic Pain," *Pain Res. Manag.* (2006), Vol. 11 (Supplement A), pp. 30A-36A). Frequently, multiple drug therapy with tricyclic antidepressants, anticonvulsants and local anaesthetics is necessary for relief of neuropathic pain.

The Lidoderm® patch (5% lidocaine) belongs to a class of local and topical anaesthetic medications and is approved for the treatment of PHN. However, while lidocaine may have local effects, it is systemically absorbed and must be used with extreme caution when administered topically, as applying to too large a surface area can result in severe systemic toxicity and death.

Voltaren® (diclofenac sodium gel) is a non-steroidal anti-inflammatory agent (NSAID) in a topical formulation. It is a marketed treatment option for osteoarthritis patients. While the risk of gastrointestinal side effects for NSAID topical use is lower than it is for NSAID oral use, these serious side effects remain a concern for topical diclofenac. Furthermore, meaningful elevation of hepatic enzymes has recently been reported in some patients on long-term topical diclofenac, necessitating regular monitoring for hepatotoxicity in this patient population (see, FDA website, MedWatch, 2009; Volteren Gel (diclofenac sodium) 1% topical gel; Safety Labeling Changes Approved by FDA Center for Drug Evaluation and Research—September 2009).

Neuronal voltage-gated sodium channels ($Na_v$'s) are well-known to modulate the transmission of pain signals. For example, loss-of-function mutations of $Na_v1.7$, which is expressed primarily in sensory neurons of the peripheral nervous system and is upregulated by both nerve injury and inflammation, cause a human condition known as congenital indifference to pain, which is characterized by an inability to sense pain (see, for example, Goldberg, Y. P. et al., *Clin. Genet.* (2007), Vol. 71, No. 4, pp. 311-119). Lidocaine and other local anaesthetics act mainly by inhibiting $Na_v$'s.

PCT Published Patent Application No. WO 06/110917 is directed to spiro-oxindole compounds which are disclosed as being useful as sodium channel blockers. These compounds, inter alia, inhibit sodium ion flux through sodium channels. As such, the compounds are considered to be sodium channel blockers and are therefore useful for treating diseases and conditions in mammals, preferably humans, which are the result of aberrant voltage-dependent sodium channel biological activity or which may be ameliorated by modulation of the biological activity of sodium channels.

There exists, therefore, a need for a topical pharmaceutical composition comprising a compound that is a sodium channel blocker, preferably a neuronal voltage-gated sodium channel antagonist, for the treatment of pain having minimal systemic exposure of the compound and that is cosmetically and pharmaceutically acceptable for chronic application of the compound to the skin (i.e., non-irritating, non-stinging and non-sensitizing).

SUMMARY OF THE INVENTION

The present invention is directed to pharmaceutical compositions comprising one or more pharmaceutically acceptable excipients and a therapeutically effective amount of a spiro-oxindole compound, or a pharmaceutically acceptable salt thereof. In particular, the present invention is directed to pharmaceutical compositions comprising one or more pharmaceutically acceptable excipients and a therapeutically effective amount of a spiro-oxindole compound that is a sodium channel blocker. Such pharmaceutical compositions are useful in the treatment and/or prevention of diseases or conditions mediated by sodium channels and are topically administered to a mammal, preferably a human, in need thereof, with minimal systemic exposure of the spiro-oxindole compound.

Accordingly, in one aspect, the invention is directed to a pharmaceutical composition for topical administration to a mammal, wherein the pharmaceutical composition comprises one or more pharmaceutically acceptable excipients and a therapeutically effective amount of a spiro-oxindole compound having the following formula:

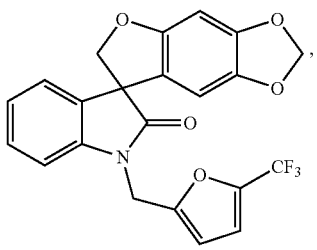 [SMILES: O=C1N(Cc2ccc(C(F)(F)F)o2)c2ccccc2C12COc1cc3c(cc12)OCO3]

as an enantiomer, a racemate or a non-racemic mixture of enantiomers, or a pharmaceutically acceptable salt thereof.

In another aspect, the invention provides a method for the treatment of pain in a mammal, preferably a human, wherein the method comprises administering to the mammal in need thereof a therapeutically effective amount of a pharmaceutical composition of the invention as set forth above.

In another aspect, the present invention provides a method for treating or lessening the severity of a disease, condition, or disorder where activation or hyperactivity of one or more of neuronal voltage-gated sodium channels selected from $Na_v1.1$, $Na_v1.2$, $Na_v1.3$, $Na_v1.4$, $Na_v1.5$, $Na_v1.6$, $Na_v1.7$, $Na_v1.8$, or $Na_v1.9$ is implicated in the disease, condition or disorder, wherein the methods comprise administering to the mammal in need thereof a therapeutically effective amount of a pharmaceutical composition of the invention as set forth above.

In another aspect, the invention provides a method of treating a range of sodium channel-mediated diseases or conditions, preferably neuronal voltage-gated sodium channel-mediated diseases or conditions, wherein the diseases or conditions are selected from, but are not limited to, pain associated with HIV, HIV treatment induced neuropathy, trigeminal neuralgia, post-herpetic neuralgia (PHN), familial erythromelalgia, primary erythromelalgia, familial rectal pain, eudynia, heat sensitivity, pain associated with multiple sclerosis (MS), amyotrophic lateral sclerosis (ALS), painful diabetic neuropathy, peripheral neuropathy, arthritis, rheumatoid arthritis, osteoarthritis, tendonitis, bursitis, musculoskeletal sprains, tenosinovitis, chondromalacia patellae, myositis, myotonia (including but not limited to SCN4A-related myotonia), paramyotonia, rhabdomyolysis, paroxysmal dystonia, myasthenia syndromes, malignant hyperthermia, sodium channel toxin related illnesses, cancer pain, restless leg syndrome, fibromyalgia, and neurodegenerative disease, as well as other neurological disorders including multiple sclerosis, wherein the method comprises administering to the mammal in need thereof a therapeutically effective amount of a pharmaceutical composition of the invention as set forth above.

In another aspect, the invention provides a method of treating a range of sodium channel-mediated diseases or condition, preferably neuronal voltage-gated sodium channel-mediated diseases or condition, in a mammal, preferably a human, wherein the diseases or conditions are selected from, but are not limited to, neuroprotection under ischaemic conditions caused by stroke or neural trauma, neurodegenerative disease, as well as other neurological disorders including multiple sclerosis, wherein the method comprises administering to the mammal in need thereof a therapeutically effective amount of a pharmaceutical composition of the invention as set forth above.

In another aspect, the invention provides a method of treating a range of sodium channel-mediated diseases or conditions, preferably neuronal voltage-gated sodium channel-mediated diseases or conditions, in a mammal, preferably a human, wherein the diseases or conditions are selected from, but are not limited to, pruritis (itch), dermatitis, contact dermatitis, allergic dermatitis, eczema, acne, and inflammatory skin disorders, wherein the method comprises administering to the mammal in need thereof a therapeutically effective amount of a pharmaceutical composition of the invention as set forth above.

In another aspect, the invention provides a method of treating a range of sodium channel-mediated diseases or condition, preferably neuronal voltage-gated sodium channel-mediate diseases or condition, in a mammal, preferably a human, through inhibition of ion flux through a voltage-dependent sodium channel in the mammal, preferably a neuronal voltage-gated sodium channel, wherein the method comprises administering to the mammal in need thereof a therapeutically effective amount of a pharmaceutical composition of the invention as set forth above.

A further aspect of this invention is a process for the preparation of the pharmaceutical composition of this invention.

Specific embodiments of these aspects of the invention are described in more detail below.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Definitions

Figure 1:
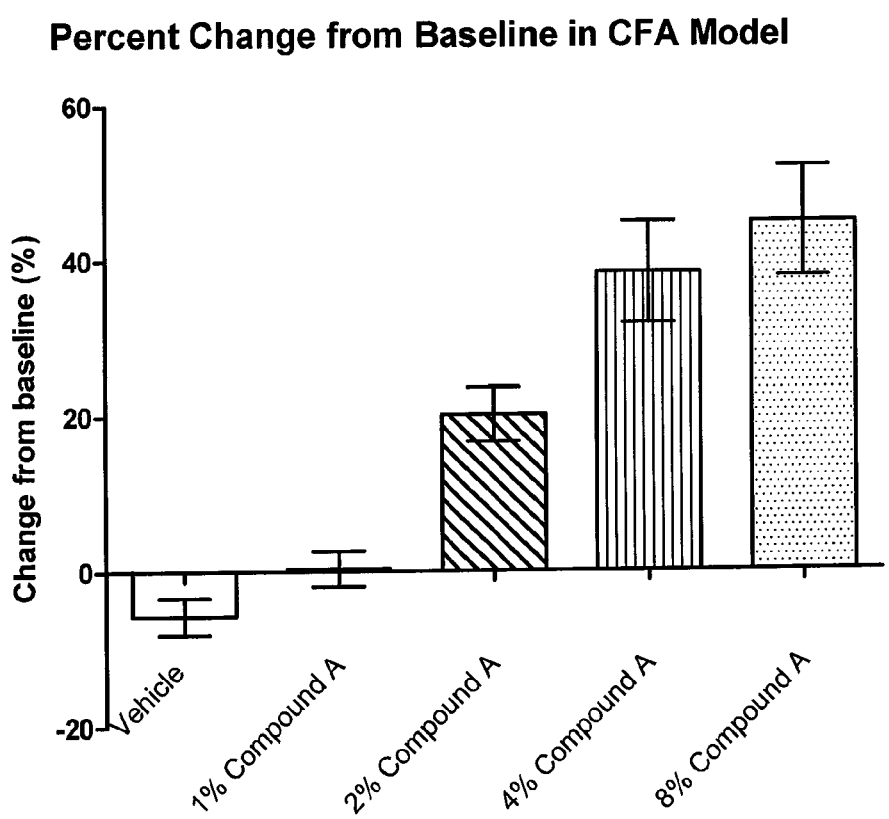
FIG. 1 is a graph showing the mean percent change from baseline (CFB) for each dosage group described in the CFA-induced chronic inflammatory pain study in Example 1. Data are expressed as Mean±SD change from baseline values.

Unless defined otherwise in the specification, the following terms and phrases shall have the following meaning:

"Spiro-oxindole compound" refers to a compound having the following formula:

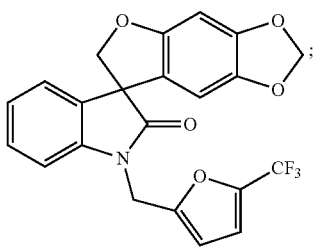 [SMILES: O=C1N(Cc2ccc(C(F)(F)F)o2)c2ccccc2C12COc1cc3c(cc12)OCO3]

or a pharmaceutically acceptable salt thereof. This compound is disclosed in PCT Published Patent Application No. WO 06/110917, which is incorporated in full by reference herein. The spiro-oxindole compound may exist as a single enantiomer, a racemate or as a non-racemic mixture of enantiomers. One of the enantiomers of the spiro-oxindole compound has the following formula:

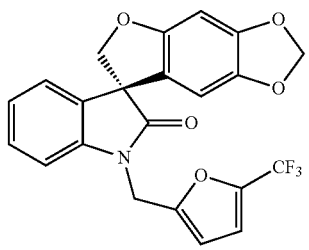 [SMILES: O=C1N(Cc2ccc(C(F)(F)F)o2)c2ccccc2[C@]12COc1cc3c(cc12)OCO3]

and is named herein as (S)-1'-{[5-(trifluoromethyl)furan-2-yl]methyl}spiro[furo[2,3-f][1,3]benzodioxole-7,3'-indol]-2'(1'H)-one. This enantiomer is also identified herein as "COMPOUND A". The use of the "COMPOUND A" identifier herein is intended to include the enantiomer as a free base or as a pharmaceutically acceptable salt.

The term "about" when placed before a numerical value "X" herein refers to an interval extending from X minus 10% of X to X plus 10% of X and preferably to an interval extending from X minus 5% of X to X plus 5% of X.

The expression "% w/w" refers to a percentage by weight compared to the total weight of the composition being considered.

The expression "% w/v" refers to a weight of a solute in a given volume of solvent. For example, 50% w/v of PEG is 50 grams of PEG in 100 mL solvent "Clathrates" refers to substances which fix gases, liquids or compounds as inclusion complexes so that the complex may be handled in solid form and the included constituent (or "guest" molecule) subsequently releases by the action of a solvent or by melting. The term "clathrate" can be used interchangeably with the phrase "inclusion molecule" or with the phrase "inclusion complex". Clathrates contemplated for use in the instant invention are prepared from cyclodextrins. Cyclodextrins are widely known as having the ability to form clathrates (i.e., inclusion compounds) with a variety of molecules. See, for example, *Inclusion Compounds*, edited by J. L. Atwood, J. E. D. Davies, and D. D. MacNicol, London, Orlando, Academic Press, 1984; Goldberg, I., "The Significance of Molecular Type, Shape and Complementarity in Clathrate Inclusion", *Topics in Current Chemistry* (1988), Vol. 149, pp. 2-44; Weber, E. et al., "Functional Group Assisted Clathrate Formation—Scissor-Like and Roof-Shaped Host Molecules", *Topics in Current Chemistry* (1988), Vol. 149, pp. 45-135; and MacNicol, D. D. et al., "Clathrates and Molecular Inclusion Phenomena", *Chemical Society Reviews* (1978), Vol. 7, No. 1, pp. 65-87. Conversion into cyclodextrin clathrates is known to increase the stability and solubility of certain compounds, thereby facilitating their use as pharmaceutical agents. See, for example, Saenger, W., "Cyclodextrin Inclusion Compounds in Research and Industry", *Angew. Chem. Int. Ed. Engl.* (1980), Vol. 19, pp. 344-362; U.S. Pat. No. 4,886,788 (Schering AG); U.S. Pat. No. 6,355,627 (Takasago); U.S. Pat. No. 6,288,119 (Ono Pharmaceuticals); U.S. Pat. No. 614,969 (Ono Pharmaceuticals); U.S. Pat. No. 6,235,780 (Ono Pharmaceuticals); U.S. Pat. No. 6,262,293 (Ono Pharmaceuticals); U.S. Pat. No. 6,225,347 (Ono Pharmaceuticals); and U.S. Pat. No. 4,935,446 (Ono Pharmaceuticals).

"Mammal" includes humans and both domestic animals such as laboratory animals and household pets, (e.g., cats, dogs, swine, cattle, sheep, goats, horses, and rabbits), and non-domestic animals such as wildlife and the like.

"Pharmaceutically acceptable excipient" or "excipient" includes without limitation any inactive material that is combined with a spiro-oxindole compound of the invention in order to produce a drug dosage form for topical administration. The term "pharmaceutically acceptable excipient" is intended to include, but is not limited to, any solvents, penetration enhancing agents, antioxidants, stiffening agents (i.e., thickeners), ointment bases, protectives, adsorbents, demulcents, emollients, preservatives, moisturizers, buffers, adjuvants, bioavailability enhancers, carriers, glidants, sweetening agents, diluents, dye/colorants, flavor enhancers, solubilizers (including surfactants), wetting agents, dispersing agents, suspending agents, stabilizers and isotonic agents, which have been approved by a regulatory agency, such as for example, but is not limited to, the United States Food and Drug Administration, the European Medicines Agency or Health Canada, as being acceptable for use in a formulation for the topical administration of a pharmacologically active ingredient, and/or are considered as Generally Recognized As Safe materials (GRAS materials), and/or are listed in the Inactive Ingredients Guide published by the United States Food and Drug Administration. "Pharmaceutically acceptable excipient" can also comprise the acceptable excipients listed in *Remington: The Science and Practice of Pharmacy, Fox*, 21$^{st}$ ed. 2005. Exemplary pharmaceutically acceptable excipients include, but are not limited to, the following:

ascorbic acid and esters;
    benzyl alcohol;
    benzyl benzoate;
    butylated hydroxytoluene ("BHT");
    butylated hydroxyanisole ("BHA");
    caprylic/capric triglyceride;
    cetyl alcohol;
    chelating agents (e.g., EDTA and citric acid);
    cholesterol;
    cross-linked acrylic acid based polymers (e.g., Carbopol®);
    decyl methyl sulfoxide;
    diethyl sebacate;
    dimethylamine ("DMA");
    dimethicone;
    dimethyl sulfoxide;
    diethylene glycol mono ether (e.g., Transcutol® P);
    diisopropyl adipate (e.g., Ceraphyl® 230);
    ethanol;
    flavinoid;

glutathione;
glycerine;
glycerol oleate/propylene glycol (e.g., Arlacel 186);
glycerol monooleate;
glyceryl caprylate/caprate and PEG-8 (polyethylene glycol) caprylate/caprate complex; carpylocaproyl macrogolglycerides (e.g., Labrasol®);
glyceryl monocaprylate (e.g., Capmul® MCM C8);
glyceryl monolinoleate (e.g., Maisine™ 35-1);
glyceryl monooleate (e.g., Peceol™);
glyceryl monostearate;
hexylene glycol;
hydroxypropyl-β-cyclodextrin (HP-β-CD);
isopropyl alcohol;
isopropyl myristate;
laurocapram; (e.g., Azone®);
lauroyl macrogol-32 glycerides (e.g. Gelucire® 44/14);
macrogol-15 hydroxystearate (e.g., Solutol® HS15);
medium chain triglycerides (e.g., Miglyol® 810, Miglyol® 840 or Miglyol® 812);
methyl laurate;
N-methyl-2-pyrrolidine (e.g., Pharmasolve®);
mineral oil;
mono diglycerides (e.g., Capmul® MCM);
octyldodecanol;
oleic acid;
oleyl alcohol;
peanut oil;
1,2-pentanediol;
polysorbates (e.g., Tween® 80);
polyethylene glycol (e.g., PEG-8, PEG 400, PEG1000, PEG 3350, PEG 6000, or Lutrol® E 400);
polyoxyl 35 castor oil (e.g., Cremophor® EL);
polyoxyl 40 hydrogenated castor oil (e.g., Cremophor® RH 40);
propylene glycol;
propylene glycol diacetate;
propylene glycol monocaprylate (e.g., Capmul PG-8, Capryol 90);
propylene glycol monolaurate (e.g., Capmul PG-12);
propylene glycol monooleate;
2-pyrrolidone;
soybean oil;
stearyl alcohol;
sulfobutylether-β-cyclodextrin (e.g., Capitsol®);
tocopherols (e.g., Vitamin E acetate);
α-tocopherol polyethylene glycol succinate (TPGS);
water; and
white petrolatum.

Additional pharmaceutically acceptable excipients are disclosed herein.

"Solvents" refer to substances that readily dissolve other substances, such as a spiro-oxindole compound of the invention, in order to form a solution. Suitable solvents for the purposes of this invention include polyethylene glycol (e.g., PEG 400, PEG 100, and PEG 3350), diethylene glycol monoethyl ether (e.g., Transcutol®), Tween 80, alcohols (e.g., oleyl alcohol, and stearyl alcohol), Labrasol®, caprylic/capric triglyceride, fatty acid esters (e.g., isopropyl myristate, and diisopropyl adipate (e.g., Ceraphyl® 230)), diethyl sebacate, propylene glycol monocaprylate (e.g., Capmul® PG-8), propylene glycol laurate (e.g., Capmul® PG-12), mono diglycerides (e.g., Capmul® MCM), glyceryl monocaprylate (e.g., Capmul® MCM C8), medium chain triglycerides, hexylene glycol, glyceryl mono-oleate (e.g., Peceol™), 1,2-pentanediol, octyldodecanol, glyceryl monolinoleate (e.g., Maisine™ 35-1), isopropyl alcohol, glycerol oleate/propylene glycol (e.g., Arlacel® 186), mineral oil, water, and glycerine.

"Penetration enhancing agents" refer to substances that increase the permeability of the skin or mucosa to a pharmacologically active ingredient, preferably a spiro-oxindole compound of the invention, so as to increase the rate at which the active ingredient permeates through the skin or mucosa of a mammal, preferably a human. Suitable penetration enhancing agents for the purposes of this invention include, but are not limited to, dimethyl sulfoxide (DMSO), decylmethylsulfoxide, laurocapram (e.g., Azone®), pyrrolidones (e.g., 2-pyrrolidone, and N-methyl-2-pyrrolidine (Pharmasolve®)), surfactants, alcohols (e.g., oleyl alcohol), oleic acid, polyethylene glycol (e.g., PEG 400), diethylene glycol monoethyl ether (e.g., Transcutol®), and fatty acid esters (e.g., isopropyl myristate, methyl laurate, glycerol monooleate, and propylene glycol monooleate). A penetration enhancing agent may be used independently or more than one may be used in a pharmaceutical composition of the invention.

"Ointment bases" refers to substances that function as a carrier and enhance penetration into the skin in order to deliver a pharmacologically active ingredient, preferably a spiro-oxindole compound of the invention, to the area to be treated in the mammal, preferably a human. Suitable "ointment bases" for the purposes of this invention include, but are not limited to, polyethylene glycols (e.g., PEG 400 and PEG 3350). An ointment base may be used independently or more than one may be used in a pharmaceutical composition of the invention.

"Stiffening agents" refers to substances which increase the viscosity and/or physical stability of a pharmaceutical composition of the invention. Suitable "stiffening agents" for the purposes of this invention include, but are not limited to, stearyl alcohol, carbopols, dimethicone and polymers. A stiffening agent may be used independently or more than one may be used in a pharmaceutical composition of the invention.

"Antioxidants" refers to substances which are capable of preventing the oxidation of another molecule. Suitable "antioxidants" for the purposes of this invention include, but are not limited to, butylated hydroxytoluene (BHT), butylated hydroxyanisole (BHA), tocopherols (e.g., Vitamin E acetate), flavinoid, glutathione, ascorbic acid and its esters, DMSO, and chelating agents (e.g., EDTA and citric acid).

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

A "pharmaceutical composition" refers to a formulation of a spiro-oxindole compound of the invention and a medium generally accepted in the art for the topical administration of the spiro-oxindole compound to mammals, e.g., humans. Such a medium includes all pharmaceutically acceptable excipients. For purposes of this disclosure, the phrase "pharmaceutical composition" is interchangeable with the phrase "pharmaceutical formulation".

"Sodium channel-mediated disease or condition" refers to a disease or condition which is ameliorated or alleviated upon modulation of the sodium channel and includes, but is not limited to, pain, or post-herpetic neuralgia. Further examples of sodium channel-mediated diseases or conditions are disclosed below.

"Therapeutically effective amount" refers to that amount of a spiro-oxindole compound of the invention or a pharmaceutical composition of the invention which, when administered to a mammal, preferably a human, is sufficient to effect treatment, as defined below, of the indicated disease or condition in the mammal, preferably a human. The amount of the spiro-oxindole compound or the pharmaceutical composition which constitutes a "therapeutically effective amount" will vary depending on the spiro-oxindole compound, the pharmaceutical composition, the nature of the disease or condition and its severity, other conditions (e.g., age, weight, general health) affecting the health of the mammal to be treated, and the manner of administration, as well as upon the potency, bioavailability and in vivo half-life of the components of the pharmaceutical composition used, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

"Analgesia" refers to an absence of pain in response to a stimulus that would normally be painful.

"Allodynia" refers to a condition in which a normally innocuous sensation, such as pressure or light touch, is perceived as being extremely painful.

Embodiments of the Invention

Of the various aspects of the invention set forth above in the Summary of the Invention, certain embodiments are preferred.

Of the pharmaceutical compositions of the invention, as set forth above in the Summary of the Invention, one embodiment is a pharmaceutical composition comprising a therapeutically effective amount of the spiro-oxindole compound, as an enantiomer, a racemate or a non-racemic mixture of enantiomers, or a pharmaceutically acceptable salt thereof, and one or more pharmaceutically acceptable excipients selected from the exemplary list of pharmaceutically acceptable excipients as set forth above in the Definitions.

Another embodiment is a pharmaceutical composition comprising a therapeutically effective amount of the spiro-oxindole compound, as an enantiomer, a racemate or a non-racemic mixture of enantiomers, or a pharmaceutically acceptable salt thereof, and one or more pharmaceutically acceptable excipients, wherein the pharmaceutically acceptable excipients are selected from one or more solvents, optionally from one or more penetration enhancing agents, optionally from one or more stiffening agents, optionally from one or more ointment bases, and optionally from one or more antioxidants.

Another embodiment is a pharmaceutical composition comprising a therapeutically effective amount of the spiro-oxindole compound, as an enantiomer, a racemate or a non-racemic mixture of enantiomers, or a pharmaceutically acceptable salt thereof, and two or more pharmaceutically acceptable excipients, wherein the pharmaceutically acceptable excipients are selected from one or more solvents, optionally from one or more penetration enhancing agents, optionally from one or more stiffening agents, optionally from one or more ointment bases, and optionally from one or more antioxidants.

Another embodiment is a pharmaceutical composition comprising a therapeutically effective amount of the spiro-oxindole compound, as an enantiomer, a racemate or a non-racemic mixture of enantiomers, or a pharmaceutically acceptable salt thereof, and two or more pharmaceutically acceptable excipients, wherein the pharmaceutically acceptable excipients are selected from one or more solvents, from one or more penetration enhancing agents, from one or more stiffening agents, from one or more ointment bases, and optionally from one or more antioxidants.

Another embodiment is a pharmaceutical composition comprising a therapeutically effective amount of the spiro-oxindole compound, as an enantiomer, a racemate or a non-racemic mixture of enantiomers, or a pharmaceutically acceptable salt thereof, and one or more pharmaceutically acceptable excipients, wherein one of the pharmaceutically acceptable excipients is a solvent selected from polyethylene glycol, diethylene glycol monoethyl ether, polysorbates, alcohols, carpylocaproyl macrogolglycerides, caprylic/capric triglyceride, fatty acid esters, diethyl sebacate, propylene glycol monocaprylate, propylene glycol laurate, mono diglycerides, glyceryl monocaprylate, medium chain triglycerides, hexylene glycol, glyceryl monooleate, 1,2-pentanediol, octyldodecanol, glyceryl mono-linoleate, glycerol oleate/propylene glycol, mineral oil, water, or glycerine.

Another embodiment is a pharmaceutical composition comprising a therapeutically effective amount of the spiro-oxindole compound, as an enantiomer, a racemate or a non-racemic mixture of enantiomers, or a pharmaceutically acceptable salt thereof, and one or more pharmaceutically acceptable excipients, wherein one of the pharmaceutically acceptable excipients is a penetration enhancing agent selected from dimethyl sulfoxide, decylmethylsulfoxide, laurocapram, pyrrolidones, surfactants, alcohols, oleic acid, polyethylene glycol, diethylene glycol monoethyl ether, or fatty acid esters.

Another embodiment is a pharmaceutical composition comprising a therapeutically effective amount of the spiro-oxindole compound, as an enantiomer, a racemate or a non-racemic mixture of enantiomers, or a pharmaceutically acceptable salt thereof, and one or more pharmaceutically acceptable excipients, wherein one of the pharmaceutically acceptable excipients is a stiffening agent selected from stearyl alcohol, carbopols, dimethicone or polymers.

Another embodiment is a pharmaceutical composition comprising a therapeutically effective amount of the spiro-oxindole compound, as an enantiomer, a racemate or a non-racemic mixture of enantiomers, or a pharmaceutically acceptable salt thereof, and one or more pharmaceutically acceptable excipients, wherein one of the pharmaceutically acceptable excipients is an ointment base selected from polyethylene glycols.

Another embodiment is a pharmaceutical composition comprising a therapeutically effective amount of the spiro-oxindole compound, as an enantiomer, a racemate or a non-racemic mixture of enantiomers, or a pharmaceutically acceptable salt thereof, and one or more pharmaceutically acceptable excipients, wherein one of the pharmaceutically acceptable excipients is an antioxidant selected from butylated hydroxytoluene, butylated hydroxyanisole, tocopherols, flavinoid, glutathione, ascorbic acid and esters, dimethyl sulfoxide, or chelating agents.

Another embodiment is a pharmaceutical composition comprising a therapeutically effective amount of the spiro-oxindole compound, as an enantiomer, a racemate or a non-racemic mixture of enantiomers, or a pharmaceutically acceptable salt thereof, and one or more pharmaceutically acceptable excipients, wherein each pharmaceutically acceptable excipient is present in a concentration of from about 0.01% w/w to about 99% w/w.

Another embodiment is a pharmaceutical composition comprising a therapeutically effective amount of the spiro-oxindole compound, as an enantiomer, a racemate or a non-racemic mixture of enantiomers, or a pharmaceutically acceptable salt thereof, and one or more pharmaceutically acceptable excipients, wherein a first pharmaceutically acceptable excipient is a solvent present at a concentration of from about 30% w/w to about 70% w/w, a second pharmaceutically acceptable excipient is a penetration enhancing agent present in a concentration of from about 2% w/w to about 25% w/w, a third pharmaceutically acceptable excipient is a penetration enhancing agent present in a concentration of from about 1% w/w to about 10% w/w, a fourth pharmaceutically acceptable excipient is a penetration enhancing agent present in a concentration of from about 1% w/w to about 25% w/w, a fifth pharmaceutically acceptable excipient is a stiffening agent present in a concentration of from about 0.1% w/w to about 10% w/w, a sixth pharmaceutically acceptable excipient is an antioxidant present in a concentration of from about 0.01% w/w to about 2% w/w, and a seventh pharmaceutically acceptable excipient is an ointment base present in a concentration of from about 10% w/w to about 50% w/w.

Another embodiment is a pharmaceutical composition comprising a therapeutically effective amount of the spiro-oxindole compound, as an enantiomer, a racemate or a non-racemic mixture of enantiomers, or a pharmaceutically acceptable salt thereof, and one or more pharmaceutically acceptable excipients, wherein a first pharmaceutically acceptable excipient is a solvent present at a concentration of from about 45% w/w to about 55% w/w, a second pharmaceutically acceptable excipient is a penetration enhancing agent present in a concentration of from about 5% w/w to about 15% w/w, a third pharmaceutically acceptable excipient is a penetration enhancing agent present in a concentration of from about 2.5% w/w to about 7.5% w/w, a fourth pharmaceutically acceptable excipient is a penetration enhancing agent present in a concentration of from about 2.5% w/w to about 7.5% w/w, a fifth pharmaceutically acceptable excipient is a stiffening agent present in a concentration of from about 0.1% w/w to about 7.5% w/w, a sixth pharmaceutically acceptable excipient is an antioxidant present in a concentration of from about 0.05% w/w/to about 1% w/w, and a seventh pharmaceutically acceptable excipient is an ointment base present in a concentration of from about 15% w/w to about 30% w/w.

Another embodiment is a pharmaceutical composition comprising a therapeutically effective amount of the spiro-oxindole compound, as an enantiomer, a racemate or a non-racemic mixture of enantiomers, or a pharmaceutically acceptable salt thereof, and one or more pharmaceutically acceptable excipients selected from a solvent selected from PEG 400 or PEG 3350; one or more penetration enhancing agents selected from Transcutol® P, oleyl alcohol or isopropyl myristate; a stiffening agent selected from stearyl alcohol; an ointment base selected from PEG 400 or PEG 3350; and an antioxidant selected from butylated hydroxytoluene.

Of this embodiment, a further embodiment is a pharmaceutical composition comprising a therapeutically effective amount of the spiro-oxindole compound, as an enantiomer, a racemate or a non-racemic mixture of enantiomers, or a pharmaceutically acceptable salt thereof, wherein PEG 400 is present in a concentration of from about 30% w/w to about 70% w/w, Transcutol® P is present in a concentration of from about 2% w/w to about 25% w/w, oleyl alcohol is present in a concentration of from about 1% w/w to about 10% w/w, isopropyl myristate is present in a concentration of from about 1% w/w to about 25% w/w, stearyl alcohol is present in a concentration of from about 0.1% w/w to about 10% w/w, BHT is present in a concentration of from about 0.01% w/w to about 2% w/w, and PEG 3350 is present in a concentration of from about 10% w/w to about 50% w/w.

Of this embodiment, a further embodiment is a pharmaceutical composition comprising a therapeutically effective amount of the spiro-oxindole compound, as an enantiomer, a racemate or a non-racemic mixture of enantiomers, or a pharmaceutically acceptable salt thereof, wherein PEG 400 is present in a concentration of from about 45% w/w to about 55% w/w, Transcutol® P is present in a concentration of from about 5% w/w to about 15% w/w, oleyl alcohol is present in a concentration of from about 2.5% w/w to about 7.5% w/w, isopropyl is myristate present in a concentration of from about 2.5% w/w to about 7.5% w/w, stearyl alcohol is present in a concentration of from about 0.1% w/w to about 7.5% w/w, BHT is present in a concentration of from about 0.05% w/w to about 1% w/w, and PEG 3350 is present in a concentration of from about 15% w/w to about 30% w/w.

Of all of the above embodiments, a further embodiment is wherein the spiro-oxindole compound is present in a concentration of from about 0.1% w/w to about 10% w/w.

Of this embodiment, a further embodiment is wherein the spiro-oxindole compound is present in a concentration of from about 2% w/w to about 8% w/w.

Of all of the above embodiments, a further embodiment is wherein the pharmaceutical composition comprises the spiro-oxindole compound at a concentration of 2.0% w/w; PEG 400 at a concentration of 52.9% w/w; Transcutol® P at a concentration of 10% w/w; oleyl alcohol at a concentration of 5% w/w; isopropyl myristate at a concentration of 5% w/w; stearyl alcohol at a concentration of 5% w/w; butylated hydroxytoluene at a concentration of 0.1% w/w; and PEG 3350 at a concentration of 20% w/w of the pharmaceutical composition.

Of all of the above embodiments, another further embodiment is wherein the pharmaceutical composition comprises the spiro-oxindole compound at a concentration of 4% w/w; PEG 400 at a concentration of 50.9% w/w; Transcutol® P at a concentration of 10% w/w; oleyl alcohol at a concentration of 5% w/w; isopropyl myristate at a concentration of 5% w/w; stearyl alcohol at a concentration of 5% w/w; butylated hydroxytoluene at a concentration of 0.1% w/w; and PEG 3350 at a concentration of 20% w/w of the pharmaceutical composition.

Of all of the above embodiments, another further embodiment is wherein the pharmaceutical composition comprises the spiro-oxindole compound at a concentration of 4% w/w; PEG 400 at a concentration of 50.9% w/w; Transcutol® P at a concentration of 5% w/w; oleyl alcohol at a concentration of 5% w/w; isopropyl myristate at a concentration of 5% w/w; stearyl alcohol at a concentration of 10% w/w; butylated hydroxytoluene at a concentration of 0.1% w/w; and PEG 3350 at a concentration of 20% w/w of the pharmaceutical composition.

Of all of the above embodiments, another further embodiment is wherein the pharmaceutical composition comprises the spiro-oxindole compound at a concentration of 8% w/w; PEG 400 at a concentration of 46.9% w/w; Transcutol® P at a concentration of 10% w/w; oleyl alcohol at a concentration of 5% w/w; isopropyl myristate at a concentration of 5% w/w; stearyl alcohol at a concentration of 5% w/w; butylated hydroxytoluene at a concentration of 0.1% w/w; and PEG 3350 at a concentration of 20% w/w of the pharmaceutical composition.

Of all of the above embodiments, a further embodiment is wherein the spiro-oxindole compound is a compound of the following formula:

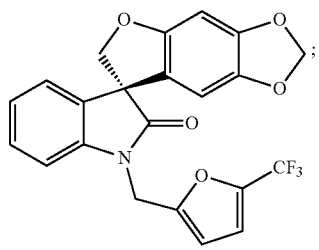 [SMILES: O=C1N(Cc2ccc(C(F)(F)F)o2)c2ccccc2[C@]12COc1cc3c(cc12)OCO3]

or a pharmaceutically acceptable salt thereof.

Of the methods of treating, preventing or ameliorating a sodium channel-mediated disease or a condition in a mammal, as set forth above in the Summary of the Invention, one embodiment comprises topically administering to the mammal, preferably a human, in need thereof a therapeutically effective amount of the pharmaceutical composition of any of the above embodiments of pharmaceutical compositions of the invention.

Of this embodiment, a further embodiment is wherein the wherein said disease or condition is selected from the group consisting of neuropathic pain, inflammatory pain, visceral pain, post-herpetic neuralgia, cancer pain, chemotherapy pain, trauma pain, surgical pain, post-operative pain, pruritis, osteoarthritis, trigeminal neuralgia, familial erythromelalgia, primary erythromelalgia, familial rectal pain, childbirth pain, labor pain, neurogenic bladder, ulcerative colitis, chronic pain, persistent pain, peripherally mediated pain, centrally mediated pain, chronic headache, migraine headache, sinus headache, tension headache, phantom limb pain, peripheral nerve injury, and combinations thereof.

Specific embodiments of the pharmaceutical compositions of the invention and methods of using the pharmaceutical compositions of the invention are described in more detail below.

Utility of the Pharmaceutical Compositions of the Invention

This invention is directed to pharmaceutical compositions comprising one or more pharmaceutically acceptable excipients and a therapeutically effective amount of the spiro-oxindole compound, or a pharmaceutically acceptable salt thereof, for use in the treatment of sodium channel-mediated diseases or conditions, preferably diseases or conditions related to pain, such as for example, post-herpetic neuralgia, osteoarthritis, and persistent post-operative pain, in a mammal by topically administering a therapeutically effective amount of the pharmaceutical composition to the mammal, preferably a human, in need thereof.

Sodium channel-mediated diseases or conditions of particular interest to the invention are those disease or conditions which are ameliorated or alleviated by the modulation, preferably the inhibition (or blocking), of the sodium channel. Preferably the sodium channel-mediated diseases or conditions of the invention are those diseases or conditions which are ameliorated or alleviated by the modulation, preferably the inhibition (or blocking) of neuronal voltage-gated sodium channels ($Na_v$'s), including, but not limited to, pain or post-herpetic neuralgia.

Accordingly, the invention provides a method of treating a range of sodium channel-mediated diseases or conditions in a mammal, preferably a human, wherein the diseases or conditions are selected from, but are not limited to, pain, post-herpetic neuralgia (PHN), post-operative pain, pruritis, pain associated with HIV, HIV treatment induced neuropathy, trigeminal neuralgia, familial erythromelalgia, primary erythromelalgia, familial rectal pain, eudynia, heat sensitivity, pain associated with multiple sclerosis (MS), amyotrophic lateral sclerosis (ALS), painful diabetic neuropathy, peripheral neuropathy, arthritis, rheumatoid arthritis, osteoarthritis, tendonitis, bursitis, musculoskeletal sprains, tenosinovitis, chondromalacia patellae, myositis, myotonia (including but not limited to SCN4A-related myotonia), paramyotonia, rhabdomyolysis, paroxysmal dystonia, myasthenia syndromes, malignant hyperthermia, sodium channel toxin related illnesses, cancer pain, restless leg syndrome, fibromyalgia, and neurodegenerative disease, as well as other neurological disorders including multiple sclerosis, by administering to the mammal a therapeutically effective amount of a pharmaceutical composition of the invention.

For purposes of this invention and unless otherwise specifically defined herein, the term "pain" refers to all categories of pain and is recognized to include, but is not limited to, neuropathic pain, inflammatory pain, nociceptive pain, idiopathic pain, neuralgic pain, orofacial pain, burn pain, somatic pain, visceral pain, myofacial pain, dental pain, cancer pain, chemotherapy pain, trauma pain, surgical pain, post-surgical pain, childbirth pain, labor pain, reflex sympathetic dystrophy, brachial plexus avulsion, acute pain (e.g., musculoskeletal and post-operative pain), chronic pain, persistent pain, peripherally mediated pain, centrally mediated pain, conditions associated with cephalic pain, phantom limb pain, peripheral nerve injury, pain following stroke, thalamic lesions, radiculopathy, HIV pain, post-herpetic pain, and combinations thereof.

Pruritis, commonly known as itch and also known as pruritus, is a common dermatological condition. While the exact causes of pruritis are complex and poorly understood, there has long been acknowledged to be mediated by sensory neurons some of which also mediate pain responses. In particular, it is believed that sodium channels likely communicate or propagate along the nerve axon the itch signals along the skin. Transmission of the itch impulses results in the unpleasant sensation that elicits the desire or reflex to scratch.

From a neurobiology level, it is believed that there is a shared complexity of specific mediators, related neuronal pathways and the central processes of itch and pain and recent data suggest that there is a broad overlap between pain- and itch-related peripheral mediators and/or receptors (Ikoma et al., *Nature Reviews Neuroscience*, 7:535-547, 2006). Remarkably, pain and itch have similar mechanisms of neuronal sensitization in the peripheral nervous system and the central nervous system but exhibits intriguing differences as well.

For example, the mildly painful stimuli from scratching are effective in abolishing the itch sensation. In contrast, analgesics such as opioids can generate severe pruritis. The antagonistic interaction between pain and itch can be exploited in pruritis therapy, and current research concentrates on the identification of common targets for future analgesic and antipruritis therapy. COMPOUND A, or a pharmaceutically acceptable salt thereof, has been shown to have analgesic effects in a number of animal models at oral doses ranging from 1 mg/Kg to 100 mg/Kg. Accordingly, COMPOUND A, as an enantiomer or a pharmaceutically acceptable salt thereof, can also be useful for treating pruritis.

The types of pruritis, include, but are not limited to:

a) psoriatic pruritis, itch due to hemodialysis, and itching caused by skin disorders (e.g., dermatitis), systemic disorders, neuropathy, psychogenic factors or a mixture thereof;

b) itch caused by allergic reactions, insect bites, hypersensitivity (e.g., dry skin, eczema, psoriasis), acne, inflammatory conditions or injury;

c) skin irritation or inflammatory effect from administration of another therapeutic such as, for example, antibiotics, antivirals and antihistamines; and d) itch caused by viral infections, such as itch associated with post-herpetic neuralgias.

The general utility of the spiro-oxindole compound, or a pharmaceutically acceptable salt thereof, of the invention as a sodium channel blocker is described in PCT Published Patent Application No. WO 06/110917. In particular, the general utility of the spiro-oxindole compound, or a pharmaceutically acceptable salt thereof, used in the pharmaceutical compositions of the invention in mediating, especially inhibiting, the sodium channel ion flux has been determined using the assays described in PCT Published Patent Application No. WO 06/110917. The general utility of COMPOUND A, or a pharmaceutically acceptable salt, used in the pharmaceutical compositions of the invention in treating sodium-channel mediated diseases or conditions may be established in industry standard animal models and in the animal models disclosed in PCT Published Patent Application No. WO 06/110917 for demonstrating the efficacy of the spiro-oxindole compound, or a pharmaceutically acceptable salt thereof, in treating such diseases and conditions.

Accordingly, this invention provides a method of treating a range of sodium channel-mediated diseases or condition, preferably neuronal voltage-gated sodium channel-mediate diseases or condition, in a mammal, preferably a human, through inhibition of ion flux through a voltage-dependent sodium channel in the mammal, preferably a neuronal voltage-gated sodium channel, wherein the method comprises administering to the mammal in need thereof a therapeutically effective amount of a pharmaceutical composition of the invention as set forth above.

As noted above, the pharmaceutical compositions of the invention are useful in treating sodium channel-mediated diseases or conditions, preferably neuronal voltage-gated sodium channel-mediated diseases or conditions. In particular, the pharmaceutical compositions of the invention are useful in treating or lessening the severity of a disease or condition where activation or hyperactivity of one or more of neuronal voltage-gated sodium channels selected from $Na_v1.1$, $Na_v1.2$, $Na_v1.3$, $Na_v1.4$, $Na_v1.5$, $Na_v1.6$, $Na_v1.7$, $Na_v1.8$, or $Na_v1.9$ is implicated in the disease or condition. Preferably, the pharmaceutical compositions of the invention are useful in treating or lessening the severity of a disease or condition where activation or hyperactivity of $Na_v1.7$ is implicated in the disease or condition, such as pain or post-herpetic neuralgia.

Accordingly, the invention provides a method for treating or lessening the severity of a disease, condition, or disorder where activation or hyperactivity of one or more of neuronal voltage-gated sodium channels selected from $Na_v1.1$, $Na_v1.2$, $Na_v1.3$, $Na_v1.4$, $Na_v1.5$, $Na_v1.6$, $Na_v1.7$, $Na_v1.8$, or $Na_v1.9$ is implicated in the disease, condition or disorder, wherein the methods comprise administering to the mammal in need thereof a therapeutically effective amount of a pharmaceutical composition of the invention as set forth above.

Further disclosure of the utility of the pharmaceutical compositions of the invention is set forth below.

Preparation of the Spiro-Oxindole Compound of the Invention

The spiro-oxindole compound, as an enantiomer, a racemate or a non-racemic mixture of enantiomers, or a pharmaceutically acceptable salt thereof, used in the pharmaceutical compositions of the invention can be prepared by the methods disclosed in PCT Published Patent Application No. WO 06/110917, or by methods known to one skilled in the art. COMPOUND A and its corresponding (R)-enantiomer, and their pharmaceutically acceptable salts, can be prepared by the methods disclosed in PCT Published Patent Application No. WO 2011/002708, the relevant disclosure of which is disclosed herein in its entirety, or by methods known to one skilled in the art.

COMPOUND A, or a pharmaceutically acceptable salt thereof, and its corresponding (R)-enantiomer can be prepared by the resolution of the spiro-oxindole compound using either chiral high pressure liquid chromatography methods or by simulated moving bed chromatography methods, as described below in the following Reaction Scheme wherein "chiral HPLC" refers to chiral high pressure liquid chromatography and "SMB" refers to simulated moving bed chromatography:

REACTION SCHEME

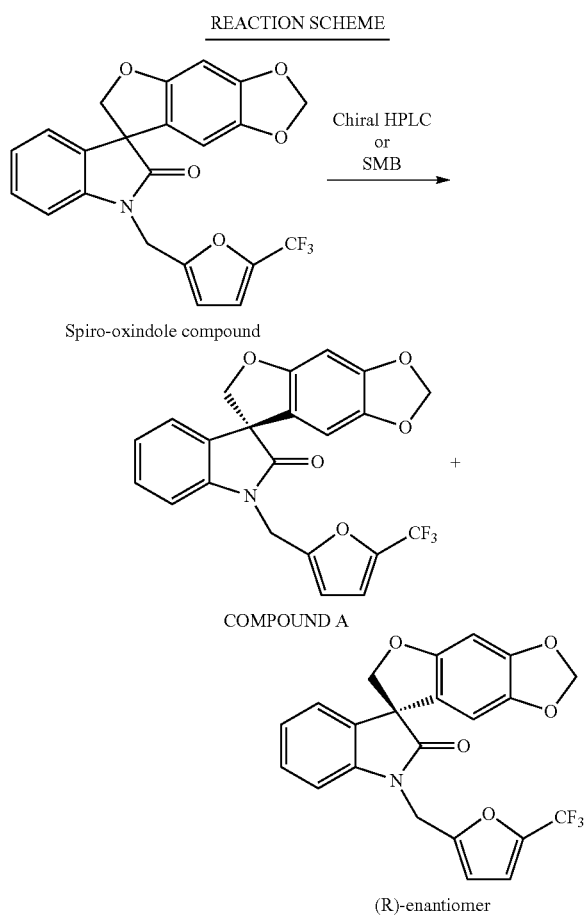

One of ordinary skill in the art would recognize variations in the above Reaction Scheme which are appropriate for the resolution of the individual enantiomers.

Alternatively, COMPOUND A and its corresponding (R)-enantiomer can be synthesized from chiral starting materials which are known or readily prepared using process analogous to those which are known.

Preferably, COMPOUND A obtained by the resolution methods disclosed herein is substantially free of the (R)-enantiomer or contains only traces of the (R)-enantiomer.

The following Synthetic Examples serve to illustrate the resolution methods disclosed by the above Reaction Scheme and are not intended to limit the scope of the invention.

Synthetic Example 1

Synthesis of 1'-{[5-(trifluoromethyl)furan-2-yl]methyl}spiro[furo[2,3-f][1,3]benzodioxole-7,3'-indol]-2'(1H)-one (Spiro-oxindole compound)

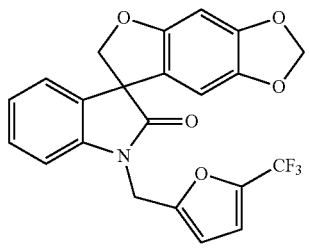 [SMILES: O=C1N(Cc2ccc(C(F)(F)F)o2)c2ccccc2C12COc1cc3c(cc12)OCO3]

To a suspension of spiro[furo[2,3-f][1,3]benzodioxole-7,3'-indol]-2'(1'H)-one (1.0 g, 3.6 mmol), which can be prepared according to the methods disclosed in PCT Published Patent Application No. WO 06/110917, and cesium carbonate (3.52 g, 11 mmol) in acetone (50 mL) was added 2-bromomethyl-5-trifluoromethylfuran (1.13 g, 3.9 mmol) in one portion and the reaction mixture was stirred at 55-60° C. for 16 hours. Upon cooling to ambient temperature, the reaction mixture was filtered and the filtrate was evaporated under reduced pressure. The residue was subjected to column chromatography, eluting with ethyl acetate/hexane (1/9-1/1) to afford 1'-{[5-(trifluoromethyl)furan-2-yl]methyl}spiro[furo[2,3-f][1,3]benzodioxole-7,3'-indol]-2'(1'H)-one, i.e., the Spiro-oxindole compound, (1.17 g, 76%) as a white solid: mp 139-141° C.; $^1$H NMR (300 MHz, CDCl$_3$) δ 7.32-6.97 (m, 5H), 6.72 (d, J=3.24 Hz, 1H), 6.66 (s, 1H), 6.07 (s, 1H), 5.90-5.88 (m, 2H), 5.04 (ABq, 2H), 4.74 (ABq, 2H); $^{13}$C NMR (75 MHz, CDCl$_3$) δ 176.9, 155.7, 153.5, 148.8, 142.2, 141.9, 140.8, 140.2, 139.7, 139.1, 132.1, 129.2, 124.7, 124.1, 123.7, 121.1, 120.1, 117.6, 114.5, 114.4, 110.3, 109.7, 103.0, 101.9, 93.8, 80.0, 57.8, 36.9; MS (ES+) m/z 430.2 (M+1), 452.2 (M+23); Cal'd for $C_{22}H_{14}F_3NO_5$: C, 61.54%; H, 3.29%; N, 3.26%. Found: C, 61.51%; H, 3.29%; N, 3.26%.

Synthetic Example 2

Resolution of the Spiro-Oxindole Compound by Chiral HPLC

The spiro-oxindole compound was resolved into COMPOUND A and the corresponding (R)-enantiomer by chiral HPLC under the following conditions:

Column: Chiralcel® OJ-RH; 20 mm I.D.×250 mm, 5 mic; Lot: OJRH CJ-EH001 (Daicel Chemical Industries, Ltd)
Eluent: Acetonitrile/Water (60/40, v/v, isocratic)
Flow rate: 10 mL/min
Run time: 60 min
Loading: 100 mg of compound of formula (I) in 1 mL of acetonitrile
Temperature: Ambient Under the above chiral HPLC conditions, the (R)-enantiomer, i.e., (R)-1'-{[5-(trifluoromethyl)furan-2-yl]methyl}spiro[furo[2,3-t][1,3]-benzodioxole-7,3'-indol]-2'(1'H)-one, was isolated as the first fraction as a white solid; ee (enantiomeric excess)>99% (analytical OJRH, 55% acetonitrile in water); mp 103-105° C.; $^1$H NMR (300 MHz, DMSO-$d_6$) δ 7.32-6.99 (m, 5H), 6.71 (d, J=3.35 Hz, 1H), 6.67 (s, 1H), 6.05 (s, 1H), 5.89 (ABq, 2H), 5.03 (ABq, 2H), 4.73 (ABq, 2H); $^{13}$C NMR (75 MHz, CDCl$_3$) δ 177.2, 155.9, 152.0, 149.0, 142.4, 142.0, 141.3, 132.0, 129.1, 123.9, 120.6, 119.2, 117.0, 112.6, 109.3, 108.9, 103.0, 101.6, 93.5, 80.3, 58.2, 36.9; MS (ES+) m/z 430.2 (M+1), $[\alpha]_D$-17.46 (c 0.99, DMSO). COMPOUND A, (S)-1'-{[5-(trifluoromethyl)furan-2-yl]methyl}spiro-[furo[2,3-f][1,3]benzodioxole-7,3'-indol]-2'(1'H)-one, was isolated as the second fraction as a white solid; ee>99% (analytical OJRH, 55% acetonitrile in water); mp 100-102° C.; $^1$H NMR (300 MHz, DMSO-$d_6$) δ 7.32-6.99 (m, 5H), 6.71 (d, J=3.43 Hz, 1H), 6.67 (s, 1H), 6.05 (s, 1H), 5.89 (ABq, 2H), 5.03 (ABq, 2H), 4.73 (ABq, 2H); $^{13}$C NMR (75 MHz, CDCl$_3$) δ 177.2, 155.9, 152.0, 149.0, 142.4, 142.0, 141.3, 132.0, 129.1, 123.9, 120.6, 119.2, 117.0, 112.6, 109.3, 108.9, 103.0, 101.6, 93.5, 80.3, 58.2, 36.9; MS (ES+) m/z 430.2 (M+1), $[\alpha]_D$+14.04 (c 0.99, DMSO).

Synthetic Example 3

Resolution of the Spiro-Oxindole Compound by SMB Chromatography

The spiro-oxindole compound was resolved into COMPOUND A and the corresponding (R)-enantiomer by SMB chromatography under the following conditions:
Extract: 147.05 mL/min
Raffinate: 76.13 mL/min
Eluent: 183.18 mL/min
Feed: 40 mL/min
Recycling: 407.88 mL/min
Run Time: 0.57 min
Temperature: 25° C.
Pressure: 46 bar The feed solution (25 g of compound of formula (I) in 1.0 L of mobile phase (25:75:0.1 (v:v:v) mixture of acetonitrile/methanol/trifluoroacetic acid)) was injected continuously into the SMB system (Novasep Licosep Lab Unit), which was equipped with eight identical columns in 2-2-2-2 configuration containing 110 g (per column, 9.6 cm, 4.8 cm I.D.) of chiralpack AD as stationary phase. The first eluting enantiomer (the (R)-enantiomer) was contained in the raffinate stream and the second eluting enantiomer (COMPOUND A) was contained in the extract stream. The characterization data of COMPOUND A and the (R)-enantiomer obtained from the SMB resolution were identical to those obtained above utilizing chiral HPLC.

Preparation of the Pharmaceutical Compositions of the Invention

The preparation of the pharmaceutical compositions of the invention employs conventional techniques of pharmaceutical formulation, medicinal chemistry and the like, which are within the skill of one ordinarily skilled in the art. Such techniques are explained fully in the literature. Preparation of pharmaceutical compositions are described, for example, in *Remington: The Science and Practice of Pharmacy*, 21$^{st}$ edition (Lippincott Williams & Wilkins, (2005) and Ansel et al., *Pharmaceutical Dosage Forms and Drug Delivery Systems*, 8$^{th}$ Ed. (Med, Pa.: Williams & Wilkins, 2005), hereby incorporated by reference.

The pharmaceutical compositions of the invention are preferably in ointment form. Ointments are semisolids that contain little if any water and are typically prepared by mixing the active ingredient with a greasy or non-greasy base with the aid of suitable machinery.

The pharmaceutical compositions of the invention comprise one or more pharmaceutically acceptable excipients.

It is understood that the pharmaceutically acceptable excipients used in any of the topical pharmaceutical compositions of the invention are preferably sterile and/or preferably have been approved by the United States Food and Drug Administration, the European Medicines Agency or Health Canada as being acceptable for use in topical formulations to be administered to humans and animals.

In the preparation of pharmaceutical compositions of the invention, extensive studies, such as solubility and stability, were conducted to provide pharmaceutical compositions which allowed for the desired therapeutically effective amount of the active ingredient, i.e., the spiro-oxindole compound, as an enantiomer, a racemate or a non-racemic mixture of enantiomers, or a pharmaceutically acceptable salt thereof, preferably COMPOUND A, or a pharmaceutically acceptable salt thereof, to be dissolved in one or more pharmaceutically acceptable excipients and which allowed for the active ingredient to be readily solubilized in the pharmaceutical composition, and well-preserved for multiple applications. Furthermore, the pharmaceutical compositions need to be physically and chemically stable at ambient temperature over a suitable period of time, preferably for a period of time from about 1 month to about 5 years, more preferably for a period of time from about 1 year to about 3 years.

The spiro-oxindole compound of the invention, particularly, COMPOUND A, is relatively lipophilic and has poor water solubility. COMPOUND A's water solubility is less than 5 µg/mL. Furthermore, COMPOUND A has a calculated Log P of about 3.07, and does not contain functional groups that can be ionised by pH alteration and consequently varying the pH of a solution to 2, 7.4 and 12 does not change the solubility of COMPOUND A, which remains at <5 µg/mL.

Attempts to improve the solubility of COMPOUND A for use in a topical pharmaceutical composition, preferably as an ointment, were undertaken using a variety of solubilization techniques. The aim was to conduct a thorough investigation of the use of various pharmaceutically acceptable excipients to maximize the solubility of COMPOUND A. A series of solubility studies, which were performed using standard solubility testing techniques, was therefore carried out to identify proper excipient(s) and/or excipient combinations for achieving the target dosage strength for COMPOUND A. The solubility of COMPOUND A in these studies was determined by UV spectrophotometry using COMPOUND A's UV absorbance wavelength at 312 nm.

In addition to the solubility studies undertaken, a series of stability studies were conducted to determine the physical and chemical stability of the pharmaceutical compositions prepared.

Based on the results obtained from the solubility and stability studies and the results obtain from in vivo efficacy studies, the following representative pharmaceutical compositions of the invention were prepared:

TABLE 1

| Component | Function | % (w/w) | % (w/w) | % (w/w) | % (w/w) | % (w/w) |
|---|---|---|---|---|---|---|
| COMPOUND A | Active Ingredient | 1.0 | 2.0 | 4.0 | 4.0 | 8.0 |
| PEG 400 | Solvent and ointment base | 53.9 | 52.9 | 50.9 | 50.9 | 46.9 |
| Transcutol ® P | Penetration enhancer | 10.0 | 10.0 | 5.0 | 10.0 | 10.0 |
| Oleyl alcohol | Penetration enhancer | 5.0 | 5.0 | 5.0 | 5.0 | 5.0 |
| Isopropyl myristate | Penetration enhancer | 5.0 | 5.0 | 5.0 | 5.0 | 5.0 |
| Stearyl alcohol | Stiffening agent | 5.0 | 5.0 | 10.0 | 5.0 | 5.0 |
| Butylated hydroxytoluene (BHT) | Antioxidant | 01 | 0.1 | 0.1 | 0.1 | 0.1 |
| PEG 3350 | Ointment base | 20.0 | 20.0 | 20.0 | 20.0 | 20.0 |
| Total | | 100.0 | 100.0 | 100.0 | 100.0 | 100.0 |

In general, each pharmaceutically acceptable excipient may be present in a pharmaceutical composition of the invention in a concentration of from about 0.5% w/w to about 99.0% w/w. More preferred, each pharmaceutically acceptable excipient may be present in a pharmaceutical composition of the invention in a concentration of from about 1% w/w to about 90% w/w. Even more preferred, each pharmaceutically acceptable excipient may be present in a pharmaceutical composition of the invention in a concentration of from about 10% w/w to about 80.0% w/w.

Preferably, in a pharmaceutical composition of the invention, PEG 400 is present in a concentration of from about 30% w/w to about 70% w/w, Transcutol® P is present in a concentration of from about 2% w/w to about 25% w/w, oleyl alcohol is present in a concentration of from about 1% w/w to about 10% w/w, isopropyl myristate is present in a concentration of from about 1% w/w to about 25% w/w, stearyl alcohol is present in a concentration of from about 0.1% w/w to about 10% w/w, BHT is present in a concentration of from about 0.01% w/w to about 2% w/w, and PEG 3350 is present in a concentration of from about 10% w/w to about 50% w/w.

More preferably, in a pharmaceutical composition of the invention, PEG 400 is present in a concentration of from about 45% w/w to about 55% w/w, Transcutol® P is present in a concentration of from about 5% w/w to about 15% w/w, oleyl alcohol is present in a concentration of from about 2.5% w/w to about 7.5% w/w, isopropyl myristate is present in a concentration of from about 2.5% w/w to about 7.5% w/w, stearyl alcohol is present in a concentration of from about 0.1% w/w to about 7.5% w/w, BHT is present in a concentration of from about 0.05% w/w to about 1% w/w, and PEG 3350 is present in a concentration of from about 15% w/w to about 30% w/w.

Preferably, in a pharmaceutical composition of the invention, the spiro-oxindole compound, as an enantiomer, a racemate or a non-racemic mixture of enantiomers, or a pharmaceutically acceptable salt thereof, is present in a concentration of from about 0.1% w/w to about 10% w/w, and preferably from about 2% w/w to about 8% w/w.

The stability of the pharmaceutical compositions disclosed herein may be tested in conventional manner, e.g., by measurement of COMPOUND A, or a pharmaceutically acceptable salt thereof, and its degradation products, dissolution, friability, disintegration time, microbial content, appearance and/or microscopy, for defined periods of time.

Preferably, the pharmaceutical compositions of this invention will be stable for a time period of between about 1 month and about 5 years when kept at a temperature between about 5° C. and about 50° C. More preferably, the pharmaceutical compositions of this invention will be stable for a time period of between about 6 months and about 4 years when kept at a temperature between about 15° C. and about 45° C. Even more preferably, the pharmaceutical compositions of this invention will be stable for a time period of between about 6 months and about 3 years when kept at a temperature between about 25° C. and about 40° C. In a more preferred embodiment, the pharmaceutical compositions are stable when kept at a temperature of between about 25° C. and about 40° C. over a period of time such as a year, and preferably 2 years. More preferably, the pharmaceutical compositions are stable for 3 years.

The pharmaceutical compositions of the invention set forth above in Table 1 may be prepared as set forth in the following PREPARATION EXAMPLE 1. It is understood, however, that that one skilled in the art would be able to prepare the pharmaceutical compositions by similar methods or by methods known to one skilled in the art. It is also understood that one skilled in the art would be able to prepare in a similar manner as described below other pharmaceutical compositions of the invention not specifically illustrated below by using the appropriate components and modifying the parameters of the preparation as needed.

Preparation Example 1

A standard manufacturing vessel with a propeller/shaft is tared and the tare weight recorded. With continuous propeller mixing, oleyl alcohol, isopropyl myristate, Transcutol® P, PEG 3350, stearyl alcohol, PEG 400 and butylated hydroxytoluene (BHT) are added to the vessel in the amounts listed above in Table 1, one excipient at a time until a homogenous solution is obtained before the addition of the next excipient, at preferably 60° C. to 70° C. To the resultant mixture is added the desired amount of COMPOUND A, or a pharmaceutically acceptable salt thereof, in the amount listed above in Table 1 at preferably 60° C. to 70° C. The resultant mixture is mixed for a suitable period of time, preferably for a period of time of between about 30 minutes and about 1 hour. Upon completion (when COMPOUND A, or a pharmaceutically acceptable salt thereof, is completely dissolved), the propeller mixer is removed and the homogenization process is started. A Silverson Mixer (Model No. L4RT) is used for the homogenization, where the homogenization is carried out for 10 minutes and the rotor speed is kept at 6000 rpm. During the homogenization process, the temperature of the solution is constantly monitored and is kept at preferably between about 60° C. and about 70° C. After the homogenization is completed, the heat source is removed to cool the mixture, and quickly switched to propeller mixing until an ointment is formed and the temperature reaches a suitable temperature, preferably 35° C. or below. The sides of the vessel are continuously scraped down during the cooling and mixing stage to ensure the ointment is homogenous. The resulting ointment is then transferred to an appropriate container.

The process described above can be carried out utilizing conventional equipment and under conventional conditions known to those skilled in the art. All of the raw materials were used as obtained from the various manufactures with the following exception of COMPOUND A, which is obtained as described herein.

Administration of the Pharmaceutical Compositions of the Invention

The pharmaceutical compositions of the invention are to be topically administered to a mammal, preferably a human. The pharmaceutical composition is applied topically to a site at or adjacent to a region where the treatment is desired. Typically, one to four applications per day of a pharmaceutical composition of the invention are recommended during the treatment period, or it can be reapplied as often as necessary. Relief is typically obtained within minutes and lasts for periods of variable duration ranging from minutes to hours to even, in some cases, days. Generally, the amount of the pharmaceutical formulation of the invention applied to the affected skin area ranges from about 0.02 g/cm² of skin surface area to about 0.5 g/cm², preferably, 0.1 g/cm² to about 0.30 g/cm² of skin surface area.

In some embodiments, the pharmaceutical composition of the invention, when topically administered to the skin of a mammal in need thereof, exerts only a local effect. In other embodiments, the pharmaceutical composition of the invention, when topically administered to the skin of a mammal in need thereof, additionally has a systemic effect.

Application of the pharmaceutical composition of the invention may be performed by a medical professional or by the patient. In certain embodiments, for maximum effectiveness and increased absorption, the area to which the pharmaceutical composition of the invention is to be administered is first cleansed, for example using an astringent, such as a standard commercial antiseptic or alcohol. The area is then allowed to dry, and the pharmaceutical composition of the invention is applied onto the target area and rubbed until all the pharmaceutical composition has been absorbed or no residue remains on the skin.

Typically, a successful therapeutic effective amount of a pharmaceutical composition of the invention will meet some or all of the following criteria. As will be appreciated by one skilled in the art, the therapeutically effective dosage of a spiro-oxindole compound of the invention, as an enantiomer, a racemate or a non-racemic mixture of enantiomers, preferably as COMPOUND A, or a pharmaceutically acceptable salt thereof, will be such that it is effective for its intended purpose (e.g., prevent, reduce or alleviate pain). In general, a spiro-oxindole compound of the invention, as an enantiomer, a racemate or a non-racemic mixture of enantiomers, preferably as COMPOUND A, or a pharmaceutically acceptable salt thereof, is present in a pharmaceutical composition of the invention in an amount of from about 2% to about 10% of the total weight of the composition, preferably in an amount of from about 4% to about 8% of the total weight of the composition, more preferably, of from about 4% to about 6% of the total weight of the composition.

The potency (as expressed by $IC_{50}$ value) of COMPOUND A, or a pharmaceutically acceptable salt thereof, should be less than 10 µM, preferably below 1 µM and most preferably below 50 nM. The $IC_{50}$ ("Inhibitory Concentration—50%") is a measure of the amount of compound required to achieve 50% inhibition of ion flux through a sodium channel, over a specific time period, in an assay of the invention. For example, COMPOUND A, or a pharmaceutically acceptable salt thereof, when tested in the guanidine influx assay disclosed in PCT Published Patent Application No. WO 06/110917, demonstrated an $IC_{50}$ of less than 1 µM concentration.

The recipients of administration of the pharmaceutical compositions of the invention can be any vertebrate animal, such as mammals. Among mammals, the preferred recipients are mammals of the Orders Primate (including humans, apes and monkeys), Arteriodactyla (including horses, goats, cows, sheep, and pigs), Rodenta (including mice, rats, rabbits, and hamsters), and Carnivora (including cats, and dogs). Among birds, the preferred recipients are turkeys, chickens and other members of the same order. The most preferred recipients are humans.

Combination Therapy

The pharmaceutical compositions of the invention may be usefully combined with one or more other therapeutic agent or as any combination thereof, in the treatment of sodium channel-mediated diseases and conditions. For example, the pharmaceutical composition of the invention may be administered simultaneously, sequentially or separately in combination with other therapeutic agents, including, but not limited to:

opiates analgesics, e.g., morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine;

non-opiate analgesics, e.g., acetomeniphen, and salicylates (e.g., aspirin);

nonsteroidal antiinflammatory drugs (NSAIDs), e.g., ibuprofen (Advil®), naproxen, fenoprofen, ketoprofen, diclofenac, diflusinal, etodolac, fenbufen, flufenisal, flurbiprofen, indomethacin, ketorolac, meclofenamic acid, mefenamic acid, meloxicam, nabumetone, nimesulide, nitroflurbiprofen, olsalazine, oxaprozin, phenylbutazone, piroxicam, sulfasalazine, sulindac, tolmetin and zomepirac;

anticonvulsants, e.g., carbamazepine, oxcarbazepine, lamotrigine, gabapentin and pregabalin;

antidepressants such as tricyclic antidepressants, e.g., amitriptyline, clomipramine, despramine, imipramine, duloxetine and nortriptyline;

COX-2 selective inhibitors, e.g., celecoxib, rofecoxib, parecoxib, valdecoxib, deracoxib, etoricoxib, and lumiracoxib;

alpha-adrenergics, e.g., doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl)quinazoline;

barbiturate sedatives, e.g., amobarbital, aprobarbital, butabarbital, butabital, mephobarbital, metharbital, methohexital, pentobarbital, phenobartital, secobarbital, talbutal, theamylal and thiopental;

tachykinin (NK) antagonist, particularly an NK-3, NK-2 or NK-1 antagonist, e.g., ($\alpha$R,9R)-7-[3,5-bis(trifluoromethyl)benzyl)]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis(trifluoromethylphenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

paracetamol;

metabotropic glutamate receptor (mGluR) antagonists;

local anaesthetic such as mexiletine and lidocaine;

corticosteroid such as dexamethasone;

muscarinic antagonists, e.g., tolterodine, propiverine, tropsium t chloride, darifenacin, solifenacin, temiverine and ipratropium;

cannabinoids;

vanilloid receptor agonists (e.g., resinferatoxin) or antagonists (e.g., capsazepine);

topical agents (e.g., lidocaine, capsacin and resiniferotoxin);

muscle relaxants such as benzodiazepines, baclofen, carisoprodol, chlorzoxazone, cyclobenzaprine, methocarbamol and orphrenadine;

anti-histamines or H1 antagonists;

NMDA receptor antagonists;

PDEV inhibitors;

Tramadol®;

cholinergic (nicotinc) analgesics;

alpha-2-delta ligands;

prostaglandin E2 subtype antagonists;

leukotriene B4 antagonists; and 5-lipoxygenase inhibitors

Sodium channel-mediated diseases and conditions that may be treated and/or prevented using such combinations include but not limited to, pain, post-herpetic neuralgia (PHN), post-operative pain, pruritis, pain associated with HIV, HIV treatment induced neuropathy, trigeminal neuralgia, familial erythromelalgia, primary erythromelalgia, familial rectal pain, eudynia, heat sensitivity, pain associated with multiple sclerosis (MS), amyotrophic lateral sclerosis (ALS), painful diabetic neuropathy, peripheral neuropathy, arthritis, rheumatoid arthritis, osteoarthritis, tendonitis, bursitis, musculoskeletal sprains, tenosinovitis, chondromalacia patellae, myositis, myotonia (including but not limited to SCN4A-related myotonia), paramyotonia, rhabdomyolysis, paroxysmal dystonia, myasthenia syndromes, malignant hyperthermia, cystic fibrosis, sodium channel toxin related illnesses, cancer pain, restless leg syndrome, fibromyalgia, and neurodegenerative disease, as well as other neurological disorders including multiple sclerosis.

As used herein "combination" refers to any mixture or permutation of a pharmaceutical composition of the invention with one or more additional therapeutic agent. Unless the context makes clear otherwise, "combination" may include simultaneous or sequentially delivery of a pharmaceutical composition of the invention with one or more therapeutic agents. Unless the context makes clear otherwise, "combination" may include dosage forms of a pharmaceutical composition of the invention with another therapeutic agent. Unless the context makes clear otherwise, "combination" may include different routes of administration of a pharmaceutical composition of the invention with another therapeutic agent. For example, the pharmaceutical composition of the invention is administered topically in combination with another therapeutic agent that is administered orally. Unless the context makes clear otherwise, "combination" may include formulations of a pharmaceutical composition of the invention with another therapeutic agent. Dosage forms, routes of administration and pharmaceutical compositions include, but are not limited to, those described herein.

Article of Manufacture

The present invention also provides kits that contain a pharmaceutical composition of the invention. The kit also includes instructions for the use of the pharmaceutical composition for modulating the activity of sodium channels, for the treatment of pain, as well as other utilities as disclosed herein. Preferably, a commercial package will contain one or more unit doses of the pharmaceutical composition. It will be evident to those of ordinary skill in the art that such compositions which are light and/or air sensitive may require special packaging and/or formulation. For example, packaging may be used which is opaque to light, and/or sealed from contact with ambient air, and/or formulated with suitable coatings or excipients.

The invention may be even better understood by way of the following non-limiting Biological Examples which describe assays which can be performed to demonstrate the utility of the invention.

Biological Example 1

Dose Proportionality in CFA Induced Chronic Inflammatory Pain

In this test, mechanical hyperalgesia is assessed with electronic von Frey filament by means of Electrovonfrey anesthesiometer (Model 2290, IITC Life Science, Woodland Hills, Calif.). Following a full week of acclimatization to the vivarium facility, 150 µL of the "Complete Freund's Adjuvant" (CFA) emulsion (CFA suspended in an oil/saline (1:1) emulsion at a final concentration of 0.5 mg/mL) was injected subcutaneously into the plantar surface of the left hind ankle joint of rats under light isoflurane anaesthesia. Animals were allowed to recover from the anaesthesia and the baseline mechanical nociceptive thresholds of all animals were assessed one week after the administration of CFA. All animals were habituated to the experimental chambers for 20 minutes on the day of the experiment. The animals were then randomly assigned to 5 different test groups including a vehicle control group and 4 pharmaceutical compositions with COMPOUND A at 1%, 2%, 4% and 8% (w/w) groups. After baseline measurements, animals were anaesthetized under isoflurane, shaved at the site of application, and then dosed by application of 50 mg test compositions on the entire ipsilateral hind ankle and foot. Animals were then placed in Plexiglas tubes for 30 minutes to prevent early removal/ingestion of drug. Test compositions were applied twice a day for 3 days. On the fourth day, immediately after application, animals were placed in tubes for 15 minutes and then removed and placed in Plexiglas enclosures for 15 minutes prior to making paw withdrawal measurements. Von Frey withdrawal thresholds were measured as the mean of several independent determinations made within 1-2 minutes of each other on the affected paw of each animal 30 minutes post-dosing. The time point used was previously determined to show the highest analgesic effect for each test composition.

The response thresholds of animals to tactile stimuli were measured using the Model 2290 Electrovonfrey anesthesiometer (IITC Life Science, Woodland Hills, Calif.). Animals were placed in an elevated Plexiglas enclosure set on a mire mesh surface. After 15 minutes of accommodation, a von Frey hair was applied perpendicularly to the plantar surface of the ipsilateral hind paws of the animals with sufficient force, measured in grams, to elicit a crisp response of the paw. The response indicated a withdrawal from the painful stimulus and constituted the efficacy endpoint.

Results

At baseline, there were no significant differences between the means of the von Frey paw withdrawal measurements for the 5 test groups. On the fourth day of dosing at 30 minutes post-dosing, the groups treated with pharmaceutical compositions of COMPOUND A at 2%, 4%, and 8% (w/w) all showed statistically significant increases in the von Frey mechanical paw withdrawal thresholds as expressed by percent change from baseline (CFB) to indicate an analgesic effect (see FIG. 1). The analgesic effect for the compositions with COMPOUND A increased with increasing doses up to the highest dose tested of 8% (w/w), which showed the maximum percent CFB at +45.1%. The 1% (w/w) dosage group, however, did not demonstrate an observable increase in von Frey mechanical paw withdrawal threshold. The results, as set forth in FIG. 1, indicate that compositions of COMPOUND A have analgesic effects in the CFA-induced inflammatory pain model in the range of 2% to 8% (w/v).

Biological Example 2

Time Course of Efficacy in the Neuropathic Pain Model; Chronic Constriction Injury Neuropathic pain is characterized by spontaneous pain and stimulus-evoked allodynia and hyperalgesia. Pharmaceutical compositions of the invention were evaluated in Chronic Constriction Injury model using Sprague-Dawley rats as described below.

An approximately 3 cm incision was made through the skin and the fascia at the mid thigh level of a rat's left hind leg using a no. 10 scalpel blade. The left sciatic nerve was exposed via blunt dissection through the biceps femoris with care to minimize haemorrhagia. Four loose ligatures were tied along the sciatic nerve using four chromic gut sutures at intervals of 1 mm to 2 mm apart. The tension of the loose ligatures was tight enough to induce slight constriction of the sciatic nerve when viewed under a dissection microscope at a magnification of 4 fold. As sham controls, the right sciatic nerve was exposed and manipulated in the same manner as described above, except sutures were not tied onto the nerve. Antibacterial ointment was applied directly into the wound, and the muscle was closed using sterilized sutures. Betadine® was applied onto the muscle and its surroundings, followed by skin closure with surgical clips.

A painful neuropathy was allowed to develop for at least 14 days in the ipsilateral leg as determined by lower paw withdrawal thresholds to a mechanical stimulus. Only those with significant hyperalgesia, as determined by reduced threshold of paw withdrawal to the von Frey filament, measured in grams, were enrolled in the study. All animals enrolled in the study showed paw withdrawal thresholds of <12 g.

The response thresholds of animals to tactile stimuli were measured using the Model 2290 Electrovonfrey anesthesiometer (IITC Life Science, Woodland Hills, Calif.). Animals were placed in an elevated Plexiglass enclosure set on a mire mesh surface. After 15 minutes of accommodation, a von Frey hair was applied perpendicularly to the plantar surface of the ipsilateral hind paws of the animals with sufficient force, measured in grams, to elicit a crisp response of the paw. The response indicated a withdrawal from the painful stimulus and constituted the efficacy endpoint. The force (in grams) required to elicit a crisp withdrawal response was recorded before dosing as a baseline measurement, and at multiple time points post-dosing.

Three days prior to baseline measurement, animals were anaesthetized under isoflurane and the whole of the ipsilateral hind legs, including the upper sciatic notch thigh area, ankle and foot, was shaved. The animals were then randomly assigned to one of 4 different test groups including a vehicle control group, a 5% (w/v) Lidocaine (Xylocaine®), and 2 pharmaceutical compositions of the invention comprising COMPOUND A at 4% (w/w) containing either 5% or 10% Transcutol® P. After baseline measurement, 100 mg of the test composition was applied on the entire shaved area. The animals were then placed in plastic tubes for at least 15 minutes, to prevent early removal/ingestion of drug. Subsequently, animals were placed in the Plexiglas enclosure 15 minutes before von Frey measurement at the respective time points. Von Frey withdrawal thresholds were measured as the mean of several independent determinations made within 1-2 minutes of each other on the affected paw of each animal at 0.5, 1 and 2 hours post dosing.

Results

Figure 2:
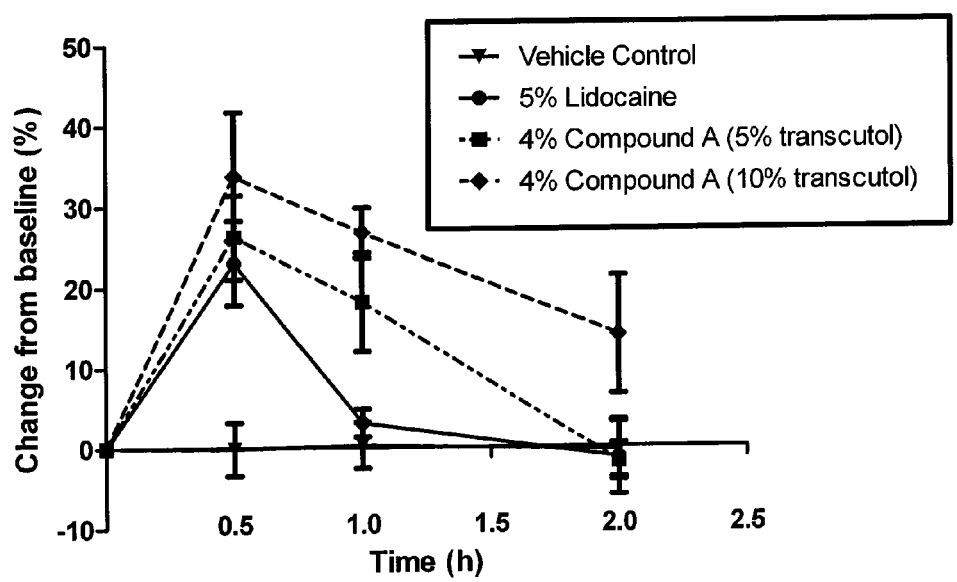
FIG. 2 is a graph showing the mean paw withdrawal threshold expressed as percent change from baseline (CFB) for each treatment group described in the neuropathic pain model study in Example 2. Data are plotted as Mean±SEM.

The percent mean change from baseline (CFB) for each groups' paw withdrawal thresholds is shown in FIG. 2. Observations of +23.1%, +26.3%, and +33.8% CFB were made for the 5% (w/v) lidocaine group and 4% (w/w) COMPOUND A in 5% and 10% Transcutol® P test groups at 0.5 hours post-dosing, respectively. At 1 hour post-dosing, +18.1% and +26.7% CFB were observed for 4% (w/w) COMPOUND A in 5% and 10% Transcutol® P treatment groups respectively. No significant changes (p>0.05) were observed for the 5% (w/v) lidocaine treatment group at any time points later than 0.5 hours post-dosing. The 4% (w/w) COMPOUND A in 10% transcutol group exhibited analgesic effects from 0.5 hour up to 2 hours post-dosing, with improved efficacy and longer duration of analgesia as compared to the 4% (w/w) COMPOUND A in 5% transcutol group. Both groups of 4% (w/w) COMPOUND A exhibited a longer lasting analgesic effect when compared with the 5% lidocaine group, which exhibited analgesic effects only up to 0.5 hours post-dosing in the CCI-induced neuropathic pain model.

Biological Example 3

STZ Model of Diabetic Neuropathy

This study evaluates the efficacy of a pharmaceutical composition of the invention in the STZ-induced neuropathic pain model in male Sprague-Dawley rats, following acute dosing, as compared with a 5% (w/v) topical Lidocaine (Xylocaine®) and a 1.16% (w/v) topical Diclofenac (Voltaren®). A rodent model of painful peripheral diabetic neuropathy (PDN) that mimics human condition was created by inducing a diabetic state in the rat through the ablation of the insulin producing pancreatic beta cells. A single streptozotocin (STZ) injection destroys beta cells in rats and produces a diabetic state that over time progresses to painful Peripheral Diabetic Neuropathy (PDN).

Streptozotocin (STZ) was dissolved in citrate buffer (20 mM, pH 4.5) and administered at a dose of 60 mg/Kg, intraperitoneal, to induce pancreatic beta-cell death. Blood glucose level was measured once a week following injection, using the AccuSoft Blood Glucose Monitoring System. A booster injection was administered two weeks post-initial injection to animals that did not display elevated blood glucose levels following the first injection. Animals with plasma glucose concentrations above 16 mmol/L were considered diabetic and included in the study. Hyperalgesia and allodynia, which are signs of diabetic neuropathic pain, were monitored using the von Frey test as described below. Von Frey measurements were recorded from both left and right paws. Only those with significant hyperalgesia as determined by reduced threshold, measured in grams, of paw withdrawal to the von Frey filament were enrolled in the study. The study was executed during the 8th week following STZ injection. During this time their health status was closely monitored.

The animals were randomly divided into 4 test groups (n=7 animals/group) including a vehicle control, a 5% (w/v) Lidocaine (Xylocaine®), a 1.16% (w/v) Diclofenac (Voltaren®), and a pharmaceutical composition with 4% (w/w) COMPOUND A. After baseline measurement, 50 mg of the test composition was applied on the entire left foot. Animals were then placed in Plexiglas tubes for 15 minutes to prevent early removal/ingestion of drug, and then moved to the Plexiglas enclosure for von Frey measurement. The paw withdrawal thresholds of animals from mechanical tactile stimuli were measured using the Electrovonfrey anesthesiometer (Model 2290, IITC Life Science, Woodland Hills, Calif.). Animals were placed in an elevated acrylic enclosure set on a wire mesh surface. After 15 minutes of accommodation, a flexible von Frey hair (tip #15) was applied perpendicularly to the plantar surface of the ipsilateral hind paws of the animals, with sufficient force to elicit a crisp response of the paw. The response indicated a withdrawal from the painful stimulus and constitutes the efficacy endpoint. The force (g) required to elicit a crisp withdrawal response was recorded before dosing as a baseline measurement, and at 30 minutes post-dosing.

Withdrawal measurements were recorded from both the treated (left) and un-treated (right) paws. The von Frey paw withdrawal data were analyzed using GraphPad Prism 5 statistical analysis software. One-way ANOVA was used for multivariate analysis with Bonferroni adjustment. Unpaired t-test was used for univariate analysis. Results are expressed as mean±SEM. Values that reached a $p<0.05$ level of significance were considered statistically significant.

Results

At baseline, there were no significant differences between the four test groups in the von Frey paw withdrawal measurements for treated paws, nor were there differences between the left and right hind paw measurements.

Figure 3:
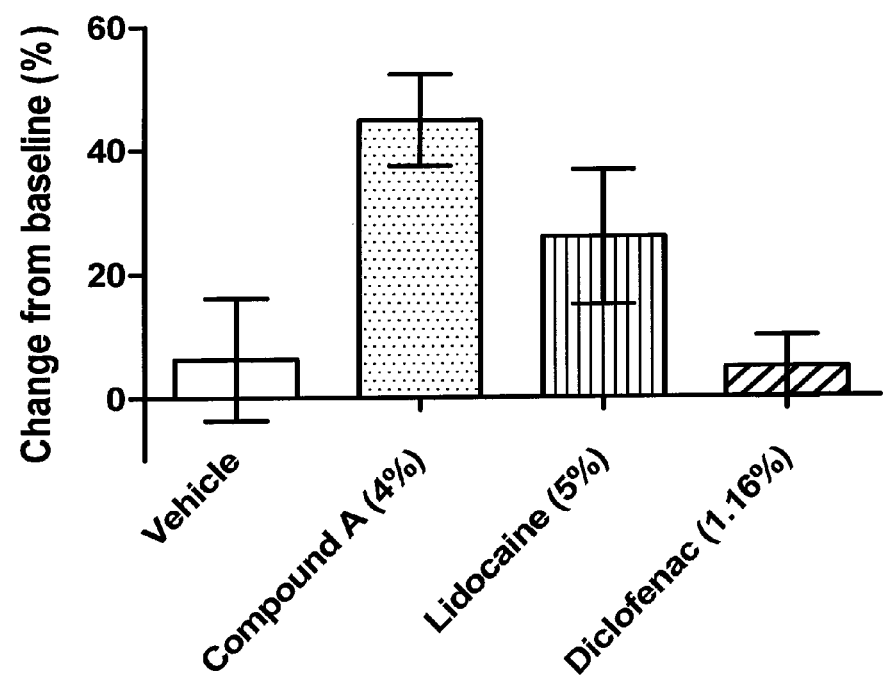
FIG. 3 is a graph showing 30-minute post-dosing von Frey Change from Baseline (CFB) for treated paw from the diabetic neuropathy study in Example 4.

At 30 minutes post-dosing, the percent mean change from baseline (CFB) for each groups' paw withdrawal thresholds (of treated paws) is provided in FIG. 3. The change from baseline reached 44.9% for the 4% (w/w) COMPOUND A dosage group ($p<0.05$), substantially above the 25.9% change from baseline observed in the 5% (w/v) Lidocaine group. No significant CFB was observed in the 1.16% (w/v) Diclofenac group.

Therefore, a local analgesic effect was observed for composition containing 4% (w/w) COMPOUND A in the STZ-induced neuropathic pain model at 30 minutes post-dosing, manifesting as a 44.9% change from baseline, greater than the local efficacy observed with the reference compounds.

Biological Example 4

Relationship Between Efficacy and Systemic Exposure for Topical and Oral Administration; Chronic Constriction Injury The Chronic Constriction Injury (CCI) model, an established neuropathic pain model in the rat, is used in this study to compare the levels of efficacy and systemic exposure of COMPOUND A between the topical and oral administration in male rats.

A peripheral neuropathy was induced in rats by placing loose constrictive ligatures around the common sciatic nerve as described by Bennett G J, and Xie Y-K., Pain, (1988) 33: pp. 87-107. Eight-week old male Sprague Dawley rats were anaesthetized with 3.5% isoflurane, and a 3 cm incision was made through the skin and fascia at the mid-thigh level of the animal's left hind leg using a no. 10 scalpel blade. The left sciatic nerve was exposed via blunt dissection through the biceps femoris, with care taken to minimize haemorrhagia. Four loose ligatures were tied along the sciatic nerve using four chromic gut sutures at intervals of 1 mm to 2 mm apart. The tension of the loose ligatures was tight enough to induce slight constriction of the sciatic nerve when viewed under a dissection microscope at a magnification of 4 fold. Antibacterial ointment was applied directly into the wound, and the muscle was closed using sterilized sutures. Betadine® was applied onto the muscle and its surroundings, followed by skin closure with surgical clips.

A painful neuropathy was allowed to develop in the ipsilateral leg as determined by lower paw withdrawal thresholds to a mechanical stimulus. Only those with significant hyperalgesia as determined by reduced threshold, measured in grams, to paw withdrawal to the von Frey filament were enrolled in the study. All animals enrolled in the study showed paw withdrawal thresholds of <12 g.

The paw withdrawal thresholds of animals from mechanical tactile stimuli were measured using the Model 2290 Electrovonfrey anesthesiometer (IITC Life Science, Woodland Hills, Calif.). Animals were placed in an elevated Plexiglass enclosure set on a wire mesh surface. After 15 minutes of accommodation in this enclosure, a von Frey hair was applied perpendicularly to the plantar surface of the ipsilateral hind paws of the animals, with sufficient force, measured in grams, to elicit a crisp response of the paw. The response indicated a withdrawal from the painful stimulus and constituted the efficacy endpoint.

Following paw withdrawal baseline measurements, animals were randomly divided into 4 different test groups (N=8 animals/group), including a vehicle control group for oral dosage, a vehicle control group for topical dosage, and two treatment groups. For the oral dosage groups, animals were dosed by oral gavages after baseline measurement. Doses of COMPOUND A were chosen based on previous studies indicating that the oral dose of 25 mg/Kg of COMPOUND A produces an approximately half-maximal reversal of pain response and a level of efficacy comparable to that of the pharmaceutical composition of the invention comprising COMPOUND A at 8% (w/w). For the topical dosage groups, 50 mg of the test composition was applied on the ipsilateral ankle and foot. Animals were then placed in plastic tubes for 15 minutes, to prevent early removal/ingestion of drug. Subsequently, animals were placed in the Plexiglass enclosure for 15 minutes prior to paw withdrawal measurement. Von Frey withdrawal thresholds were measured as the mean of several independent determinations made within 1-2 minutes of each other on the affected paw of each animal. Withdrawal measurements were taken 60 minutes post dosing for the oral dosage group and 30 minutes post-dosing for the topical dosage group, representing their respective peak efficacy time points as determined in previous studies.

Blood samples were taken from the same animals immediately after withdrawal threshold measurements using the following procedure at approximately 10-15 minutes after their respective efficacy time points. The rats were bled by jugular vein puncture while under anaesthesia. The time at which each blood sample was drawn, relative to the time of dosing, was recorded. Each blood sample (~150 μL) was collected into a heparin-coated, labelled microvette tube containing 10 μL of heparin (100 Units) and placed on ice immediately. The blood samples were centrifuged at 4° C. to separate the plasma. The plasma was transferred to labelled tubes and snap-frozen in liquid nitrogen for storage at −80° C. At the time of analysis, the plasma was thawed and extracted using solid phase extraction, and the plasma drug concentration was quantified by HPLC/MS/MS.

The von Frey paw withdrawal data were analyzed using GraphPad Prism 5 statistical analysis software. One-way ANOVA was used for multivariate analysis with Bonferroni adjustment. Unpaired t-test was used for univariate analysis. Results are expressed as mean±SEM. Values that reached a p<0.05 level of significance were considered statistically significant.

Results

At baseline, there were no significant differences between the means of the von Frey paw withdrawal measurements for the four test groups.

Figure 4:
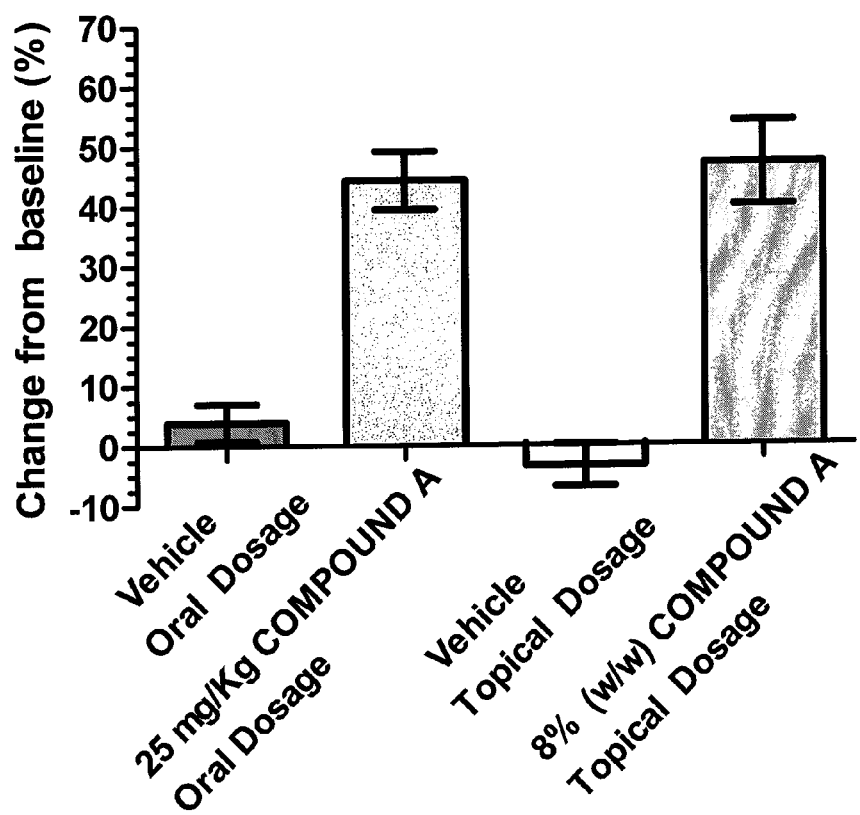
FIG. 4 is a graph showing the mean percent change from baseline (CFB) for each dosage group described in the CCI model for neuropathic pain study in Example 5. Data are expressed as Mean±SD change from baseline values.

The percent mean Change From Baseline (CFB) for each groups' paw withdrawal thresholds is shown in FIG. 4. At 60 and 30-minute post-dosing, the CFB reached 44.3% for the 25 mg/Kg COMPOUND A oral dosage group and 47.1% for the 8% (w/w) COMPOUND A topical dosage group respectively, which was statistical significance (p<0.001) when compared to the vehicle groups and indicated an analgesic effect. No statistical significance was observed between the CFB of the oral and topical dosage groups (p=0.742).

Figure 5:
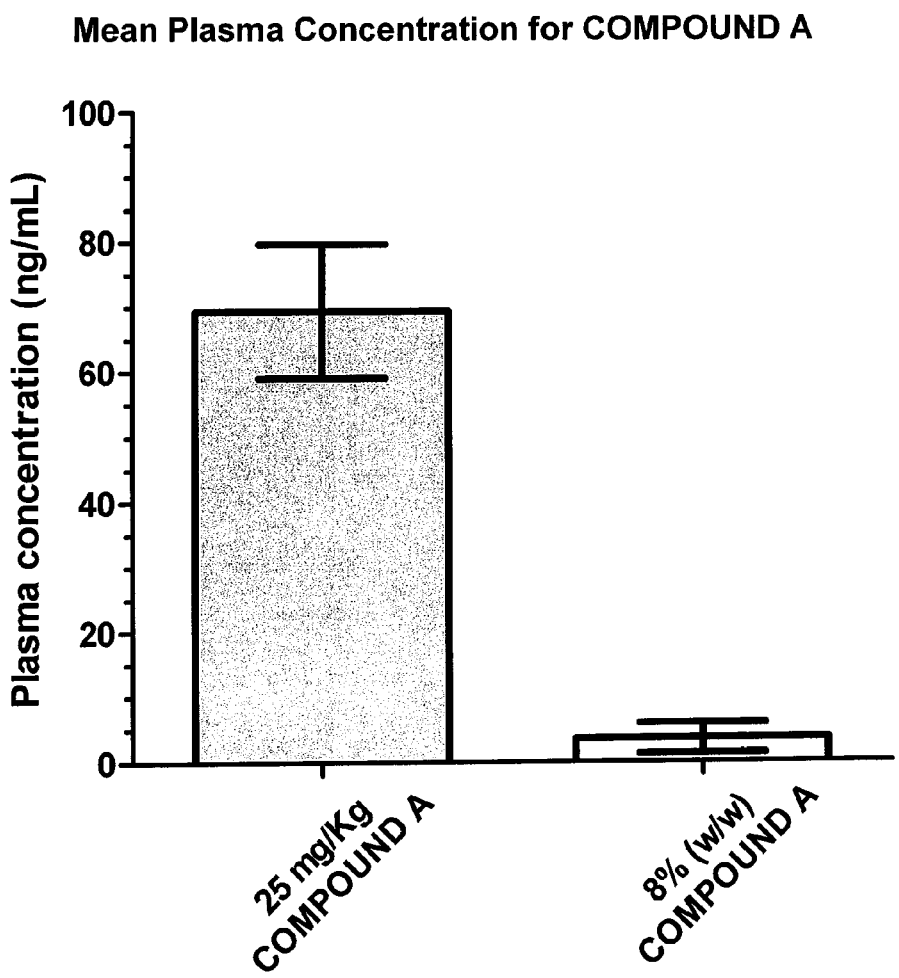
FIG. 5 is a graph showing the mean plasma concentration of COMPOUND A for each treatment group described in the CCI model study in Example 5.

Plasma samples were collected from the animals immediately after von Frey testing. The systemic plasma concentration of COMPOUND A for the oral and topical dosage groups is shown in FIG. 5. The plasma level of COMPOUND A in the topical dosage group was significantly lower (~20×) than the level in the oral dosage group (p<0.0001).

8% (w/w) COMPOUND A by topical administration exhibited a degree of efficacy (47% CFB) that is comparable to 25 mg/kg COMPOUND A (44% CFB) by oral administration in the CCI neuropathic pain model. Systemic plasma exposure of COMPOUND A was significantly lower (~20×) in the topical dosage group than the oral dosage group. Therefore, COMPOUND A given by topical administration in the CCI neuropathic pain model provides efficacy comparable to COMPOUND A by oral administration with minimal systemic exposure.

Unless indicated otherwise, any U.S. patent, U.S. patent application publication, or PCT published patent application referred to in this specification is incorporated herein by reference in its entirety, including U.S. Provisional Patent Application No. 61/308,759.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A pharmaceutical composition for topical administration to a mammal comprising two or more pharmaceutically acceptable excipients and a therapeutically effective amount of a spiro-oxindole compound having the following formula:

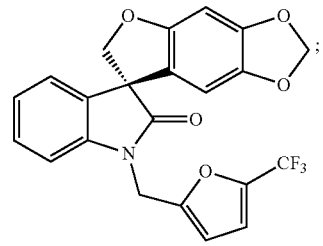 [SMILES: O=C1N(Cc2ccc(C(F)(F)F)o2)c2ccccc2[C@]12COc1cc3c(cc12)OCO3]

or a pharmaceutically acceptable salt thereof, wherein each pharmaceutically acceptable excipient is present in a concentration of from about 0.01% w/w to about 99% w/w, wherein the pharmaceutically acceptable excipients are selected from one or more solvents, one or more penetration enhancing agents, one or more stiffening agents, one or more ointment bases and, optionally, one or more antioxidants, and wherein a solvent is selected from PEG 400 or PEG 3350, a penetration enhancing agent is selected from diethylene glycol monoethyl ether, oleyl alcohol, or isopropyl myristate, a stiffening agent is stearyl alcohol, an ointment base is selected from PEG 400 or PEG 3350, and the antioxidant, if present, is butylated hydroxytoluene (BHT).

2. The pharmaceutical composition of claim 1, comprising one or more antioxidants.

3. The pharmaceutical composition of claim 1, wherein PEG 400 is present in a concentration of from about 30% w/w to about 70% w/w, diethylene glycol monoethyl ether is present in a concentration of from about 2% w/w to about 25% w/w, oleyl alcohol is present in a concentration of from about 1% w/w to about 10% w/w, isopropyl myristate is present in a concentration of from about 1% w/w to about 25% w/w, stearyl alcohol is present in a concentration of from about 0.1% w/w to about 10% w/w, BHT, if present, is present in a concentration of from about 0.01% w/w to about 2% w/w, and PEG 3350 is present in a concentration of from about 10% w/w to about 50% w/w.

4. The pharmaceutical composition of claim 3, wherein PEG 400 is present in a concentration of from about 45% w/w to about 55% w/w, diethylene glycol monoethyl ether is present in a concentration of from about 5% w/w to about 15% w/w, oleyl alcohol is present in a concentration of from about 2.5% w/w to about 7.5% w/w, isopropyl myristate is present in a concentration of from about 2.5% w/w to about 7.5% w/w, stearyl alcohol is present in a concentration of from about 0.1% w/w to about 7.5% w/w, BHT, if present, is present in a concentration of from about 0.05% w/w to about 1% w/w, and PEG 3350 is present in a concentration of from about 15% w/w to about 30% w/w.

5. The pharmaceutical composition of claim 4, wherein the spiro-oxindole compound is present in a concentration of from about 0.1% w/w to about 10% w/w.

6. The pharmaceutical composition of claim 5, wherein the spiro-oxindole compound is present in a concentration of from about 2% w/w to about 8% w/w.

7. The pharmaceutical composition of claim 1 comprising the spiro-oxindole compound at a concentration of 2.0% w/w; PEG 400 at a concentration of 52.9% w/w; diethylene glycol monoethyl ether at a concentration of 10% w/w; oleyl alcohol at a concentration of 5% w/w; isopropyl myristate at a concentration of 5% w/w; stearyl alcohol at a concentration of 5% w/w; butylated hydroxytoluene at a concentration of 0.1% w/w; and PEG 3350 at a concentration of 20% w/w of the pharmaceutical composition.

8. The pharmaceutical composition of claim 1 comprising the spiro-oxindole compound at a concentration of 4% w/w; PEG 400 at a concentration of 50.9% w/w; diethylene glycol monoethyl ether at a concentration of 10% w/w; oleyl alcohol at a concentration of 5% w/w; isopropyl myristate at a concentration of 5% w/w; stearyl alcohol at a concentration of 5% w/w; butylated hydroxytoluene at a concentration of 0.1% w/w; and PEG 3350 at a concentration of 20% w/w of the pharmaceutical composition.

9. The pharmaceutical composition of claim 1 comprising the spiro-oxindole compound at a concentration of 4% w/w; PEG 400 at a concentration of 50.9% w/w; diethylene glycol monoethyl ether at a concentration of 5% w/w; oleyl alcohol at a concentration of 5% w/w; isopropyl myristate at a concentration of 5% w/w; stearyl alcohol at a concentration of 10% w/w; butylated hydroxytoluene at a concentration of 0.1% w/w; and PEG 3350 at a concentration of 20% w/w of the pharmaceutical composition.

10. The pharmaceutical composition of claim 1 comprising the spiro-oxindole compound at a concentration of 8% w/w; PEG 400 at a concentration of 46.9% w/w; diethylene glycol monoethyl ether at a concentration of 10% w/w; oleyl alcohol at a concentration of 5% w/w; isopropyl myristate at a concentration of 5% w/w; stearyl alcohol at a concentration of 5% w/w; butylated hydroxytoluene at a concentration of 0.1% w/w; and PEG 3350 at a concentration of 20% w/w of the pharmaceutical composition.

11. A method of inhibiting osteoarthritis, relieving osteoarthritis or relieving the symptoms of osteoarthritis in a mammal, wherein the method comprises topically administering to the mammal in need thereof a therapeutically effective amount of a pharmaceutical composition of claim 1.

12. The method of claim 11, wherein the mammal is a human.

* * * * *